(12) United States Patent
Trono et al.

(10) Patent No.: US 9,023,646 B2
(45) Date of Patent: *May 5, 2015

(54) METHODS AND COMPOSITIONS RELATING TO IMPROVED LENTIVIRAL VECTORS AND THEIR APPLICATIONS

(71) Applicant: Research Development Foundation, Carson City, NV (US)

(72) Inventors: Didier Trono, Vufflens-le-Chateau (CH); Patrick Salmon, Arenthon (FR)

(73) Assignee: Research Development Foundation, Carson City, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/022,121

(22) Filed: Sep. 9, 2013

(65) Prior Publication Data

US 2014/0220678 A1 Aug. 7, 2014

Related U.S. Application Data

(63) Continuation of application No. 13/622,309, filed on Sep. 18, 2012, now Pat. No. 8,551,773, which is a continuation of application No. 12/537,789, filed on Aug. 7, 2009, now Pat. No. 8,329,462, which is a continuation of application No. 10/010,081, filed on Nov. 9, 2001, now Pat. No. 7,575,924.

(60) Provisional application No. 60/248,398, filed on Nov. 13, 2000.

(51) Int. Cl.
| | | |
|---|---|---|
| C12N 5/071 | (2010.01) | |
| C12N 15/86 | (2006.01) | |
| C07K 14/55 | (2006.01) | |
| C07K 14/705 | (2006.01) | |
| C07K 16/46 | (2006.01) | |
| A61K 48/00 | (2006.01) | |

(52) U.S. Cl.
CPC .................. *C12N 15/86* (2013.01); *A61K 48/00* (2013.01); *C12N 2740/16043* (2013.01); *C12N 2740/16045* (2013.01); *C12N 2800/108* (2013.01); *C12N 2830/50* (2013.01); *C12N 2840/20* (2013.01); *C07K 14/55* (2013.01); *C07K 14/70503* (2013.01); *C07K 16/46* (2013.01)

(58) Field of Classification Search
None
See application file for complete search history.

(56) References Cited

U.S. PATENT DOCUMENTS

| | | | |
|---|---|---|---|
| 4,682,195 A | 7/1987 | Yilmaz | 357/23.4 |
| 4,683,202 A | 7/1987 | Mullis | 435/91 |
| 5,015,573 A | 5/1991 | Yarranton et al. | 435/69.1 |
| 5,019,384 A | 5/1991 | Gefter et al. | 424/184.1 |
| 5,466,468 A | 11/1995 | Schneider et al. | 424/450 |
| 5,645,897 A | 7/1997 | Andra | 427/526 |
| 5,686,279 A | 11/1997 | Finer et al. | 435/172.3 |
| 5,705,629 A | 1/1998 | Bhongle | 536/25.34 |
| 5,846,225 A | 12/1998 | Rosengart et al. | 604/115 |
| 5,846,233 A | 12/1998 | Lilley et al. | 604/414 |
| 5,885,570 A | 3/1999 | Isobe et al. | 424/93.71 |
| 5,912,411 A | 6/1999 | Bujard et al. | 800/18 |
| 5,925,565 A | 7/1999 | Berlioz et al. | 435/325 |
| 5,928,906 A | 7/1999 | Koster et al. | 435/91.2 |
| 5,935,819 A | 8/1999 | Eichner et al. | 435/69.4 |
| 5,981,830 A | 11/1999 | Wu et al. | 800/18 |
| 5,994,136 A | 11/1999 | Naldini et al. | 435/455 |
| 6,013,516 A | 1/2000 | Verma et al. | 435/325 |
| 6,013,517 A | 1/2000 | Respess et al. | 435/325 |
| 6,017,758 A | 1/2000 | Haselton, III et al. | 435/325 |
| 6,031,517 A | 2/2000 | Van Nes | 345/600 |
| 6,084,063 A | 7/2000 | Vonakis et al. | 530/324 |
| 6,096,538 A | 8/2000 | Kingsman et al. | 435/325 |
| 6,136,597 A | 10/2000 | Hope et al. | 435/325 |
| 6,165,782 A | 12/2000 | Naldini et al. | 435/320.1 |
| 6,168,916 B1 | 1/2001 | Kingsman et al. | 435/5 |
| 6,207,455 B1 | 3/2001 | Chang | 435/457 |
| 6,218,181 B1 | 4/2001 | Verma et al. | 435/369 |

(Continued)

FOREIGN PATENT DOCUMENTS

| | | |
|---|---|---|
| EP | 0266032 | 5/1988 |
| EP | 0476953 | 3/1992 |
| EP | 1229134 | 8/2002 |
| EP | 1371727 | 12/2003 |
| WO | WO 99/00510 | 1/1999 |

(Continued)

OTHER PUBLICATIONS

"A Phase I study of Ex vivo nerve growth factor gene therapy for Alzheimer's disease," sponsored by the Shiley Family Trust Institute for the Study of Aging, University of California, San Diego, Study ID Nos. IA0029, last reviewed Jun. 2001.

(Continued)

*Primary Examiner* — Michael Burkhart
(74) *Attorney, Agent, or Firm* — Parker Highlander PLLC

(57) ABSTRACT

The present invention provides HIV-derived lentivectors which are safe, highly efficient, and very potent for expressing transgenes for human gene therapy, especially, in human hematopoietic progenitor cells as well as in all other blood cell derivatives. The lentiviral vectors comprise a self-inactivating configuration for biosafety and promoters such as the EF1 α promoter as one example. Additional promoters are also described. The vectors can also comprise additional transcription enhancing elements such as the wood chuck hepatitis virus post-transcriptional regulatory element. These vectors therefore provide useful tools for genetic treatments such as inherited and acquired lympho-hematological disorders, gene-therapies for cancers especially the hematological cancers, as well as for the study of hematopoiesis via lentivector-mediated modification of human HSCs.

18 Claims, 12 Drawing Sheets

(56) References Cited

U.S. PATENT DOCUMENTS

| | | | |
|---|---|---|---|
| 6,218,186 B1 | 4/2001 | Choi et al. ................... | 435/456 |
| 6,235,522 B1 | 5/2001 | Kingsman et al. .......... | 435/320.1 |
| 6,242,258 B1 | 6/2001 | Haselton, III et al. ....... | 435/455 |
| 6,271,359 B1 | 8/2001 | Norris et al. ................ | 536/23.14 |
| 6,277,633 B1 | 8/2001 | Olsen ......................... | 435/320.1 |
| 6,312,682 B1 | 11/2001 | Kingsman et al. ........... | 424/93.2 |
| 6,312,683 B1 | 11/2001 | Kingsman et al. ........... | 424/93.2 |
| 6,340,741 B1 | 1/2002 | Mermod et al. .............. | 530/350 |
| 6,410,313 B1 | 6/2002 | Kasahara et al. ............ | 435/320.1 |
| 6,428,953 B1 | 8/2002 | Naldini et al. ............... | 435/5 |
| 6,440,730 B1 | 8/2002 | Von Laer et al. ............ | 435/325 |
| 6,444,871 B1 | 9/2002 | Yao ............................ | 800/4 |
| 6,485,965 B1 | 11/2002 | Klatzmann et al. .......... | 435/320.1 |
| 6,531,123 B1 | 3/2003 | Chang ........................ | 424/93.2 |
| 6,669,936 B2 | 12/2003 | Kingsman et al. .......... | 424/93.21 |
| 6,682,907 B1 | 1/2004 | Charneau et al. ........... | 435/69.1 |
| 6,727,058 B2 | 4/2004 | Bushman et al. ............ | 435/325 |
| 6,852,703 B1 | 2/2005 | Kingsman et al. ........... | 514/44 |
| 6,864,085 B2 | 3/2005 | Luo et al. ................... | 435/320.1 |
| 7,202,079 B2 | 4/2007 | Luo et al. ................... | 435/320.1 |
| 7,629,153 B2 | 12/2009 | Trono et al. ................. | 435/91.4 |
| 2002/0034393 A1 | 3/2002 | Mitrophanous et al. ...... | 396/661 |
| 2002/0048805 A1 | 4/2002 | Johnston et al. ............. | 435/235.1 |
| 2002/0123471 A1 | 9/2002 | Uberla ........................ | 514/44 |
| 2002/0160393 A1 | 10/2002 | Symonds et al. ............ | 435/6 |
| 2003/0068821 A1 | 4/2003 | Lois-Caballe et al. ....... | 435/456 |
| 2003/0082789 A1 | 5/2003 | Trono et al. ................. | 435/235.1 |
| 2003/0119770 A1 | 6/2003 | Lai et al. .................... | 514/44 |
| 2007/0270580 A1 | 11/2007 | Mauro et al. ................ | 536/23.1 |
| 2010/0041141 A1 | 2/2010 | Trono et al. ................. | 435/369 |
| 2010/0062524 A1 | 3/2010 | Trono et al. ................. | 435/320.1 |
| 2014/0220678 A1* | 8/2014 | Trono et al. ................. | 435/328 |

FOREIGN PATENT DOCUMENTS

| | | |
|---|---|---|
| WO | WO 99/04026 | 1/1999 |
| WO | WO 99/36511 | 7/1999 |
| WO | WO 99/51754 | 10/1999 |
| WO | WO 99/55892 | 11/1999 |
| WO | WO 00/12737 | 3/2000 |
| WO | WO 00/15819 | 3/2000 |
| WO | WO 00/55335 | 9/2000 |
| WO | WO 00/66758 | 11/2000 |
| WO | WO 01/27300 | 4/2001 |
| WO | WO 01/27304 | 4/2001 |
| WO | WO 01/34843 | 5/2001 |
| WO | WO 01/44458 | 6/2001 |
| WO | WO 01/44481 | 6/2001 |
| WO | WO 01/68836 | 9/2001 |
| WO | WO 01/92506 | 12/2001 |
| WO | WO 02/066638 | 8/2002 |
| WO | WO 02/087341 | 11/2002 |
| WO | WO 03/022052 | 3/2003 |
| WO | WO 03/072788 | 9/2003 |

OTHER PUBLICATIONS

"Ceregene exclusively licenses Neuturin gene from Washington Unviersity," Ceregene, Inc. Press Release, Dec. 4, 2002.

Abbas-Terki et al., "Lentiviral-mediated RNA interference," *Human Gene Ther.*, 13:2197-2201, 2002.

Akkina et al., "High-efficiency gene transfer into CD34+ cells with a human immunodeficiency virus type 1-based retroviral vector pseudotyped with vesicular stomatitis virus envelope glycoprotein G," *J. Virol.*, 70:2581-2585, 1996.

Allikian et al., "Doxycycline-induced expression of sense and inverted-repeat constructs modulates phosphogluconate mutase (Pgm) gene expression in adult *Drosophila melanogaster*," *Genome Biology*, 3(5):0021.1-0021.10, 2002.

Almendro et al., "Cloning of the human platelet endothelial cell adhesion molecule-1 promoter and its tissue-specific expression. Structural and functional characterization," *J. Immunol.*, 157(12):5411-5421, 1996.

An et al., "Marking and gene expression by a lentivirus vector in transplanted human and nonhuman primate CD34(+) cells," *J. Virol.*, 74:1286-1295, 2000.

Anderson, "Human gene therapy," *Nature*, 392:25-30, 1998.

Angel et al.,"12-0-tetradecanoyl-phorbol-13-acetate Induction of the Human Collagenase Gene is Mediated by an Inducible Enhancer Element Located in the 5' Flanking Region," *Mol. Cell. Biol.*, 7:2256-2266, 1987.

Angel et al., "Phorbol Ester-Inducible Genes Contain a Common cis Element Recognized by a TPA-Modulated Trans-acting Factor," *Cell*, 49:729-739, 1987.

Archambault and Friesen, "Genetics of Eukaryotic RNA Polymerases I, II , and III" *Microbiol. Reviews*, 57:703-724, 1993.

Arrighi et al., "Long-term culture of human CD34(+) progenitors with FLT3-ligand, thrombopoietin, and stem cell factor induces extensive amplification of a CD34(−)CD14(−) and CD34(−)CD14(+) dendritic cell precursor," *Blood*, 93:2244-2252, 1999.

Atchison and Perry, "Tandem Kappa Immunoglobulin Promoters are Equally Active in the Presence of the Kappa Enhancer: Implications for Model of Enhancer Function," *Cell*, 46:253-262, 1986.

Atchison and Perry, "The Role of the κ Enhancer and its Binding Factor NF-κB in the Developmental Regulation of κ Gene Transcription," *Cell*, 48:121-128, 1987.

Ayer et al., "Mad proteins contain a dominant transcription repression domain," *Mol. Cell. Biol.*, 16:5772-5781, 1996.

Baim et al., "A chimeric mammalian transactivator based on the lac repressor that is regulated by temperature and isopropyl β-D-thiogalactopyranoside," *Proc. Natl. Acad. Sci., USA*, 88:5072-5076, 1991.

Banerji et al., "A lymphocyte-specific cellular enhancer is located downstream of the joining region in immunoglobulin heavy-chain genes," *Cell*, 35:729-740, 1983.

Banerji et al., "Expression of a Beta-Globin Gene is Enhanced by Remote SV40 DNA Sequences," *Cell*, 27:299-308, 1981.

Barton and Medzhitov, "Retroviral delivery of small interfering RNA into primary cells," *Proc. Natl. Acad. Sci., USA*, 99(23):14943-14945, 2002.

Bellefroid et al., "The evolutionary conserved Krüppel-associated box domain defines a subfamily of eukaryotic multifingered proteins," *Proc. Natl. Acad. Sci. USA*, 88:3608-3612, 1991.

Berkhout et al., "Tat Trans-activates the Human Immunodeficiency Virus Through a Nascent RNA Target," *Cell*, 59:273-282, 1989.

Bhatia et al., "Quantitative analysis reveals expansion of human hematopoietic repopulating cells after short-term ex vivo culture," *J. Exp. Med.*, 186:619-624, 1997.

Blanar et al., "A gamma-interferon-induced factor that binds the interferon response sequence of the MHC class I gene, H-2Kb," *EMBO J.*, 8:1139-1144, 1989.

Blömer et al., "Highly efficient and sustained gene transfer in adult neurons with a lentivirus vector," *J. Virol.*, 71:6641-6649, 1997.

Bodine and Ley, "An enhancer element lies 3' to the human a γ globin gene," *EMBO J.*, 6:2997-3004, 1987.

Boshart et al., "A very strong enhancer is located upstream of an immediate early gene of human cytomegalovirus," *Cell*, 41:521-530, 1985.

Bösze et al., "A transcriptional enhancer with specificity for erythroid cells is located in the long terminal repeat of the friend murine leukemia virus," *EMBO J.*, 5:1615-1623, 1986.

Braddock et al., "HIV-I Tat activates presynthesized RNA in the nucleus," *Cell*, 58:269-279, 1989.

Braselmann et al., "A selective transcriptional induction system for mammalian cells based on Ga14-estrogen receptor fusion proteins," *Proc. Natl. Acad. Sci., USA*, 90:1657-1661, 1993.

Bray et al., "A small element from the Mason-Pfizer monkey virus genome makes human immunodeficiency virus type 1 expression and replication Rev-independent," *Proc. Natl. Acad. Sci. USA*, 91:1256-1260, 1994.

Brown et al., "Efficient polyadenylation within the human immunodeficiency virus type 1 long terminal repeat requires flanking U3-specific sequences," *J. Virol.*, 65:3340-3343, 1991.

(56) References Cited

OTHER PUBLICATIONS

Brown et al., "lac repressor can regulate expression from a hybrid SV40 early promoter containing a lac operator in animal cells," *Cell*, 49:603-612, 1987.
Brummelkamp et al., "A system for stable expression of short interfering RNAs in mammalian cells," *Science*, 296:550-553, 2002.
Bulla and Siddiqui, "The hepatitis B virus enhancer modulates transcription of the hepatitis B virus surface-antigen gene from an internal location," *J. Virol.*, 62:1437-1441, 1988.
Campbell and Villarreal, "Functional analysis of the individual enhancer core sequences of polyomavirus: cell-specific uncoupling of DNA replication from transcription," *Mol. Cell. Biol.*, 8:1993-2004, 1988.
Camper and Tilghman, "Postnatal repression of the α-fetoprotein gene is enhancer independent," *Genes and Dev.*, 3:537-546, 1989.
Campo et al., "Transcriptional control signals in the genome of bovine papilloma virus type 1," *Nature*, 303:77-80, 1983.
Carbonelli et al. "A plasmid vector for isolation of strong promoters in *E. coli*," *FEMS Microbiol Lett*. 177(1):75-82, 1999.
Carmell et al., "Germline transmission of RNAi in mice," *Nat. Struct. Biol.*, 10(2):91-92, 2003.
Case et al., "Stable transduction of quiescent CD34(+)CD38(−) human hematopoietic cells by HIV-1 based lentiviral vectors," *Proc. Natl. Acad. Sci. USA*, 96:2988-2993, 1999.
Celander and Haseltine, "Glucocorticoid Regulation of Murine Leukemia Virus Transcription Elements is Specified by Determinants Within the Viral Enhancer Region," *J. Virology*, 61:269-275, 1987.
Celander et al., "Regulatory Elements Within the Murine Leukemia Virus Enhancer Regions Mediate Glucocorticoid Responsiveness," *J. Virology*, 62:1314-1322, 1988.
Chandler et al., "DNA Sequences Bound Specifically by Glucocorticoid Receptor in vitro Render a Heterlogous Promoter Hormone Responsive in vivo," Cell, 33:489-499, 1983.
Chandler et al., "RNA splicing specificity determined by the coordinated action of RNA recognition motifs in SR proteins," *Proc Natl Acad Sci U S A*. 94(8):3596-3601, 1997.
Chang et al., "Efficacy and safety analyses of a recombinant human immunodeficiency virus type 1 derived vector system," *Gene Therapy*, 6:715-728, 1999.
Chang et al., "Glucose-regulated Protein (GRP94 and GRP78) Genes Share Common Regulatory Domains and are Coordinately Regulated by Common Trans-acting Factors," *Mol. Cell. Biol.*, 9:2153-2162, 1989.
Charneau et al., "A second origin of DNA plus-strand synthesis is required for optimal human immunodeficiency virus replication," *Journal of Virology*, 66:2814-2820, 1992.
Charneau et al., "HIV-1 reverse transcription: a termination step at the center of the genome," *J. Mol. Biol.* 241:651-662, 1994.
Chatterjee et al., "Negative Regulation of the Thyroid-Stimulating Hormone Alpha Gene by Thyroid Hormone: Receptor Interaction Adjacent to the TATA Box," *Proc Natl. Acad Sci. U.S.A.*, 86:9114-9118, 1989.
Chen and Okayama, "High-efficiency transformation of mammalian cells by plasmid DNA," *Mol. Cell. Biol.*, 7:2745-2752, 1987.
Cherrington and Ganem, "Regulation of polyadenylation in human immunodeficiency virus (HIV): contributions of promoter proximity and upstream sequences," *Embo. J.*, 11:1513-1524, 1992.
Chinnasamy et al., "Efficient gene transfer to human peripheral blood monocyte-derived dendritic cells using human immunodeficiency virus type 1-based lentiviral vectors," *Hum. Gene Ther.*, 11(13):1901-9, 2000.
Choi et al., "An altered pattern of cross-resistance in multi-drug-resistant human cells results from spontaneous mutations in the mdr-1 (p-glycoprotein) gene," *Cell*, 53:519-529, 1988.
Christodoulopoulos et al., "Sequences in the Cytoplasmic Tail of the Gibbon Ape Leukemia Virus Envelope Protein that Prevent It's Incorporation into Lentivirus Vectors," *Journal of Virology*, 75(9):4129-4138, 2001.
Clark and Docherty, "Negative regulation of transcription in eukaryotes," *Biochem. J.*, 296:521-541, 1993.

Cocea, "Duplication of a region in the multiple cloning site of a plasmid vector to enhance cloning-mediated addition of restriction sites to a DNA fragment," *Biotechniques*, 23:814-816, 1997.
Cohen et al., "A Repetitive Sequence Element 3' of the Human c-Ha-ras1 Gene Has Enhancer Activity," *J. Cell. Physiol. Suppl.*, 5:75-81, 1987.
Colombatti et al., "Selective killing of target cells by antibody-ricin a chain or antibody-gelonin hybrid molecules: comparison of cytotoxic potency and use in immunoselection procedures," *J. Immunol.*, 131(6):3091-3095, 1983.
Corbeau, et al., "Efficient gene transfer by a human immunodeficiency virus type 1 (HIV-1)-derived vector utilizing a stable HIV packaging cell line," *PNAS U.S.A.*, 93(24):14070-14075, 1996.
Costa et al., "The Cell-Specific Enhancer of the Mouse Transthyretin (Prealbumin) Gene Binds a Common Factor at One Site and a Liver-Specific Factor(s) at Two Other Sites," *Mol. Cell. Biol.*, 8:81-90, 1988.
Cowell, "Repression versus activation in the control of gene transcription," *TIBS*, 19:38-42, 1994.
Cripe et al., "Transcriptional Regulation of the Human Papilloma Virus-16 E6-E7 Promoter by a Keratinocyte-Dependent Enhancer, and by Viral E2 Trans-Activator and Repressor Gene Products: Implications for Cervical Carcinogenesis," *EMBO J.*, 6:3745-3753, 1987.
Culotta and Hamer, "Fine Mapping of a Mouse Metallothionein Gene Metal-Response Element," *Mol. Cell. Biol.*, 9:1376-1380, 1989.
Cultraro et al., "Function of the c-Myc antagonist Mad1 during a molecular switch from proliferation to differentiation," *Mol. Cell. Biol.*, 17(5):2353-2359, 1997.
Czauderna et al., "Inducible shRNA expresion for application in a prostate cancer mouse model," *Nucleic Acids Research*, 31 (2):e127, 2003.
Dandolo et al., "Regulation of Polyoma Virus Transcription in Murine Embryonal Carcinoma Cells," *J. Virology*, 47:55-64, 1983.
Dao et al., "Adhesion to fibronectin maintains regenerative capacity during ex vivo, culture and transduction of human hematopoietic stem and progenitor cells," *Blood*, 92:4612-4621, 1998.
Dao et al., "FLT3 ligand preserves the ability of human CD34+ progenitors to sustain long-term hematopoiesis in immune-deficient mice after ex vivo retroviral-mediated transduction," *Blood*, 89:446-456, 1997.
Dardalhon et al., "Lentivirus-mediated gene transfer in primary T cells is enhanced by a central DNA flap," *Gene Therapy*, 8: 190-198, 2001.
Das et al., "A conserved hairpin motif in the R-U5 region of the human immunodeficiency virus type 1 RNA genome is essential for replication," *J. Virol.* 71:2346-2356, 1997.
De Villiers et al., "Polyoma Virus DNA Replication Requires an Enhancer," *Nature*, 312:242-246, 1984.
Deisseroth, "Clinical trials involving multidrug resistance transcription units in retroviral vectors," *Clinical Cancer Research*, 5:1607-1609, 1999.
Deschamps et al., "Identification of a Transcriptional Enhancer Element Upstream From the Proto-Oncogene Fos," *Science*, 230:1174-1177, 1985.
Deuschle et al., "Regulated expression of foreign genes in mammalian cells under the control of coliphage T3 RNA polymerase and lac repressor," *Proc. Natl. Acad. Sci., USA*, 86:5400-5405, 1989.
Deuschle et al., "RNA polymerase II transcription blocked by *Escherichia coli* lac repressor," *Science*, 248:480-483, 1990.
Deuschle et al., "Tetracycline-reversible silencing of eukaryotic promoters," *Mol. Cell. Biol.*, 15(4):1907-1914, 1995.
Devroe and Silver, "Retrovirus-delivered siRNA," *BMC Biotechnol.*, 2(1):15, 2002.
DeZazzo et al., "Involvement of long terminal repeat U3 sequences overlapping the transcription control region in human immunodeficiency virus type 1 mRNA 3' end formation," *Mol. Cell. Biol.*, 11:1624-1630, 1991.
Dingermann et al., "RNA polymerase II catalysed transcription can be regulated in *Saccharomyces cerevisiae* by the bacterial tetracycline repressor—operator system," *EMBO J.*, 11:1487-1492, 1992.
Donello et al., "Woodchuck hepatitis virus contains a tripartite post-transcriptional regulatory element," *J. Virol.*, 72:5085-5092, 1998.

(56) References Cited

OTHER PUBLICATIONS

Donzé and Picard, "RNA interference in mammalian cells using siRNAs synthesized with T7 RNA polymerase," *Nucleic Acids Research*, 30(10):e46, 2002.
Dorrell et al., "Expansion of human cord blood CD34(+)CD38(-31) cells in ex vivo culture during retroviral transduction without a corresponding increase in SCID repopulating cell (SRC) frequency: dissociation of SRC phenotype and function," *Blood*, 95:102-110, 2000.
Dull et al., "A third-generation lentivirus vector with a conditional packaging system," *J. Virology*, 72:8463-8471, 1998.
Edbrooke et al., "Identification of cis-acting sequences responsible for phorbol ester induction of human serum amyloid a gene expression via a nuclear-factor-kappa β-like transcription factor," *Mol. Cell. Biol.*, 9:1908-1916, 1989.
Edlund et al., "Cell-specific expression of the rat insulin gene: evidence for role of two distinct 5' flanking elements," *Science*, 230:912-916, 1985.
Eklund et al., "PU.1, interferon regulatory factor 1, and interferon consensus sequence-binding protein cooperate to increase gp91(phox) expression," *J. Biol. Chem.*, 273(22):13957-65, 1998.
Elbashir et al., "Analysis of gene function in somatic mammalian cells using small interfering RNAs," *Methods*, 26:199-213, 2002.
Elbashir et al., "Functional anatomy of siRNAs for mediating efficient RNAi in *Drosophila melanogaster* embryo lysate," *The EMBO Journal*, 20(23):6877-6888, 2001.
Elbashir, "Duplexes of 21-nucleotide RNAs mediate RNA interference in cultured mammalian cells," *Nature*, 411:494-498, 2001.
Epstein et al., "Tumor-specific PAX3-FKHR transcription factor, but not PAX3, activates the platelet-derived growth factor alpha receptor," *Mol. Cell. Biol.*, 18(7):4118-4130, 1998.
Fassler, "Lentiviral transgene vectors: Green light for efficient production of transgenic farm animals," *EMBO Reports*, 5:28-29, 2004.
Fechheimer et al., "Transfection of mammalian cells with plasmid DNA by scrape loading and sonication loading," *Proc Nat'l. Acad. Sci. USA* 84:8463-8467, 1987.
Feng and Holland, "HIV-I Tat Trans-Activation Requires the Loop Sequence Within Tar," *Nature*, 334(6178):165-167, 1988.
Figge et al., "Stringent regulation of stably integrated chloramphenicl acetyl transferase genes by *E. coli* Iac repressor in monkey cells," *Cell*, 52:713-722, 1988.
Firak and Subramanian, "Minimal Transcription Enhancer of Simian Virus 40 is a 74-Base-Pair Sequence that Has Interacting Domains," *Mol. Cell. Biol.*, 6:3667-3676, 1986.
Foecking and Hofstetter, "Powerful and Versatile Enhancer-Promoter Unit for Mammalian Expression Vectors," *Gene*, 45(1):101-105, 1986.
Friedman et al., "KAP-1, a novel corepressor for the highly conserved KRAB repression domain," *Genes Dev.*, 10:2067-2078, 1996.
Froehler et al., "Synthesis of DNA via deoxynucleoside H-phosphonate intermediates." *Nuc. Acids Res.* 14:5399-5407, 1986.
Fuerst et al., "Transfer of the inducible lac repressor/operator system from *Echerichia coli* to a vaccinia virus expression vector," *Proc. Natl. Acad. Sci., USA*, 86:2549-2553, 1989.
Fujita et al., "Interferon-β Gene Regulation: Tandemly Repeated Sequences of a Synthetic 6-bp Oligomer Function as a Virus-Inducible Enhancer," *Cell*, 49:357-367, 1987.
Fussenegger et al., "Streptogramin-based gene regulation systems for mammalian cells," *Nat. Biotech.*, 18:1203-1208, 2000.
Gatz et al., "Stringent repression and homogeneous de-repression by tetracycline of a modified CaMV 35S promoter in intact transgenic tobacco plants," *Plant J.*, 2:397-404, 1992.
GenBank Accession No. AF105229, "Cloning vector pHR'-CMVLacZ," 1996.
GenBank Accession No. M66390, "Human GP91-PHOX gene promoter region," 1991.
GenBank Accession No. M82856, "Human myelomonocytic leukocyte integrin CD11b (Mac-1) gene, 5' flank," 1992.
GenBank Accession No. NM_000397, "*Homo sapiens* cytochrome b-245, beta polypeptide (CYBB), mRNA," 1986.
Gilles et al., "A tissue-specific transcription enhancer element is located in the major intron of a rearranged immunoglobulin heavy-chain gene," *Cell*, 33:717-728, 1983.
Gilmartin et al., "Activation of HIV-1 pre-mRNA 3' processing in vitro requires both an upstream element and TAR," *EMBO. J.*, 11:4419-4428, 1992.
Ginsberg et al., "Up-regulation of MET but not neural cell adhesion molecule expression by the PAX3-FKHR fusion protein in alveolar rhabdomyosarcoma," *Cancer Res.*, 58:3542-3546, 1998.
Gloss et al., "The Upstream Regulatory Region of the Human Papilloma Virus-16 Contains an E2 Protein-Independent Enhancer Which is Specific for Cervical Carcinoma Cells and Regulated by Glucocorticoid Hormones," *EMBO J.*, 6:3735-3743, 1987.
Godbout et al., "Fine-Structure Mapping of the Three Mouse Alpha-Fetoprotein Gene Enhancers," *Mol. Cell. Biol.*, 8:1169-1178, 1988.
Goodbourn and Maniatis, "Overlapping Positive and Negative Regulatory Domains of the Human β-Interferon Gene," *Proc. Natl. Acad. Sci. USA*, 85:1447-1451, 1988.
Goodbourn et al., "The Human Beta-Interferon Gene Enhancer is Under Negative Control," *Cell*, 45:601-610, 1986.
Gopal, "Gene transfer method for transient gene expression, stable transformation, and cotransformation of suspension cell cultures," *Mol. Cell. Biol.* 5:1188-1190, 1985.
Gossen and Bujard, "Tight control of gene expression in mammalian cells by tetracycline-responsive promoters," *Proc. Natl. Acad. Sci.*, 89:5547-5551, 1992.
Gossen et al., "Transcriptional activation by tetracyclines in mammalian cells," *Science*, 268:1766-1769, 1995.
Graham and Van Der Eb, "A new technique for the assay of infectivity of human adenovirus 5 DNA," *Virology*, 52:456-467, 1973.
Greco and Dachs, "Gene directed enzyme/prodrug therapy of cancer: historical appraisal and future prospectives," *J. Cell. Phys.*, 187: 22-36, 2001.
Greene et al., "HIV-1, and Normal T-Cell Growth: Transcriptional Strategies and Surprises," *Immunology Today*, 10:272-278, 1989.
Grosschedl and Baltimore, "Cell-Type Specificity of Immunoglobulin Gene Expression is Regulated by at Least Three DNA Sequence Elements," *Cell*, 41:885-897, 1985.
Gupta et al., "Mmip1: a novel leucine zipper protein that reverses the suppressive effects of Mad family members on c-myc," *Oncogene*, 16:1149-1159, 1998.
Haslinger and Karin, "Upstream Promoter Element of the Human Metallothionein-II Gene Can Act Like an Enhancer Element," *Proc Natl. Acad. Sci. U.S.A.*, 82:8572-8576, 1985.
Hasuwa et al., "Small interfering RNA and gene silencing in transgenic mice and rats," *FEBS Letters*, 532:227-230, 2002.
Hauber and Cullen, "Mutational Analysis of the Trans-Activation-Responsive Region of the Human Immunodeficiency Virus Type I Long Terminal Repeat," *J. Virology*, 62:673-679, 1988.
Hen et al., "A Mutated Polyoma Virus Enhancer Which is Active in Undifferentiated Embryonal Carcinoma Cells is not Repressed by Adenovirus-2 E1A Products," *Nature*, 321:249-251, 1986.
Hennighausen et al., "Conditional gene expression insecretory tissues and skin of tetracycline responsive system," *J. Cell. Biochem.*, 59:463-472, 1995.
Hensel et al., "PMA-Responsive 5' Flanking Sequences of the Human TNF Gene," *Lymphokine Res.*, 8:347-351, 1989.
Herr and Clarke, "The SV40 Enhancer is Composed of Multiple Functional Elements That Can Compensate for One Another," *Cell*, 45:461-470, 1986.
Hickstein et al., "Identification of the promoter of the myelomonocytic leukocyte integrin CD11b," *Proc. Natl. Acad. Sci, USA*, 89:2105-2109, 1992.
Hirochika et al., "Enhancers and Trans-Acting E2 Transcriptional Factors of Papilloma Viruses," *J. Virol.*, 61:2599-2606, 1987.
Hirsch et al., "Identification of Positive and Negative Regulatory Elements Governing Cell-Type-Specific Expression of the Neural-Cell-Adhesion-Molecule Gene," *Mol. Cell. Biol.*, 10:1959-1968, 1990.
Holbrook et al., "cis-Acting Transcriptional Regulatory Sequences in the Gibbon Ape Leukemia Virus (GALV) Long Terminal Repeat," *Virology*, 157:211-219, 1987.

(56) References Cited

OTHER PUBLICATIONS

Horlick and Benfield, "The upstream muscle-specific enhancer of the rat muscle creatine kinase gene is composed of multiple elements," *Mol. Cell. Biol.*, 9:2396-2413, 1989.

Hou et al., "Regulatory elements and transcription factors controlling basal and cytokine-induced expression of the gene encoding intercellular adhesion molecule 1," *Proc. Natl. Acad. Sci, USA*, 91:11641-11645, 1994.

Houdebine, "The methods to generate transgenic animals and to control transgene expression," *Journal of Biotechnology*, 98:145-160, 2002.

Hu and Davidson, "The inducible lac operator-repressor system is functional in mammalian cells," *Cell*, 48:555-566, 1987.

Hu et al., "Inhibition of retroviral pathogenesis by RNA interference," *Current Biology*, 12:1301-1311, 2002.

Huang et al., "Glucocorticoid regulation of the ha-musv p21 gene conferred by sequences from mouse mammary tumor virus," *Cell*, 27:245-255, 1981.

Hug et al., "Organization of the Murine Mx Gene and Characterization of its Interferon- and Virus-Inducible Promoter," *Mol. Cell. Biol.*, 8:3065-3079, 1988.

Hwang et al., "Characterization of the S-Phase-Specific Transcription Regulatory Elements in a DNA-Replication-Independent Testis-Specific H2B (TH2B) Histone Gene," *Mol. Cell. Biol.*, 10:585-592, 1990.

Imagawa et al., "Transcription Factor AP-2 Mediates Induction by Two Different Signal-Transduction Pathways: Protein Kinase C and cAMP," *Cell*, 51:251-260, 1987.

Imbra and Karin, "Phorbol Ester Induces the Transcriptional Stimulatory Activity of the SV40 Enhancer," *Nature*, 323:555-558, 1986.

Imler et al., "Negative Regulation Contributes to Tissue Specificity of the Immunoglobulin Heavy-Chain Enhancer," *Mol. Cell. Biol*, 7:2558-2567, 1987.

Imperiale and Nevins, "Adenovirus 5 E2 Transcription Unit: an E1A-Inducible Promoter with an Essential Element that Functions Independently of Position or Orientation," *Mol. Cell. Biol.*, 4:875-882, 1984.

Jakobovits et al., "A Discrete Element 3' of Human Immunodeficiency Virus 1 (HIV-1) and HIV-2 mRNA Initiation Sites Mediates Transcriptional Activation by an HIV Trans-Activator," *Mol. Cell. Biol.*, 8:2555-2561, 1988.

Jameel and Siddiqui, "The Human Hepatitis B Virus Enhancer Requires Transacting Cellular Factor(s) for Activity," *Mol. Cell. Biol.*, 6:710-715, 1986.

Jaynes et al., "The Muscle Creatine Kinase Gene is Regulated by Multiple Upstream Elements, Including a Muscle-Specific Enhancer," *Mol. Cell. Biol.*, 8:62-70, 1988.

Johnson et al., "Muscle creatine kinase sequence elements regulating skeletal and cardiac muscle expression in transgenic mice," *Mol. Cell. Biol.*, 9:3393-3399, 1989.

Juengst, "What next for human gene therapy? Gene transfer often has multiple and unpredictable effects on cells," *BMJ*, 326:1410-11, 2003.

Kadesch and Berg, "Effects of the Position of the Simian Virus 40 Enhancer on Expression of Multiple Transcription Units in a Single Plasmid," *Mol. Cell. Biol.*, 6:2593-2601, 1986.

Kafri et al., "Lentiviral vectors: regulated gene expression," *Molecular Therapy*, 1(6):516-521, 2000.

Kafri et al., "Sustained expression of genes delivered directly into liver and muscle by lentiviral vectors," *Nature Genetics*, 17:314-317, 1997.

Karin et al., "Metal-Responsive Elements Act as Positive Modulators of Human Metallothionein-IIA Enhancer Activity," *Mol. Cell. Biol.*, 7:606-613, 1987.

Katinka et al., "Expression of Polyoma Early Functions in Mouse Embryonal Carcinoma Cells Depends on Sequence Rearrangements in the Beginning of the Late Region," *Cell*, 20:393-399, 1980.

Kawamoto et al., "Identification of the Human Beta-Actin Enhancer and its Binding Factor," *Mol. Cell. Biol.*, 8:267-272, 1988.

Kawasaki and Taira, "Short hairpin type of dsRNAs that are controlled by tRNAval promoter significantly induce RNAi-mediated gene silencing in the cytoplasm of human cells," *Nucleic Acids Research*, 31(2):700-707, 2003.

Kelly et al., "RD114-Pseudotyped oncoretroviral vectors: Biological and physical properties," *Annals of the New York Academy of Sciences*, 938:262-277, 2001.

Khvorova et al., "Functional siRNAs and miRNAs exhibit strand bias," *Cell*, 115:209-216, 2003.

Kiledjian et al., "Identification and characterization of two functional domains within the murine heavy-chain enhancer," *Mol. Cell. Biol.*, 8:145-152, 1988.

Kim et al., "Tetracycline repressor-regulated gene repression in recombinant human cytomegalovirus," *J. Virol.*, 69(4):2565-2573, 1995.

Klages et al., "A stable system for the high-titer production of multiply aattenuated lentiviral vectors," *Mol. Ther*. 2:170-176, 2000.

Klamut et al., "Molecular and Functional Analysis of the Muscle-Specific Promoter Region of the Duchenne Muscular Dystrophy Gene," *Mol. Cell. Biol.*, 10:193-205, 1990.

Klein et al., "High-velocity microprojectiles for delivering nucleic acids into living cells," *Nature*, 327:70-73, 1987.

Koch et al., "Anatomy of a new B-cell-specific enhancer," *Mol. Cell. Biol.*, 9:303-311, 1989.

Kohn et al., "Toward gene therapy for Gaucher disease," *Hum. Gene Ther.*, 2:101-105, 1991.

Kotsopoulou et al., "A Rev-independent human immunodeficiency virus type 1 (HIV-1)-based vector that exploits a codon-optimized HIV-1 gag-pol gene," *J. Virol.*, 74:4839-4852, 2000.

Kramer et al., "Artificial regulatory networks and cascades for discrete multilevel transgene control in mammalian cells," *Biotechnology and Bioengineering*, 83(7):810-20, 2003.

Kraus et al., "Alternative promoter usage and tissue specific expression of the mouse somatostatin receptor 2 gene," *FEBS Lett.*, 428(3):165-170, 1998.

Kriegler and Botchan, "A retrovirus LTR contains a new type of eukaryotic regulatory element," *In: Eukaryotic Viral Vectors*, Gluzman (ed.), Cold Spring Harbor, Cold Spring Harbor Laboratory, NY, 171-180, 1982.

Kriegler et al., "A Novel Form of TNF/Cachectin Is a Cell-Surface Cytotoxix Transmembrane Protein: Ramifications for the Complex Physiology of TNF," *Cell*, 53:45-53, 1988.

Kriegler et al., "Promoter substitution and enhancer augmentation increases the penetrance of the sv40 a gene to levels comparable to that of the harvey murine sarcoma virus ras gene in morphologic transformation," *In: Gene Expression*, Alan Liss (Ed.), Hamer and Rosenberg, New York, 107-124, 1983.

Kriegler et al., "Viral Integration and Early Gene Expression Both Affect the Efficiency of SV40 Transformation of Murine Cells: Biochemical and Biological Characterization of an SV40 Retrovirus," *In: Cancer Cells 2/Oncogenes and Viral Genes*, Van de Woude et al. (eds), Cold Spring Harbor, Cold Spring Harbor Laboratory, 345-353, 1984.

Kuhl et al., "Reversible Silencing of Enhancers by Sequences Derived From the Human IFN-alpha Promoter," *Cell*, 50:1057-1069, 1987.

Kunz et al., "Identification of the Promoter Sequences Involved in the Interleukin-6-Dependent Expression of the Rat Alpha-2-Macroglobulin Gene," *Nucl. Acids Res.*, 17:1121-1138, 1989.

Labow et al., "Conversion of the lac repressor into an allosterically regulated transcriptional activator for mammalian cells," *Mol. Cell. Biol.*, 10:3343-3356, 1990.

Laherty et al., "Histone deacetylases associated with the mSin3 corepressor mediate Mad transcriptional repression," *Cell*, 89:349-356, 1997.

Lam and Thummel, "Inducible expression of double-stranded RNA directs specific genetic interfeence in *Drosophila*," *Current Biology*, 10:957-963, 2000.

Lareyre et al., "A 5-kilobase pair promoter fragment of the murine epididymal retinoic acid-binding protein gene drives the tissue-specific, cell-specific, and androgen-regulated expression of a foreign gene in the epididymis of transgenic mice," *J Biol Chem.*, 274(12):8282-8290, 1999.

(56) References Cited

OTHER PUBLICATIONS

Larsen et al., "Repression mediates cell-type-specific expression of the rat growth hormone gene," *Proc Natl. Acad. Sci. USA.*, 83:8283-8287, 1986.
Larsson et al., "Analysis of the DNA-binding activities of Myc/Max/Mad network complexes during induced differentiation of U-937 monoblasts and F9 teratocarcinoma cells," *Oncogene*, 15:737-748, 1997.
Laspia et al., "HIV-1 Tat protein increases transcriptional initiation and stabilizes elongation," *Cell*, 59:283-292, 1989.
Latimer et al., "Highly conserved upstream regions of the alpha..sub.1-antitrypsin gene in two mouse species govern liver-specific expression by different mechanisms," *Mol. Cell. Biol.*, 10:760-769, 1990.
Lee et al., "Activation of beta3-adrenoceptors by exogenous dopamine to lower glucose uptake into rat adipocytes," *J Auton Nerv Syst.* 74(2-3):86-90, 1997.
Lee et al., "Glucocorticoids Regulate Expression of Dihydrofolate Reductase cDNA in Mouse Mammary Tumor Virus Chimaeric Plasmids," *Nature*, 294:228-232, 1981.
Levenson et al., "Internal ribosomal entry site-containing retroviral vectors with green fluorescent protein and drug resistance markers," *Human Gene Therapy*, 9:1233-1236, 1998.
Levinson et al., "Activation of SV40 Genome by 72-Base-Pair Tandem Repeats of Moloney Sarcoma Virus," *Nature*, 295:568-572, 1982.
Lewis and Emerman, "Passage through mitosis is required for oncoretroviruses but not for the human immunodeficiency virus," *J. Virology*, 68:510-516, 1994.
Lien et al., "Regulation of the myeloid-cell-expressed human gp91-phox gene as studied by transfer of yeast artificial chromosome clones into embryonic stem cells: Suppression of a variegated cellular patteron of expression requires a full complement of distant cis element," *Molecular and Cellular Biology*, 17(4):2279-2290, 1997.
Lin et al., "Delineation of an enhancerlike positive regulatory element in the interleukin-2 receptor .alpha.-chain gene," *Mol. Cell. Biol.*, 10:850-853, 1990.
Liu et al., "Suppression of growth and transformation and induction of apoptosis by EGR-1," *Cancer Gene Ther.*, 5:3-28, 1998.
Lois et al., "Germline transmission and tissue-specific expression of transgenes delivered by lentiviral vectors," *Science*, 295-868-872, 2002.
Loubiere et al., "The equine herpes virus 4 thymidine kinase is a better suicide gene than the human herpes virus 1 thymidine kinase," *Gene Ther.* 6(9):1638-1642, 1999.
Luo and Skalnik, "CCAAT displacement protein competes with multiple transcriptional activators for binding to four sites in the proximal gp91$^{phox}$ promoter," *J. Biol. Chem.*, 271:18203-18210, 1996.
Luo and Skalnik, "Interferon regulatory factor-2 directs transcription from the gp91$^{phox}$ promoter," *J. Biol. Chem.*, 271:2345-2351, 1996.
Luria et al., "Promoter Enhancer Elements in the Rearranged Alpha-Chain Gene of the Human T-Cell Receptor," *EMBO J.*, 6:3307-3312, 1987.
Lusky and Botchan, "Transient Replication of Bovine Papilloma Virus Type 1 Plasmids: cis and trans Requirements," *Proc Natl. Acad. Sci. U.S.A.*, 83:3609-3613, 1986.
Lusky et al., "Bovine Papilloma Virus Contains an Activator of Gene Expression at the Distal End of the Early Transcription Unit," *Mol. Cell. Biol.* 3:1108-1122, 1983.
Majors and Varmus, "A Small Region of the Mouse Mammary Tumor Virus Long Terminal Repeat Confers Glucocorticoid Hormone Regulation on a Linked Heterologous Gene," *Proc. Natl. Acad. Sci. U.S.A.*, 80:5866-5870, 1983.
Malik et al., "Retroviral-mediated gene expression in human myelomonocyti a comparison of hematopoietic cell promoters to viral promote," *Blood*, 86:2993-3005, 1995.
Mallory et al., "A viral suppressor of RNA silencing differentially regulates the accumulation of short interfering RNAs and microRNAs in tobacco," *Proc. Natl. Acad. Sci., USA* 99(23):15228-15233, 2002.

Mangeot et al., "Development of minimal lentivirus derived from simian immunodeficiency virus (SIVmac251) and their use for gene transfer into human dendritic cells," *Jour. Vir.*, 74:8307-8315, 2000.
Margolin et al., "Krüppel-associated boxes are potent transcriptional repression domains," *Proc. Natl. Acad. Sci., USA*, 91:4509-4513, 1994.
Marthas et al. "Viral determinants of simian immunodeficiency virus (SIV) virulence in *Rhesus macaques* assessed by using attenuated and pathogenic molecular clones of SIVmac," *J. Virol.*, 67:6047-6055, 1993.
Matsukura et al., "Establishment of conditional vectors for hairpin siRNA knockdowns," *Nucleic Acids Research*, 31:e77, 2003.
May et al., "Therapeutic haemoglobin synthesis in beta-thalassaemic mice expressing lentivirus-encoded human beta-globin," *Nature*, 406(6791):82-86, 2000.
Mazurier et al., "Rapid analysis and efficient selection of human transduced primitive hematopoietic cells using the humanized S65T green fluorescent protein," *Gene Ther.*, 5:556-562, 1998.
McManus and Sharp, "Gene silencing in mammals by small interfering RNA's," *Nature Reviews*, 3:737-747, 2002.
McNeall et al., "Hyperinducible Gene Expression From a Metallotionein Promoter Containing Additional Metal-Responsive Elements," *Gene*, 76:81-88, 1989.
Mhashilkar et al., "Intrabody-mediated phenotypic knockout of major histocompatibility complex class I expression in human and monkey cell lines and in primary human keratinocytes," *Gene Ther.*, 9(5):307-319, 2002.
Miksicek et al., "Glucocorticoid Responsiveness of the Transcriptional Enhancer of Moloney Murine Sarcoma Virus," *Cell*, 46:283-290, 1986.
Miyagishi and Taira, "U6 promoter-driven siRNAs with four uridine 3' overhangs efficiently suppress targeted gene expression in mammalian cells," *Nature Biotechnology*, 19:497-500, 2002.
Miyoshi et al., "Transduction of human CD34+ cells that mediate long-term engraftment of NOD/SCID mice by HIV vectors," *Science*, 283:682-686, 1999.
Mizushima and Nagata, "pEF-BOS, a powerful mammalian expression vector," *Nucleic Acids Res.*, 18:5322, 1990.
Moosmann et al., "Silencing of RNA polymerases II and III-dependent transcription by the KRAB protein domain of KOX1, a Krüppel-type zinc finger factor," *Biol. Chem.*, 378:669-677, 1997.
Mordacq and Linzer, "Co-localization of Elements Required for Phorbol Ester Stimulation and Glucocorticoid Repression of Proliferin Gene Expression," *Genes and Dev.*, 3:760-769, 1989.
Moreau et al., "The SV40 base-repair repeat has a striking effect on gene expression both in sv40 and other chimeric recombinants," *Nucl. Acids Res.*, 9:6047-6068, 1981.
Muesing et al., "Regulation of mRNA accumulation by a human immunodeficiency virus trans-activator protein," *Cell*, 48:691-701, 1987.
Naldini et al., "Efficient transfer, integration, and sustained long-term expression of the transgene in adult rat brains injected with a lentiviral vector," *Proc. Natl. Acad. Sci. USA*, 93:11382-11388, 1996.
Naldini et al., "In vivo gene delivery and stable transduction of nondividing cells by a lentiviral vector," *Science*, 272:263-267, 1996.
Naldini, "Lentiviruses as gene transfer agents for delivery to non-dividing cells," *Current Opinion in Biotechnology*, 9:457-463, 1998.
Negre et al., "Characterization of novel safe lentiviral vectors derived from simian immunodeficiency virus (SIVmac251) that efficiently transduce mature human dendritic cells," *Gene Therapy*, 7(19):1613-1623, 2000.
Negre et al., "Lentiviral vectors derived from simian immunodeficiency virus," *Current Topics in Microbiology and Immunology*, 261:53-74, 2001.
Ng et al., "Regulation of the Human Beta-Actin Promoter by Upstream and Intron Domains," *Nuc. Acids Res.*, 17:601-615, 1989.
Nomoto et al., "Cloning and characterization of the alternative promoter regions of the human LIMK2 gene responsible for alternative transcripts with tissue-specific expression," *Gene*, 236(2):259-271, 1999.
Notice of Allowance issued in U.S. Appl. No. 12/537,789, dated Jun. 28, 2012.

(56) References Cited

OTHER PUBLICATIONS

Office Communication issued in Canadian Patent Application No. 2,456,169, dated Oct. 13, 2010.
Office Communication issued in Canadian Patent Application No. 2,462,628, dated Nov. 18, 2010.
Office Communication issued in Canadian Patent Application No. 2,462,628, dated Oct. 21, 2009.
Office Communication issued in Canadian Patent Application No. 2,462,628, dated Dec. 14, 2011.
Office Communication issued in Canadian Patent Application No. 2,456,169, dated Sep. 15, 2009.
Office Communication issued in Chinese Patent Application No. 02824127.4, dated Jul. 24, 2009. (English translation).
Office Communication issued in Chinese Patent Application No. 02824127.4, dated Feb. 10, 2006. (English translation).
Office Communication issued in European Patent Application No. 02763401.3, dated Apr. 3, 2006. (English translation).
Office Communication issued in European Patent Application No. 02763401.3, dated Feb. 6, 2008.
Office Communication issued in European Patent Application No. 02763401.3, dated Aug. 27, 2009.
Office Communication issued in European Patent Application No. 02780402.0, dated Mar. 16, 2009.
Office Communication issued in European Patent Application No. 02780402.0, dated Mar. 3, 2006.
Office Communication issued in European Patent Application No. 02780402.0, dated Oct. 10, 2006.
Office Communication issued in European Patent Application No. 02780402.0, dated Dec. 13, 2007.
Office Communication issued in Japanese Patent Application No. 2003-532630, dated Oct. 28, 2008. (English translation).
Office Communication issued in Japanese Patent Application No. 2003-532630, dated Aug. 4, 2009. (English translation).
Office Communication issued in Korean Patent Application No. 10-2004-7004973, dated Sep. 16, 2009. (English translation).
Office Communication issued in New Zealand Patent Application No. 532060, dated May 14, 2004.
Office Communication issued in Russian Patent Application No. 2004113452, dated Sep. 13, 2006. (English translation).
Office Communication issued in U.S. Appl. No. 10/209,952, dated Mar. 31, 2005.
Office Communication issued in U.S. Appl. No. 10/209,952, dated Aug. 4, 2005.
Office Communication issued in U.S. Appl. No. 10/209,952, dated Aug. 11, 2006.
Office Communication issued in U.S. Appl. No. 10/209,952, dated Aug. 7, 2007.
Office Communication issued in U.S. Appl. No. 10/209,952, dated Feb. 25, 2008.
Office Communication issued in U.S. Appl. No. 10/209,952, dated Sep. 26, 2008.
Office Communication issued in U.S. Appl. No. 10/209,952, dated Jun. 2, 2009.
Office Communication issued in U.S. Appl. No. 12/537,789, dated Apr. 2, 2012.
Office Communication issued in U.S. Appl. No. 12/578,346, dated Mar. 26, 2010.
Office Communication issued in U.S. Appl. No. 12/578,346, dated Aug. 5, 2010.
Office Communication issued in U.S. Appl. No. 12/578,346, dated Dec. 27, 2010.
Office Communication issued in U.S. Appl. No. 12/578,346, dated Apr. 3, 2012.
Office Communication issued in U.S. Appl. No. 11/680,414, dated Aug. 21, 2009.
Office Communication issued in U.S. Appl. No. 11/680,414, dated Nov. 15, 2011.
Office Communication issued in U.S. Appl. No. 11/680,414, dated May 9, 2011.
Office Communication issued in U.S. Appl. No. 11/680,414, dated Dec. 1, 2010.
Office Communication issued in U.S. Appl. No. 11/680,414, dated Nov. 9, 2010.
Office Communication issued in U.S. Appl. No. 11/680,414, dated Mar. 19, 2010.
Office Communication issued in U.S. Appl. No. 11/680,414, dated Dec. 30, 2009.
Office Communication issued in U.S. Appl. No. 10/261,078, dated Aug. 24, 2005.
Office Communication issued in U.S. Appl. No. 10/261,078, dated May 3, 2005.
Office Communication issued in U.S. Appl. No. 10/261,078, dated Jun. 2, 2006.
Office Communication issued in U.S. Appl. No. 10/261,078, dated Oct. 19, 2006.
Office Communication, issued in U.S. Appl. No. 10/010,081, dated Feb. 27, 2004.
Office Communication, issued in U.S. Appl. No. 10/010,081, dated Jun. 18, 2004.
Office Communication, issued in U.S. Appl. No. 10/010,081, dated Dec. 8, 2004.
Office Communication, issued in U.S. Appl. No. 10/010,081, dated Mar. 24, 2005.
Office Communication, issued in U.S. Appl. No. 10/010,081, dated Dec. 1, 2005.
Office Communication, issued in U.S. Appl. No. 10/010,081, dated Oct. 19, 2006.
Office Communication, issued in U.S. Appl. No. 10/010,081, dated Nov. 14, 2006.
Office Communication, issued in U.S. Appl. No. 10/010,081, dated Apr. 29, 2009.
Ohkawa and Taira, "Control of the functional activity of an antisense RNA by a tetracycline-responsive derivative of the human U6 snRNA promoter," *Human Gene Therapy*, 11:577-585, 2000.
Oligino et al., "Drug inducible transgene expression in brain using a herpes simplex virus vector," *Gene Ther.*, 5:491-496, 1998.
Ondek et al., "Discrete Elements Within the SV40 Enhancer Region Display Different Cell-Specific Enhancer Activities," *EMBO J.*, 6:1017-1025, 1987.
Ornitz et al., "Promoter and enhancer elements from the rat elastase i gene function independently of each other and of heterologous enhancers," *Mol. Cell. Biol.* 7:3466-3472, 1987.
Ory et al., "A stable human-derived packaging cell line for production of high titer retrovirus/vesicular stomatitis virus G pseudotypes," *Proc. Natl. Acad. Sci.*, 93:11400-11406, 1996.
Pahl et al., "Characterization of the myeloid-specific CD11b promoter," *Blood*, 79:865-870, 1992.
Palmiter et al., "Differential regulation of metallothionein-thymidine kinase fusion genes in transgenic mice and their offspring," *Cell*, 29:701-710, 1982.
Paule and White, "Trancription by RNA polymerases I and III," *Nucleic Acids Research*, 28:1283-1298, 2000.
PCT International Preliminary Examination Report issued in International Application No. PCT/US02/24275, dated Sep. 20, 2005.
PCT International Preliminary Examination Report issued in International Application No. PCT/US02/31023, dated Oct. 20, 2003.
PCT International Search Report issued in International Application No. PCT/US02/24275, dated Sep. 9, 2003.
PCT International Search Report issued in International Application No. PCT/US02/31023, dated Jul. 28, 2003.
PCT Invitation to Pay Additional Fees issued in International Application No. PCT/US02/24275, dated Jun. 11, 2003.
PCT Invitation to Restrict or Pay Additional Fees issued in International Application No. PCT/US02/24275, dated Mar. 3, 2004.
PCT Written Opinion issued in International Application No. PCT/US02/24275, dated Jul. 21, 2004.
PCT Written Opinion issued in International Application No. PCT/US02/24275, dated Oct. 12, 2004.
Pech et al., "Functional identification of regulatory elements within the promoter region of platelet-derived growth factor 2," *Mol. Cell. Biol.*, 9(2):396-405, 1989.

(56) References Cited

OTHER PUBLICATIONS

Pengue et al., "Repression of transcriptional activity at a distance by the evolutionary conserved KRAB domain present in a subfamily of zinc finger proteins," *Nucleic Acids Research*, 22(15):2908-2914, 1994.
Perez-Stable and Constantini, "Roles of fetal Gγ-globin promoter elements and the adult β-globin 3' enhancer in the stage-specific expression of globin genes," *Mol. Cell. Biol.*, 10:1116-1125, 1990.
Pfeifer et al., "Gene Therapy: Promises and Problems," *Annu. Rev. Hum. Genet.*, 2:177-211, 2001.
Piacibello et al., "Engraftment in nonobese diabetic severe combined immunodeficient mice of human CD34(+) cord blood cells after ex vivo expansion: evidence for the amplification and self-renewal of repopulating stem cells," *Blood*, 93:3736-3749, 1999.
Picard and Schaffner, "A Lymphocyte-Specific Enhancer in the Mouse Immunoglobulin Kappa Gene," *Nature*, 307:80-82, 1984.
Pinkert et al., "An albumin enhancer located 10 kb upstream functions along with its promoter to direct efficient, liver-specific expression in transgenic mice," *Genes and Dev.*, 1:268-276, 1987.
Ponta et al., "Hormonal Response Region in the Mouse Mammary Tumor Virus Long Terminal Repeat Can Be Dissociated From the Proviral Promoter and Has Enhancer Properties," *Proc. Natl. Acad. Sci. U.S.A.*, 82:1020-1024, 1985.
Porton et al., "Immunoglobulin heavy-chain enhancer is required to maintain transfected .gamma.2a gene expression in a pre-b-cell line," *Mol. Cell. Biol.*, 10:1076-1083, 1990.
Potter et al., "Enhancer-dependent expression of human k immunoglobulin genes introduced into mouse pre-B lymphocytes by electroporation," *Proc Nat'l Acad. Sci. USA*, 81:7161-7165, 1984.
Queen and Baltimore, "Immunoglobulin Gene Transcription is Activated by Downstream Sequence Elements," *Cell*, 35:741-748, 1983.
Quéva et al., "Sequential expression of the MAD family of transcriptional repressors during differentiation and development," *Oncogene*, 16:967-977, 1998.
Quinn et al., "Multiple components are required for sequence recognition of the ap1 site in the gibbon ape leukemia virus enhancer," *Mol. Cell. Biol.*, 9:4713-4721, 1989.
Ramezani et al., "Lentiviral vectors for enhanced gene expression in human hematopoietic cells," *Molecular Therapy*, 2:458-469, 2000.
Ready et al., "Ricin-like plant toxins are evolutionarily related to single-chain ribosome-inhibiting proteins from *Phytolacca*," *J. Biol. Chem.*, 259(24):15252-15256, 1984.
Redondo et al., "A T-Cell-Specific Transcriptional Enhancer Within the Human T-Cell Receptor .delta. Locus," *Science*, 247:1225-1229, 1990.
Reisman and Rotter, "Induced Expression From the Moloney Murine Leukemia Virus Long Terminal Repeat During Differentiation of Human Myeloid Cells is Mediated Through its Transcriptional Enhancer," *Mol. Cell. Biol.*, 9:3571-3575, 1989.
Remington's Pharmaceutical Sciences, 15th Ed., pp. 1035-1038 and 1570-1580, 1975.
Resendez Jr., et al., "Identification of highly conserved regulatory domains and protein-binding sites in the promoters of the rat and human genes encoding the stress-inducible 78-kilodalton glucose-regulated protein," *Mol. Cell. Biol.*, 8:4579-4584, 1988.
Rippe et al., "DNA-mediated gene transfer into adult rat hepatocytes in primary culture," *Mol. Cell Biol.*, 10:689-695, 1990.
Rippe et al., "Regulatory elements in the 5' flanking region and the first intron contribute to transcriptional control of the mouse alpha-1-type collagen gene," *Mol. Cell. Biol.*, 9:2224-2227, 1989.
Riffling et al., "AP-1/jun-binding Sites Mediate Serum Inducibility of the Human Vimentin Promoter," *Nuc. Acids Res.*, 17:1619-1633, 1989.
Roe et al., "Integration of murine leukemia virus DNA depends on mitosis," *Embo. J.*, 12:2099-2108, 1993.
Rosen et al., "The location of cis-acting regulatory sequences in the human t-cell lymphotropic virus type III (HTLV-111/LAV) long terminal repeat," *Cell*, 41:813-823, 1985.

Rubinson et al., "A lentivirus-based system to functionally silence genes in primary mammalian cells, stem cells and transgenic mice by RNA interference," *Nat. Genet.*, 33:401-406, 2003.
Ruzzi et al., "Positive regulation of the β-galactosidase gene from *Kluyveromyces lactis* is mediated by an upstream activation site that shows homology to the GAL upstream activation site of *Saccharomyces cerevisiae*," *Mol. Cell. Biol.*, 7(3):991-997, 1987.
Sakai et al., "Hormone-Mediated Repression: A Negative Glucocorticoid-Response Element From the Bovine Prolactin Gene," *Genes and Dev.*, 2:1144-1154, 1988.
Salmon et al., "A chimeric GALV-derived envelop glycoprotein harboring the cytoplasmic tail of MLV envelope efficiently pseudotypes HIV-1 vectors," *Journal of Gene Medicine*, 2sup:23, 2000.
Salmon et al., "High-level transgene expression in human hematopoietic progenitors and differentia lineages after transduction with improved lentiviral vectors," *Blood*, 96:3392-3398, 2000.
Sambrook et al., *In: Molecular Cloning: A Laboratory Manual 2 rev.ed.*, Cold Spring Harbor, Cold Spring Harbor Laboratory Press, 17.29-17.31, 1.77, 1989.
Sanchez et al., "Selective rescue of early hematopoietic progenitors in Scl -/- mice by-expressing Scl under the control of a stem cell enhancer," *Development*, 128, 4815-4827, 2001.
Sandrin et al., "Letiviral vectors pseudotyped with a modified RD114 envelope glycoprotein show increased stability in sera and augmented transduction of primary lymphocytes and CD34+ cells derived from human and nonhuman primates," *Blood*, 100(3):823-832, 2002.
Satake et al., "Biological activities of oligonucleotides spanning the f9 point mutation within the enhancer region of polyoma virus DNA," *J. Virology*, 62:970-977, 1988.
Schaffner et al., "Redundancy of Information in Enhancers as a Principle of Mammalian Transcription Control," *J. Mol. Biol.*, 201:81-90, 1988.
Scharfmann et al., "Long-term in vivo expression of retrovirus-mediated gene transfer in mouse fibroblast implants," *Proc. Natl. Acad. Sci. USA*, 88:4626-4630, 1991.
Schmid et al., "A rapid method for measuring apoptosis and dual-color immunofluorescence by single laser flow cytometry," *J. Immunol. Methods*, 170:145-157, 1994.
Schramm and Hernandez, "Recruitment of RNA polymerase III to its target promoters," *Gene & Dev.*, 16:2593-2620, 2002.
Schwarz et al., "Asymmetry in the assembly of the RNAi enzyme complex," *Cell*, 15:199-208, 2003.
Scott et al., "Regulation of RNA Polymerase III Transcription during Cell Cycle Entry," *J. Biol. Chem.*, 276:1005-1014, 2001.
Searle et al., "Building a metal-responsive promoter with synthetic regulatory elements," *Mol. Cell. Biol.*, 5:1480-1489, 1985.
Senatore et al., "A variety of RNA polymerases II and III-dependent promoter classes is repressed by factors containing the Krüppel-associated/finger preceding box of zinc finger proteins," *Gene*, 234:381-394, 1999.
Sgouras et al., "ERF: an ETS domain protein with strong transcriptional repressor activity, can suppress ets-associated tumorigenesis and is refulated by phosphorylation during cell cycle and mitogenic stimulation," *EMBO J.*, 14:4781-4793, 1995.
Sharp and Marciniak, "HIV Tar: an RNA Enhancer?" *Cell*, 59:229-230, 1989.
Shaul and Ben-Levy, "Multiple Nuclear Proteins in Liver Cells are Bound to Hepatitis B Virus Enhancer Element and its Upstream Sequences," *EMBO J.*, 6:1913-1920, 1987.
Sherman et al., "Class II Box Consensus Sequences in the HLA-DR. alpha. Gene: Transcriptional Function and Interaction with Nuclear Proteins," *Mol. Cell. Biol.*, 9:50-56, 1989.
Shi et al., "Genetic interference in *Trypanosoma brucei* by heritable and inducible double-stranded RNA," *Cambridge University Press*, 6(7):1069-1076, 2000.
Shinagawa and Ishii, "Generation of Ski-knockdown mice by expression a long double-strand RNA polymerase II promoter," *Genes Devel.*, 17:1340-1345, 2003.

(56) References Cited

OTHER PUBLICATIONS

Sirven et al., "Enhanced transgene expression in cord blood CD34(+)-derived hematopoietic cells, including developing T cells and NOD/SCID mouse repopulating cells, following transduction with modified trip lentiviral vectors," *Molecular Therapy*, 3(4):438-448, 2001.
Sirven et al., "The human immunodeficiency virus type-1 central DNA flap is a crucial determinant for lentiviral vector nuclear import and gene transduction of human hematopoietic stem cells," *Blood*, 96(13):4103-10, 2000.
Sivam et al., "Immunotoxins to a human melanoma-associated antigen: comparison of gelonin with ricin and other a chain conjugates," *Cancer Res.*, 47:3169-3173, 1987.
Skalnik et al., "CCAAT displacement protein as a receptor of the myelomonocytic-specific gp91-ph promoter," *J. Biol. Chem.*, 266:16736-16744, 1991.
Skalnik et al., "Restriction of neuroblastoma to the prostate gland in transgenic mice," *Mol Cell Biol.*, 11:4518-4527, 1991.
Skalnik et al., "Targeting of transgene expression to monocyte/macrophages by the gp91-phox promoter and consequent histiocytic malignancies," *Proc. Natl. Acad. Sci, USA*, 88:8505-8509, 1991.
Sleigh and Lockett, "SV40 Enhancer Activation During Retinoic-Acid-Induced Differentiation of F9 Embryonal Carcinoma Cells," *J. EMBO*, 4:3831-3837, 1985.
Sommer et al., "Identification and characterization of specific DNA-binding complexes containing members of the Myc/Max/Mad network of transcriptional regulators," *J. Biol. Chem.*, 273(12):6632-6642, 1998.
Spalholz et al., "Transactivation of a Bovine Papilloma Virus Transcriptional Regulatory Element by the E2 Gene Product," *Cell*, 42:183-191, 1985.
Spandau and Lee, "Trans-Activation of Viral Enhancers by the Hepatitis B Virus X Protein," *J. Virology*, 62:427-434, 1988.
Spandidos and Wilkie, "Host-Specificities of Papilloma Virus, Moloney Murine Sarcoma Virus and Simian Virus 40 Enhancer Sequences," *EMBO J.*, 2:1193-1199, 1983.
Stephens and Hentschel, "The Bovine Papilloma Virus Genome and its Uses as a Eukaryotic Vector," *Biochem. J.*, 248:1-11, 1987.
Stirpe et al., "Gelonin, a new inhibitor of protein synthesis, nontoxic to intact cells: isolation, characterization, and preparation of cytotoxic complexes with concanavalin A," *J. Biol. Chem.*, 255(14):6947-6953, 1980.
Stitz et al., "Lentiviral Vectors Pseudotyped with Envelope Glycoproteins Derived from Gibbon Ape Leukemia Virus and Murine Leukemia Virus 10A1," *Virology Academic Press*, 273(1):16-20, 2000.
Stuart et al., "Identification of Multiple Metal Regulatory Elements in Mouse Metallothionein-I Promoter by Assaying Synthetic Sequences," *Nature*, 317:828-831, 1985.
Sui et al., "A DNA vector-based RNAi technoloby to suppress gene expression in mammalian cells," *Proc. Natl. Acad. Sci., USA*, 99(8):5515-5520, 2002.
Sullivan and Peterlin, "Transcriptional Enhancers in the HLA-DQ Subregion," *Mol. Cell. Biol.*, 7:3315-3319, 1987.
Supplementary European Search Report issued in European Patent Application No. 02763401.3, dated Oct. 10, 2005.
Sutton et al., "Human immunodeficiency virus type 1 vectors efficiently transduce human hematopoietic stem cells," *J. Virol.*, 72:5781-5788, 1998.
Sutton et al., "Transduction of human progenitor hematopoietic stem cells by human immunodeficiency virus type 1-based vectors is cell cycle dependent," *J. Virol.*, 73:3649-3660, 1999.
Swartzendruber and Lehman, "Neoplastic Differentiation: Interaction of Simian Virus 40 and Polyoma Virus with Murine Teratocarcinoma Cells," *J. Cell. Physiology*, 85:179-188, 1975.
Takebe et al., "SRα Promoter: An Efficient and Versatile Mammalian cDNA Expression System Composed of the Simian Virus 40 Early Promoter and the R-U5 Segment of Human T-Cell Leukemia Virus Type 1 Long Terminal Repeat," *Mol. Cell. Biol.*, 8:466-472, 1988.
Tavernier et al., "Deletion Mapping of the Inducible Promoter of Human IFN-beta Gene," *Nature*, 301:634-636, 1983.
Taylor and Kingston, "E1A Trans-Activation of Human HSP70 Gene Promoter Substitution Mutants is Independent of the Composition of Upstream and TATA Elements," *Mol. Cell. Biol.*, 10:176-183, 1990.
Taylor and Kingston, "Factor Substitution in a Human HSP70 Gene Promoter: TATA-Dependent and TATA-Independent Interactions," *Mol. Cell. Biol.*, 10:165-175, 1990.
Taylor et al., "Stimulation of the Human Heat-Shock Protein 70 Promoter in vitro by Simian Virus 40 Large T Antigen," *J. Biol. Chem.*, 264:16160-16164, 1989.
Thiesen et al., "A DNA Element Responsible for the Different Tissue Specificities of Friend and Moloney Retroviral Enhancers," *J. Virology*, 62:614-618, 1988.
Tiscornia et al., "A general method for gene knockdown in mice by using lentiviral vectors expressing small interfering RNA," *Proc. Natl. Acad. Sci., USA*, 100(4):1844-1848, 2003.
Tronche et al., "Anatomy of the Rat Albumin Promoter," *Mol. Biol. Med.*, 7:173-185, 1990.
Tronche et al., "The Rat Albumin Promoter: Cooperation with Upstream Elements is Required When Binding of APF/HNF 1 to the Proximal Element is Partially Impaired by Mutation or Bacterial Methylation," *Mol. Cell. Biol.*, 9:4759-4766, 1989.
Trono, "Lentiviral vectors: turning a deadly foe into a therapeutic agent," *Gene Ther.*, 7: 20-23, 2000.
Trudel and Constantini, "A 3' Enhancer Contributes to the Stage-Specific Expression of the human Beta-Globin Gene," *Genes and Dev.*, 6:954-961, 1987.
Tsumaki et al., "Modular arrangement of cartilage- and neural tissue-specific cis-elements in the mouse alpha2(XI) collagen promoter," *J Biol Chem.*, 273(36):22861-22864, 1998.
Tur-Kaspa et al., "Use of electroporation to introduce biologically active foreign genes into primary rat hepatocytes," *Mol. Cell Biol.*, 6:716-718, 1986.
Tuschl and Borkhardt, "Small Interfering RNAs: A Revolutionary Tool for the Analysis of Gene Function and Gene Therapy," *Molecular Interventions*, 2:158-167, 2002.
Tyndall et al., "A Region of the Polyoma Virus Genome Between the Replication Origin and Late Protein-Coding Sequences is Required in cis for Both Early Gene Expression and Viral DNA Replication," *Nuc. Acids. Res.*, 9:6231-6250, 1981.
Uchida et al., "HIV, but not murine leukemia virus, vectors mediate high efficiency gene transfer into freshly isolated G0/G1 human hematopoietic stem cells," *Proc. Natl. Acad. Sci. USA*, 95:11939-11944, 1998.
Ueda et al., "Expansion of human NOD/SCID-repopulating cells by stem cell factor, Flk2/Flt3 ligand, thrombopoietin, IL-6, and soluble IL-6 receptor," *J. Clin. Invest.*, 105:1013-1021, 2000.
Unutmaz et al., "Cytokine signals are sufficient for HIV-1 infection of resting human T lymphocytes," *J. Exp. Med.*, 189:1735-1746, 1999.
Valsamakis et al., "Elements upstream of the AAUAAA within the human immunodeficiency virus polyadenylation signal are required for efficient polyadenylation in vitro," *Mol. Cell Biol.*, 12:3699-3705, 1992.
Valsamakis et al., "The human immunodeficiency virus type 1 polyadenylylation signal: a 3' long terminal repeat element upstream of the AAUAAA necessary for efficient polyadenylylation," *Proc. Natl. Acad. Sci. USA*, 88:2108-2112, 1991.
Vannice and Levinson, "Properties of the Human Hepatitis B Virus Enhancer: Position Effects and Cell-Type Nonspecificity," *J. Virology*, 62:1305-1313, 1988.
Vasseur et al., "Isolation and Characterization of Polyoma Virus Mutants Able to Develop in Multipotential Murine Embryonal Carcinoma Cells," *Proc Natl. Acad. Sci. U.S.A.*, 77:1068-1072, 1980.
Wang and Calame, "SV40 enhancer-binding factors are required at the establishment but not the maintenance step of enhancer-dependent transcriptional activation," *Cell*, 47:241-247, 1986.
Watanabe et al., Gene transfection of mouse primordial germ cells in vitro and analysis of their survival and growth control, *Experimental Cell Research*, 230:76-83, 1997.
Weber et al., "An SV40 'Enhancer Trap' Incorporates Exogenous Enhancers or Generates Enhancers From its Own Sequences," *Cell*, 36:983-992, 1984.

(56) References Cited

OTHER PUBLICATIONS

Weber et al., "Conditional human VEGF-mediated vascularization in chicken embryos using a novel temperature-inducible gene regulation (TIGR) system," *Nucleic Acids Research*, 31(12):e69, 2003.
Weber et al., "Macrolide-based transgene control in mammalian cells and mice," *Nat. Biotech.*, 20:901-907, 2002.
Weber et al., "*Streptomyces*-derived quorum-sensing systems engineered for adjustable transgene expression in mammalian cells and mice," *Nucleic Acids Research*, 31(14):e71, 2003.
Weinberger et al., "Localization of a Repressive Sequence Contributing to B-cell Specificity in the Immunoglobulin Heavy-Chain Enhancer," *Mol. Cell. Biol.*, 8:988-992, 1988.
Wiels et al., "A monoclonal antibody directed against a burkitt's lymphoma-associated antigen and its use as carrier for toxins," *IARC Sci. Publ.*, 60:457-464, 1985.
Winoto and Baltimore, "αβ-lineage-specific Expression of the α T-Cell Receptor Gene by Nearby Silencers," *Cell*, 59:649-655, 1989.
Witzgall et al., "The Krüppel-associated box-A (KRAB-A) domain of zinc finger proteins mediates transcriptional repression," *Proc. Natl. Acad. Sci., USA*, 91:4514-4518, 1994.
Wiznerowicz and Trono, "Conditional suppression of cellular genes: lentivirus vector-mediated drug-inducible RNA interference," *Journal of Virology*, 77(16):8957-8961, 2003.
Wu et al., "Development of a novel trans-lentiviral vector that affords predictable safety," *Mol. Ther.* 2:47-55, 2000.
Wu et al., "Promoter-dependent tissue-specific expressive nature of imprinting gene, insulin-like growth factor II, in human tissues," *Biochem Biophys Res Commun*. 233(1):221-226, 1997.
Xia et al., "siRNA-mediated gene silencing in vitro and in vivo," *Nature Biotech.*, 20:1006-1010, 2002.
Yan et al., "Tissue factor transcription driven by Egr-1 is a critical mechanism of murine pulmonary fibrin deposition in hypoxia," *Proc. Natl. Acad. Sci., USA*, 95:8298, 8303, 1998.
Yang et al., "In vivo and in vitro gene transfer to mammalian somatic cells by particle bombardment," *Proc Nat'l Acad Sci. USA*, 87:9568-9572, 1990.
Yu et al., "Prostate-specific targeting using PSA promoter-based lentiviral vectors," *Cancer Gene Therapy*, 8:628-635, 2001.
Yu et al., "RNA interference by expression of short-interfering RNAs and hairpin RNAs in mammalian cells," *Proc. Natl. Acad. Sci., USA*, 99(9):6047-6052, 2002.
Yutzey et al., "An Internal Regulatory Element Controls Troponin I Gene Expression," *Mol. Cell. Biol.*, 9:1397-1405, 1989.
Zennou et al., "HIV-1 genome nuclear import is mediated by a central DNA flap," *Cell*, 101:173-185, 2000.
Zennou et al., "The HIV-1 DNA flap stimulates HIV vector-mediated cell transduction in the brain," *Nature Biotechnology*, 19:446-450, 2001.
Zhu et al., "Use of the Tetracycline-controlled Transcriptional Silencer (tTS) to Eliminate Transgene Leak in Inducible Overexpression Transgenic Mice," *J. Biol. Chem.*, 276:25222-25229, 2001.
Zufferey and Trono, Current Protocols in Neuroscience: unit 4.21: "High-titer production of lentiviral vectors," John Wiley & Sons, New York, 2000, table of contents and manuscript.
Zufferey et al., "Multiply attenuated lentiviral vector achieves efficient gene delivery in vivo," *Nat. Biotechnol.*, 15:871-875, 1997.
Zufferey et al., "Self-inactivating lentivirus vector for safe and efficient in vivo gene delivery," *J. Virol.*, 72:9873-9880, 1998.
Zufferey et al., "Woodchuck hepatitis virus posttranscriptional regulatory element enhances expression of transgenes delivered by retroviral vectors," *J. Virol.*, 73:2886-2892, 1999.
Office Communication issued in Canadian Patent Application No. 2,462,628, dated Sep. 12, 2013.
Office Communication issued in U.S. Appl. No. 13/622,309, dated Mar. 1, 2013.

\* cited by examiner

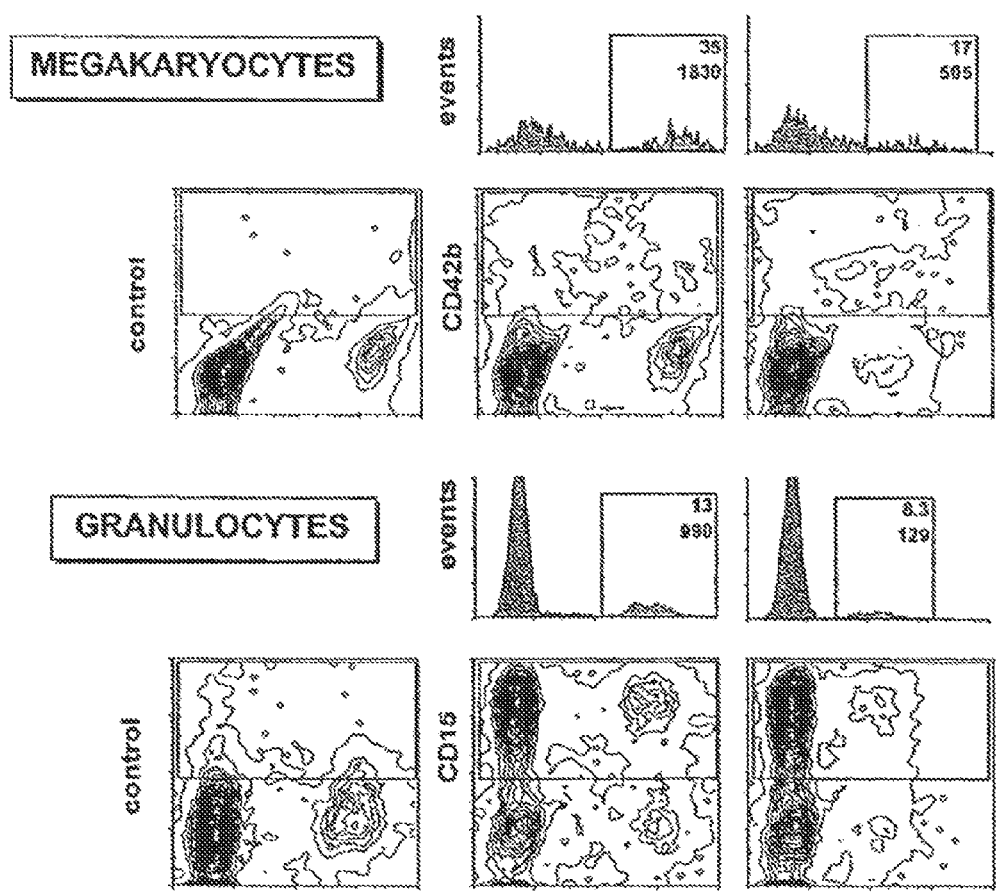
FIG. 3 (cont'd 1)

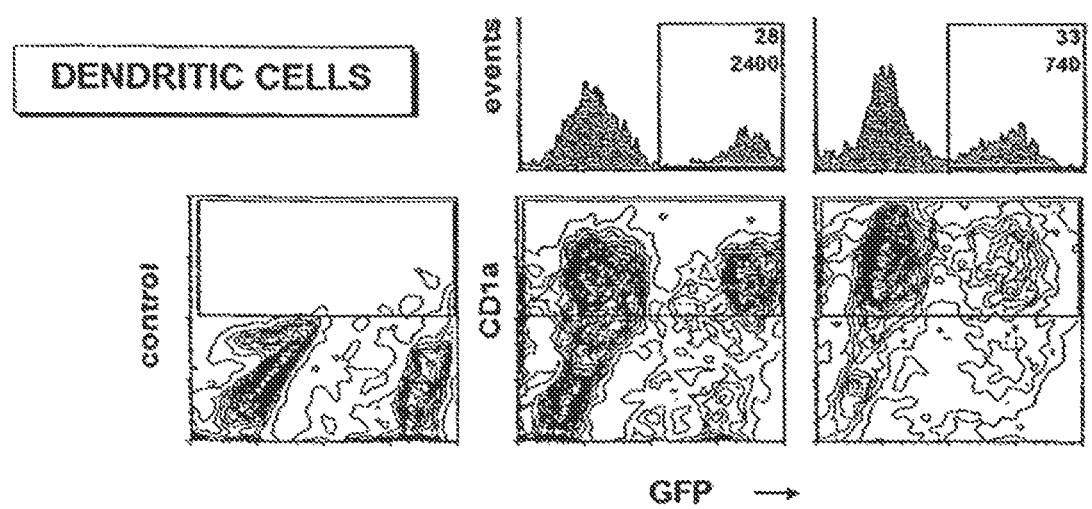
FIG. 3 (cont'd 2)

METHODS AND COMPOSITIONS RELATING TO IMPROVED LENTIVIRAL VECTORS AND THEIR APPLICATIONS

The present application is a continuation of U.S. patent application Ser. No. 13/622,309 filed Sep. 18, 2012, which is a continuation of U.S. patent application Ser. No. 12/537,789 filed Aug. 7, 2009, now U.S. Pat. No. 8,329,462, which is a continuation of U.S. patent application Ser. No. 10/010,081 filed Nov. 9, 2001, now U.S. Pat. No. 7,575,924, which claims the benefit of U.S. Provisional Application Ser. No. 60/248,398 filed on Nov. 13, 2000. The entire contents of each of the above-referenced applications are hereby incorporated by reference.

BACKGROUND OF THE INVENTION

1. Field of the Invention

The present invention relates to improved lentiviral vectors and their use in gene delivery and high level expression of desired transgenes to target cells, particularly to human hematopoietic progenitor cells and differentiated blood lineages.

2. Description of Related Art

Gene therapy via the transduction of human hematopoietic stem cells (hHSC) represents a very promising approach for the treatment of a number of inherited and acquired lympho-hematological disorders. The stable genetic manipulation of long term repopulating hHSC with existing gene delivery systems, however, has been impossible to achieve at an efficiency compatible with therapeutic realities. Oncoretroviral vectors derived from Moloney murine leukemia virus (MLV), for instance, although highly appealing since they integrate their cargo into the chromosomes of target cells, cannot transduce hHSC that have not been first treated with inducers of proliferation (Kohn et al., 1991; Mazurier et al., 1998). Indeed, the nuclear transport of the MLV preintegration complex requires the breakdown of the nuclear envelope that occurs at mitosis (Roe et al., 1993; Lewis and Emerman, 1994). Unfortunately hHSCs, whether harvested from the bone marrow (BM), the umbilical cord (UC) or mobilized in the peripheral circulation, are mostly quiescent and lose their pluripotentiality after stimulation and proliferation (Bhatia et al., 1997; Dao et al., 1997; Dorrell et al., 2000). Recent reports, however, have shown that a significant fraction of pluripotent cells as well as cells capable of long-term engraftment in non-obese diabetic/severe combined immunodeficient (NOD/SCID), also called SCID-repopulating cells (SRC), can be maintained, transduced and even expanded using specific stimulation conditions (Dorrell et al., 2000; Dao et al., 1998; Piacibello et al., 1999; Ueda et al., 2000).

Lentiviruses are a subgroup of retroviruses that can infect nondividing cells owing to the karyophilic properties of their preintegration complex, which allow for its active import through the nucleopore. Correspondingly, lentiviral vectors derived from human immunodeficiency virus type 1 (HIV-1) can mediate the efficient delivery, integration and long-term expression of transgenes into non-mitotic cells both in vitro and in vivo (Naldini et al., 1996a; Naldini et al., 1996b; Blomer et al., 1997). In particular, HIV-based vectors can efficiently transduce human CD34+ hematopoietic cells in the absence of cytokine stimulation (Akkina et al., 1996; Sutton et al., 1998; Uchida et al., 1998; Miyoshi et al., 1999; Case et al., 1999), and these cells are capable of long-term engraftment in NOD/SCID mice (Miyoshi et al., 1999). Furthermore, bone marrow from these primary recipients can repopulate secondary mice with transduced cells, confirming the lentivector-mediated genetic modification of very primitive hematopoietic precursors, most probably bona fide stem cells. Since none of the other currently available gene delivery systems has such an ability, lentiviral vectors provide a previously unexplored basis for the study of hematopoiesis and for the gene therapy of inherited and acquired lympho-hematopoietic disorders via the genetic modification of HSCs.

The demonstration of this important point, however, was provided with an early generation of lentiviral vectors unsuitable for therapeutic applications, either because they failed to meet biosafety requirements (Akkina et al., 1996; Sutton et al., 1998; Uchida et al., 1998) or because they induced levels of transgene expression that were dismissingly low (Miyoshi et al., 1999; Case et al., 1999; An et al., 2000). Accordingly, there is a significant need to develop improved lentiviruses for use as transducing vectors that are capable of effectively transducing hematopoietic cells, particularly hematopoietic progenitor cells, and which are capable of expressing desired transgenes at high levels.

SUMMARY OF THE INVENTION

The present invention is directed to the development of improved lentiviral vectors that both meet biosafety requirements, and which induce high levels of transgene expression. Accordingly, the present invention describes gene transfer vehicles that appear particularly well suited for the transduction of human hematopoietic precursor cells (HPCs) and for the expression of transgenes in differentiated blood lineages. These vectors will facilitate the further use of lentiviral vectors for the genetic manipulation of lympho-hematopoietic cells, and should be particularly useful for both research and therapeutic applications. However, it will be understood by the skilled artisan that the invention is not limited to the transduction of hematopoietic cells and that one may use the lentiviral vectors of the invention for the expression of transgenes in other cell types as well. Some examples of other cell types contemplated include terminally differentiated cells such as neurons, lung cells, muscle cells, liver cells, pancreatic cells, endothelial cells, cardiac cells, skin cells, bone marrow stromal cells, and eye cells. Additionally, stem cells and progenitor cells such as pancreatic ductal cells, neural precursors, and mesodermal stem cells are also contemplated.

The present invention thus concerns, in a general and overall sense, improved vectors that are designed to permit the transfection and transduction of human hematopoietic progenitor cells, or stem cells (hHSC), and provide high level expression of desired transgenes in such cells. The vectors of the present invention may be referred to as self-inactivating lentivectors due to the presence of lentiviral elements as well as certain "self-inactivating" design characteristics that render these vectors safe for human applications.

The lentivectors of the present invention provide, for the first time, an efficient means of achieving high level expression of desired trangenes in hHSCs, cells which have been difficult to transfect and transduce due to the fact that in their unstimulated state, they are relatively resistant to transduction by previous vector systems. These lentivectors have the ability to infect non-dividing cells owing to the karyophilic properties of their preintegration complex, which allow for its active import through the nucleopore. Moreover, preferred lentiviral vectors of the present invention can mediate the efficient delivery, integration and long-term expression of transgenes into non-mitotic cells both in vitro and in vivo, even in the absence of cytokine stimulation. Stem cells transduced by the more preferred lentivectors of the present invention are capable of long-term engraftment, for example, in NOD/SCID mice. Most notably, however, the more preferred lentivectors of the present invention have highly desirable features that permit the high level expression of transgenes in human progenitor cells while meeting human biosafety requirements.

The viral vectors of the present invention, therefore, may be generally described as self-inactivating recombinant vectors that include at least a lentiviral gag, pol and rev genes, that is, those genes required for virus production, which permit their manufacture in reasonable quantities using available producer cell lines. To meet important human safety needs, the more preferred vectors in accordance with the present invention will not include any other active lentiviral genes, such as vpr, vif, vpu, nef, tat, such as where these genes have been removed or otherwise inactivated. In fact, it is preferred that the only active lentiviral genes present in the vector will be the aforementioned gag, pol and rev genes.

The most preferred lentiviral genes and backbone (i.e., long terminal repeats or LTRs) used in preparing lentivectors in accordance with the present invention will be one that is human immunodeficiency virus (HIV) derived, and more particularly, HIV-1 derived. Thus, the gag, pol and rev genes will preferably be HIV genes and more preferably HIV-1 genes. However, the gag, pol and rev genes and LTR regions from other lentiviruses may be employed for certain applications in accordance with the present invention, including the genes and LTRs of HIV-2, simian immunodeficiency virus (SIV), feline immunodeficiency virus, bovine immunodeficiency virus, equine infectious anemia virus, caprine arthritis encephalitis virus and the like. Such constructs could be useful, for example, where one desires to modify certain cells of non-human origin. However, the HIV based vector backbones (i.e., HIV LTR and HIV gag, pol and rev genes) will generally be preferred in connection with most aspects of the present invention in that HIV-based constructs are the most efficient at transduction of human hematopoietic progenitor cells.

The viral vectors of the present invention will also include an expression cassette comprising a transgene positioned under the control of a promoter that is active to promote detectable transcription of the transgene in a human hematopoietic progenitor cell. To determine whether a particular promoter is useful, a selected promoter is tested in the construct in vitro in a selected progenitor cell and, if the promoter is capable of promoting expression of the transgene at a detectable signal-to-noise ratio, it will generally be useful in accordance with the present invention. A desirable signal-to-noise ratio is one between about 10 and about 200, a more desirable signal-to-noise ratio is one 40 and about 200, and an even more desirable signal-to-noise ratio is one between about 150 and about 200. One means of testing such a promoter, described in more detail hereinbelow, is through the use of a signal generating transgene such as the green fluorescent protein (GFP).

Examples of promoters that may be preferably employed in connection with the present invention including an EF1-α, PGK, gp91hox, MHC classII, clotting Factor IX, insulin promoter, PDX1 promoter, CD11, CD4, CD2 or a gp47 promoter. Of these the PGK promoter is preferred, and the EF1-α promoter is particularly preferred. An example of a promoter that is generally not preferred is the CMV promoter, in that this promoter is only minimally active in most progenitor cells. Indeed, it is likely that a CMV promoter will only be useful where one targets human primary B cells or dendritic cells. In any event, however, practice of the present invention is not restricted to the foregoing promoters, so long as the promoter is active in the progenitor, hematopoietic or other cell that one desires to target.

Additionally, the promoters mentioned above can comprise additional elements required for transcription and thus be a part of a transcription cassette. A transcription cassette is defined as comprising one or more promoter elements coupled to enhancers and/or locus control regions, to ensure strong and/or tissue-restricted expression of a transgene.

It is particularly desirable to employ in the lentivectors of the present invention an LTR region that has reduced promoter activity relative to wild-type LTR, in that such constructs provide a "self-inactivating" (SIN) biosafety feature. Self-inactivating vectors are ones in which the production of full-length vector RNA in transduced cells in greatly reduced or abolished altogether. This feature greatly minimizes the risk that replication-competent recombinants (RCRs) will emerge. Furthermore, it reduces the risk that that cellular coding sequences located adjacent to the vector integration site will be aberrantly expressed. Furthermore, an SIN design reduces the possibility of interference between the LTR and the promoter that is driving the expression of the transgene. It is therefore particularly suitable to reveal the full potential of the internal promoter.

Self-inactivation is preferably achieved through in the introduction of a deletion in the U3 region of the 3' LTR of the vector DNA, i.e., the DNA used to produce the vector RNA. Thus, during reverse transcription, this deletion is transferred to the 5' LTR of the proviral DNA. It is desirable to eliminate enough of the U3 sequence to greatly diminish or abolish altogether the transcriptional activity of the LTR, thereby greatly diminishing or abolishing the production of full-length vector RNA in transduced cells. However, it is generally desirable to retain those elements of the LTR that are involved in polyadenylation of the viral RNA, a function spread out over U3, R and U5. Accordingly, it is desirable to eliminate as many of the transcriptionally important motifs from the LTR as possible while sparing the polyadenylation determinants. In the case of HIV based lentivectors, it has been discovered that such vectors tolerate significant U3 deletions, including the removal of the LTR TATA box (e.g., deletions from −418 to −18), without significant reductions in vector titers. These deletions render the LTR region substantially transcriptionally inactive in that the transcriptional ability of the LTR in reduced to about 90% or lower. In preferred embodiments the LTR transcription is reduced to about 95% to 99%. Thus, the LTR may be rendered about 90%, 91%, 92%, 93%, 94%, 95% 96% 97%, 98%, to about 99% transcriptionally inactive.

For certain applications, for example, in the case of promoters that are only modestly active in cells targeted for transduction, one will desire to employ a posttranscriptional regulatory sequence positioned to promote the expression of the transgene. One type of posttranscriptional regulatory sequence is an intron positioned within the expression cassette, which may serve to stimulate gene expression. However, introns placed in such a manner may expose the lentiviral RNA transcript to the normal cellular splicing and processing mechanisms. Thus, in particular embodiments it may be desirable to locate intron-containing transgenes in an orientation opposite to that of the vector genomic transcript.

A more preferred method of enhancing transgene expression is through the use of a posttranscriptional regulatory element which does not rely on splicing events, such as the posttranscriptional processing element of herpes simplex virus, the posttranscriptional regulatory element of the hepatitis B virus (HPRE) or that of the woodchuck hepatitis virus (WPRE), which contains an additional cis-acting element not found in the HPRE. The regulatory element is positioned within the vector so as to be included in the RNA transcript of the transgene, but outside of stop codon of the transgene translational unit. It has been found that the use of such regulatory elements are particularly preferred in the context of modest promoters, but may be contraindicated in the case of very highly efficient promoters.

It is believed that the lentivectors of the present invention may be employed to deliver any transgene that one desires, depending on the application. In the case of delivery to hematopoietic progenitor cells, one will typically select a transgene that will confer a desirable function on such cells, including, for example, globin genes, hematopoietic growth factors, which include erythropoietin (EPO), the interleukins (such as Interleukin-1 (IL-1), Interleukin-2 (IL-2), Interleukin-3 (IL-3), Interleukin-6 (IL-6), Interleukin-12 (IL-12), etc.) and the colony-stimulating factors (such as granulocyte colony-stimulating factor, granulocyte/macrophage colony-stimulating factor, or stem-cell colony-stimulating factor), the platelet-specific integrin $\alpha IIb\beta$, multidrug resistance genes, the gp91 or gp 47 genes that are defective in patients with chronic granulomatous disease (CGD), antiviral genes rendering cells resistant to infections with pathogens such as human immunodeficiency virus, genes coding for blood coagulation factors VIII or IX which are mutated in hemophiliacs, ligands involved in T cell-mediated immune responses such as T cell antigen receptors, B cell antigen receptors (immunoglobulins) as well as combination of T and B cell antigen receptors alone or in combination with single chain antibodies such as ScFv, tumor necrosis factor (TNF), IL-2, IL-12, gamma interferon, CTLA4, B7 and the like, genes expressed in tumor cells such as Melana, MAGE genes (such as MAGE-1, MAGE-3), P198, P1A, gp100 etc.

A principal application of the present transgenes will be to deliver desired transgenes to hematopoietic cells for a number of possible reasons. This might include, but of course not be limited to, the treatment of myelosupression and neutropenias which may be caused as a result of chemotherapy or immunosupressive therapy or infections such as AIDS, genetic disorders, cancers and the like.

Exemplary genetic disorders of hematopoietic cells that are contemplated include sickle cell anemia, thalassemias, hemaglobinopathies, Glanzmann thrombasthenia, lysosomal storage disorders (such as Fabry disease, Gaucher disease, Niemann-Pick disease, and Wiskott-Aldrich syndrome), severe combined immunodeficiency syndromes (SCID), as well as diseases resulting from the lack of systemic production of a secreted protein, for example, coagulation factor VIII and/or IX. In such cases, one would desire to introduce transgenes such as globin genes, hematopoietic growth factors, which include erythropoietin (EPO), the interleukins (especially Interleukin-1, Interleukin-2, Interleukin-3, Interleukin-6, Interleukin-12, etc.) and the colony-stimulating factors (such as granulocyte colony-stimulating factor, granulocyte/macrophage colony-stimulating factor, or stem-cell colony-stimulating factor), the platelet-specific integrin $\alpha IIb\beta$, multidrug resistance genes, the gp91 or gp 47 genes which are defective in patients with chronic granulomatous disease (CGD), antiviral genes rendering cells resistant to infections with pathogens such as human immunodeficiency virus, genes coding for blood coagulation factors VIII or IX which are mutated in hemophiliacs, ligands involved in T cell-mediated immune responses such as T cell antigen receptors, B cell antigen receptors (immunoglobulins), a combination of both T and B cell antigen receptors alone and/or in combination with single chain antibodies (ScFv), IL2, IL12, TNF, gamma interferon, CTLA4, B7 and the like, genes expressed in tumor cells such as Melana, MAGE genes (such as MAGE-1, MAGE-3), P198, P1A, gp100 etc.

Exemplary cancers are those of hematopoietic origin, for example, arising from myeloid, lymphoid or erythroid lineages, or precursor cells thereof. Exemplary myeloid disorders include, but are not limited to, acute promyeloid leukemia (APML), acute myelogenous leukemia (AML) and chronic myelogenous leukemia (CML). Lymphoid malignancies which may be treated utilizing the lentivectors of the present invention include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas contemplated as candidates for treatment utilizing the lentiviral vectors of the present invention include, but are not limited to non-Hodgkin lymphoma and variants thereof, peripheral T-cell lymphomas, adult T-cell leukemia/lymphoma (ATL), cutaneous T-cell lymphoma (CTCL), large granular lymphocytic leukemia (LGF) and Hodgkin's disease.

In other embodiments, the present invention is directed to host cells that have been transduced with one of the foregoing lentivectors. It is believed that the lentivectors of the present invention can be employed to transduce most any cell. Exemplary cells include but are not limited to a CD4$^+$ T cell, a peripheral blood lymphocyte cell, a peripheral blood mononuclear cell, a hematopoietic stem cell, a fetal cord blood cell, a fibroblast cell, a brain cell, a lung cell, a liver cell, a muscle cell, a pancreatic cell, an endothelial cell, a cardiac cell, a skin cell, a bone marrow stromal cell, and an eye cells, a pancreatic ductal cell, a neural precursor, a mesodermal stem cell and the like. The cells transduced may further be primate, murine, porcine, or human in origin, or come from another animal species.

For the production of virus particles, one may employ any cell that is compatible with the expression of lentiviral Gag and Pol genes, or any cell that can be engineered to support such expression. For example, producer cells such as 293T cells and HT1080 cells may be used.

Of course, as noted above, the lentivectors of the invention will be particularly useful in the transduction of human hematopoietic progenitor cell or a hematopoietic stem cell, obtained either from the bone marrow, the peripheral blood or the umbilical cord blood, as well as in the transduction of a CD4$^+$ T cell, a peripheral blood B or T lymphocyte cell, a peripheral blood mononuclear cell, a dendritic cell, and a monocytic cell. Particularly preferred targets are CD34$^+$ cells.

In still other embodiments, the present invention is directed to a method for transducing a human hematopoietic stem cell comprising contacting a population of human cells that include hematopoietic stem cells with one of the foregoing lentivectors under conditions to effect the transduction of a human hematopoietic progenitor cell in said population by the vector. The stem cells may be transduced in vivo or in vitro, depending on the ultimate application. Even in the context of human gene therapy, such as gene therapy of human stem cells, one may transduce the stem cell in vivo or, alternatively, transduce in vitro followed by infusion of the transduced stem cell into a human subject. In one aspect of this embodiment, the human stem cell can be removed from a human, e.g., a human patient, using methods well known to those of skill in the art and transduced as noted above. The transduced stem cells are then reintroduced into the same or a different human.

Where a human subject is treated directly by introduction of the vector into the subject, the treatment is typically carried out by intravenous administration of the vector. When cells, for instance CD34$^+$ cells, dendritic cells, peripheral blood cells or tumor cells are transduced ex vivo, the vector particles are incubated with the cells using a dose generally in the order of between 1 to 50 multiplicities of infection (MOI) which also corresponds to $1\times10^5$ to $50\times10^5$ transducing units of the viral vector per $10^5$ cells. This of course includes amount of vector corresponding to 1, 2, 3, 4, 5, 6, 7, 8, 9, 10, 15, 20, 25, 30, 35, 40, 45, and 50 MOI. Typically, the amount of vector may be expressed in terms of HeLa transducing units (TU). Other routes for vector administration include intrarterially, endoscopically, intralesionally, percutaneously, subcutaneously, intramuscular, intrathecally, intraorbitally, intradermally, intraperitoneally, transtracheally, subcuticularly, by intrasternal injection, by inhalation or intranasal spraying, by endotracheal route and the like. In embodiments concerning tumor/cancer therapies with the vectors of the invention the expression vector can be delivered by direct injection into the tumor or into the tumor vasculature.

A typical example of ex vivo gene therapy is a patient suffering from chronic granulatous disease (CGD), whose CD34$^+$ cells can be isolated from the bone marrow or the peripheral blood and transduced ex vivo with a lentivector expressing the gp91hox gene before reimplantation. In the case of patients suffering from severe combined immunodeficiency (SCID), the inventors contemplate a similar approach, using lentivectors of the invention expressing the gene defective in the patient, for example, the gene encoding the common gamma chain of the Interleukin receptor. For the genetic treatment of HIV infection, the present inventors contemplate intracellular immunization, wherein cells are rendered resistant to the HIV virus through the introduction of antiviral genes. In embodiments of the intracellular immunization for HIV, targets of the lentivectors of the invention include hematopoietic progenitors, peripheral blood CD4$^+$ T cells, and monocytes. As will be recognized by the skilled artisan, similar intracellular immunization methods can be used for other viral infections as well. For the immunotherapy of cancers, tumor cells or antigen presenting cells such as dendritic cells will be genetically engineered with the lentivectors of the invention. For cancer therapies some transgenes that may be used in the lentivector constructs of the invention are those that can inhibit, and/or kill, and/or prevent the proliferation, and/or mediate the apoptosis of, the cancer/tumor cell and/or genes such as TNF.

The lentivectors described herein may also be used in vivo, by direct injection into the blood or into a specific organ. For example, in one embodiment intracerebral injection of lentivectors expressing the Glial Cell Derived Nerve Growth Factor (GDNF), can be used for the treatment of Parkinson's disease. In another example, intraportal injection of a lentivector expressing coagulation factor VIII for the correction of hemophilia A is envisioned. In yet another example, intravenous or intramuscular injection of a lentivector of the present invention expressing the dystrophin gene for the treatment of Duchenne Muscular Dystrophy is envisioned. Thus, one of ordinary skill in the art will appreciate the extensive use of the lentivector constructs of the present invention in terms of gene therapies.

As used herein the specification or claim(s) when used in conjunction with the word "comprising", the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

These data are from 3 independent experiments for the 0-10 MOI range and from 2 for 10-50 MOI range. Error bars represent SD.

Figure 3:
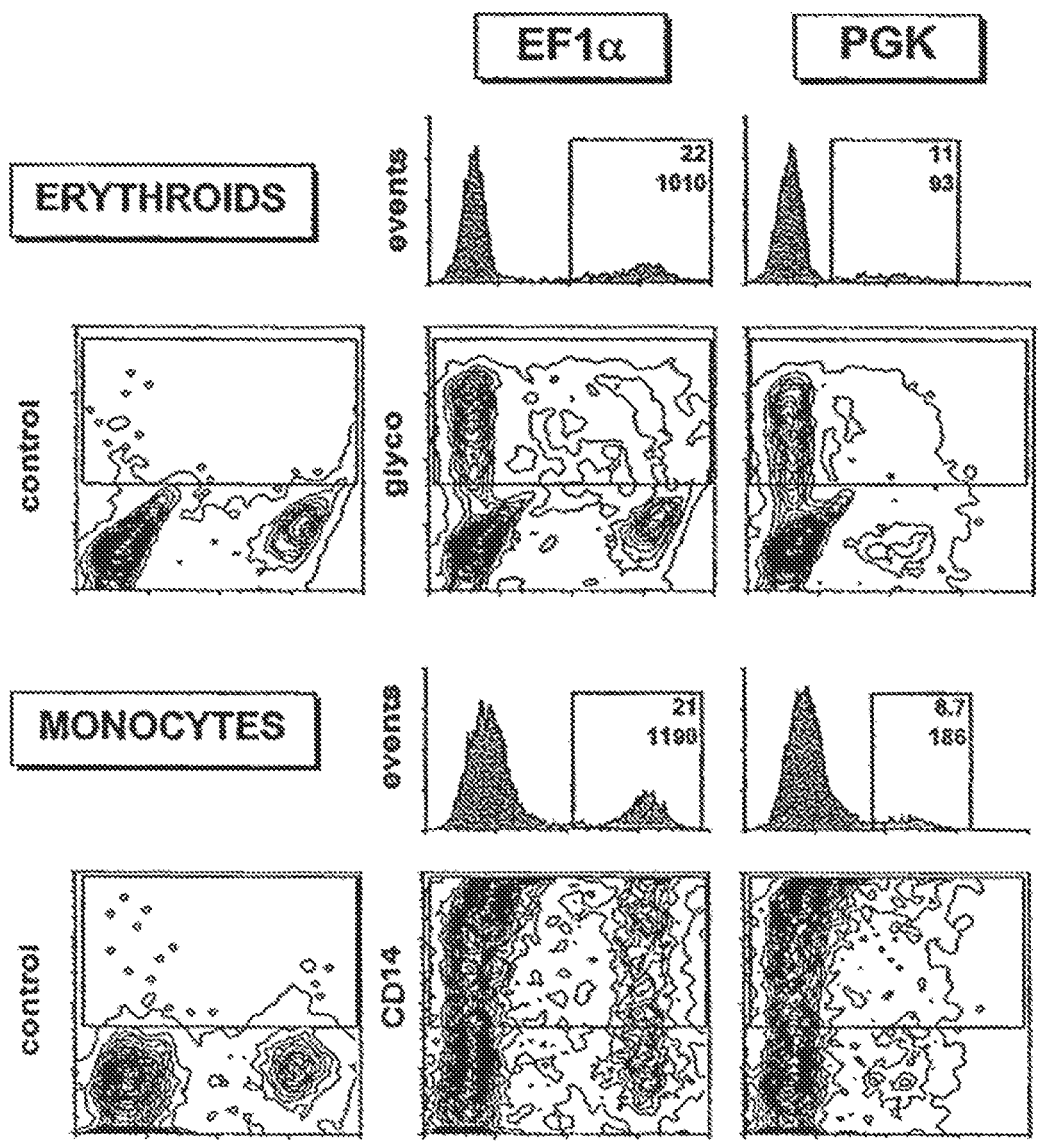

FIG. 3. Transgene expression in differentiated hematopoietic lineages after transduction of human CD34+ cells with HIV-derived vectors. Human CD34+ cells from umbilical cord blood ($10^5$ cells) were transduced with $10^6$ TU of HIV vectors (corresponding to a MOI of 10) containing either the EF1α or the PGK promoters and differentiated into various hematopoietic lineages as described in the section entitled Examples. After differentiation, HIV-EF1α- (first and second column) or HIV-PGK-transduced cells (third column) were analyzed by flow cytometry for both GFP (x axis) and lineage-specific markers expression (glycophorin, CD14, CD42b, CD15 and CD1a for respectively erythroids, monocytes, megakaryocytes, granulocytes, and dendritic cells). Isotype control antibodies were used in the first column. For each promoter, cell populations expressing high levels of lineage-specific marker were gated (upper rectangle in 2D plots), and monoparametric frequency histograms of GFP expression for these cells were generated (located above the 2D plots). The percentage of GFP+ cells (upper number), and median of fluorescence intensity of GFP (lower number) was determined. For the experiment generating erythroids, monocytes, megakaryocytes and granulocytes, the fraction of GFP+ CD34+ cells before differentiation was 22% for EF1α and 16% for PGK. For the experiment generating DCs, the fraction of GFP+ precursors before differentiation was 32% for EF1α and 29% for PGK. These data are representative of 4 independent experiments.

Figure 4:
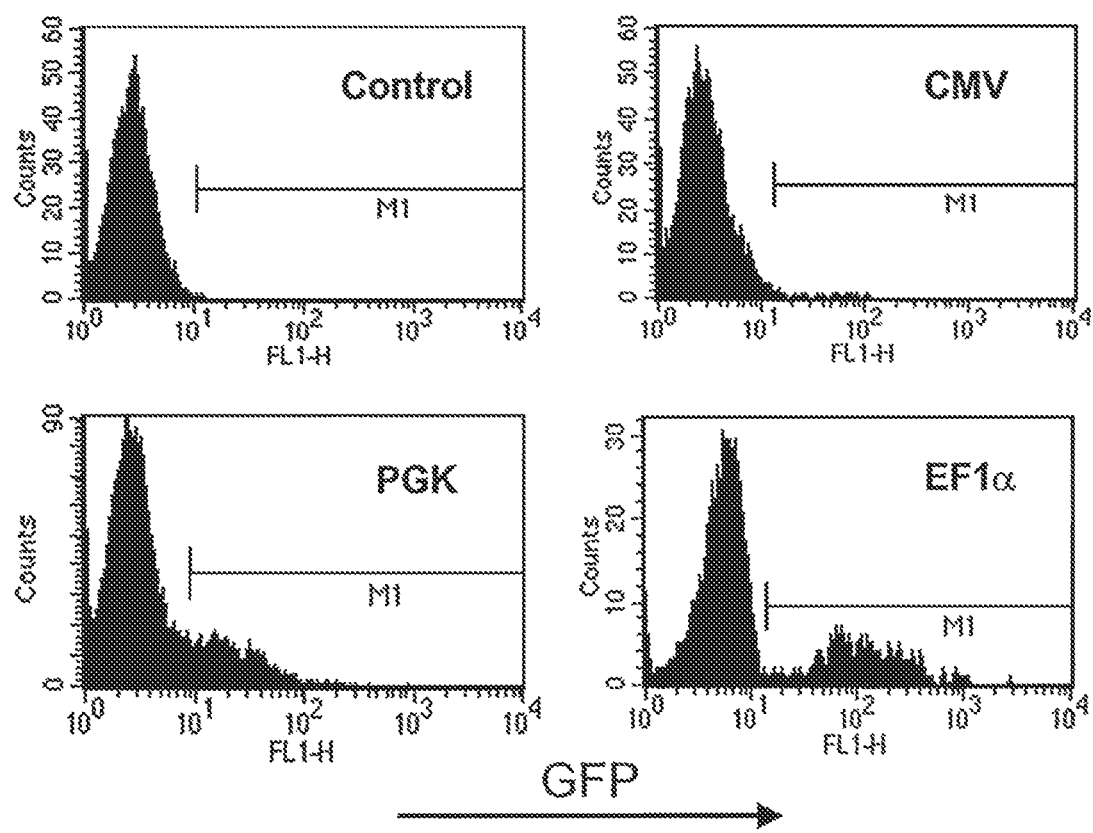

FIG. 4. GFP expression in lentivector-transduced primary human T lymphocytes. CMV-, PGK- or EF1α-containing HIV-derived vectors were used to infect PHA-activated primary T lymphocytes. Cells were maintained for 5 days in culture medium supplemented with IL-2 before analyzing GFP expression by flow cytometry. Two-dimensional plot represents cell number as a function of GFP levels. Results are representative of at least five independent experiments.

FIG. 5A. and FIG. 5B. Effect of SIN design and WPRE addition on transgene expression in human CD34+ cells. $10^5$ CD34+ cells were transduced with $10^6$ HeLa-TU of the indicated GFP-expressing HIV-derived vectors and analyzed by flow cytometry four days later. Vectors were as follows: (FIG. 5A) PGK (2 intact LTRs); PGK-SIN (3'SIN LTR deletion, see materials and methods); PGK-SIN-W (addition of WPRE upstream of the 3'SIN-LTR). (FIG. 5B) Same analysis as in FIG. 5A, but with EF1α promoter instead of PGK promoter. Results are represented as contour graphs of CD34 expression versus GFP expression (four-log scale). For each condition, GFP expression is also displayed as histograms of GFP fluorescence intensity α-axis, four-log scale) versus number of cells (y-axis, linear). Number in square represents median of fluorescence intensity of GFP+ cells.

Figure 6:
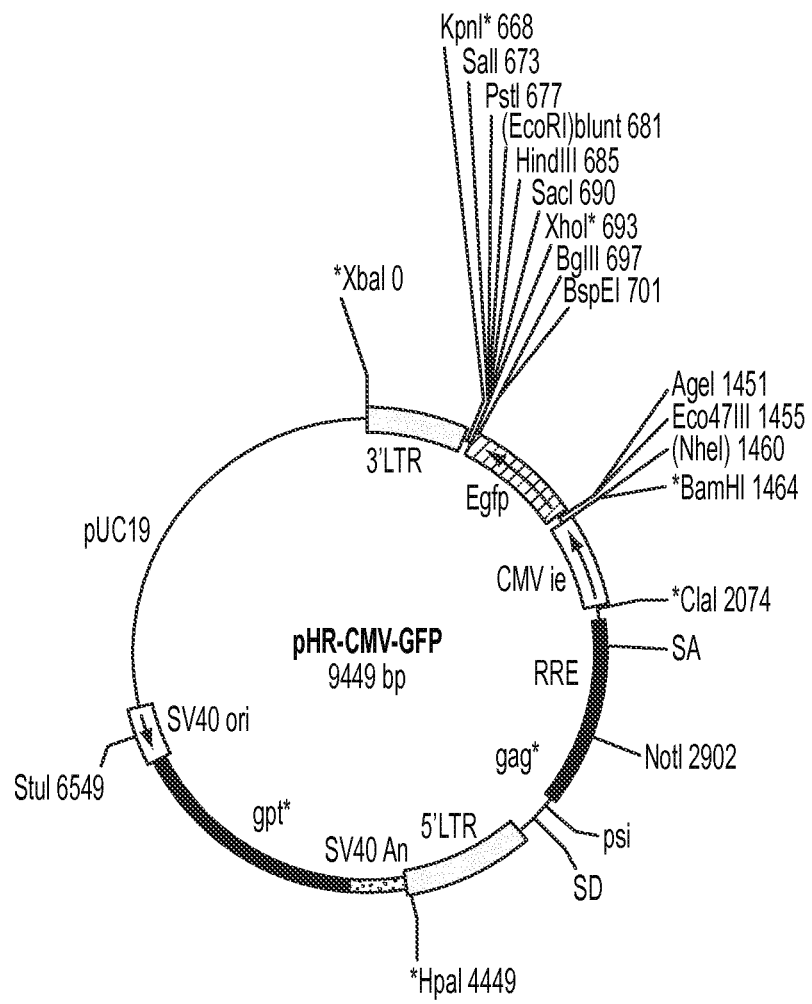

FIG. 6. Map depicting the construct pHR-CMV-GFP. Same as pHR-CMV-LACz (Genbank AF 105229) but with EGFP instead of LacZ.

Figure 7:
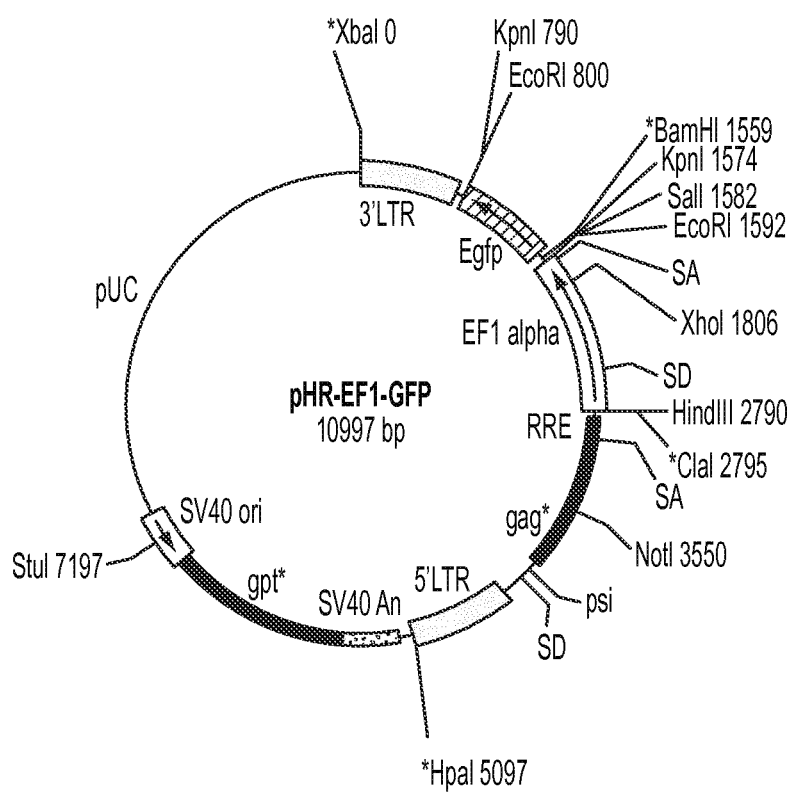

FIG. 7. Map depicting the construct pHR-EF1-GFP. Also referred to as pHR'-EF1alpha-EGFP. ClaI, HindIII and EcoRI cut outside of EF1alpha promoter (Nagata, G181962).

Figure 8:
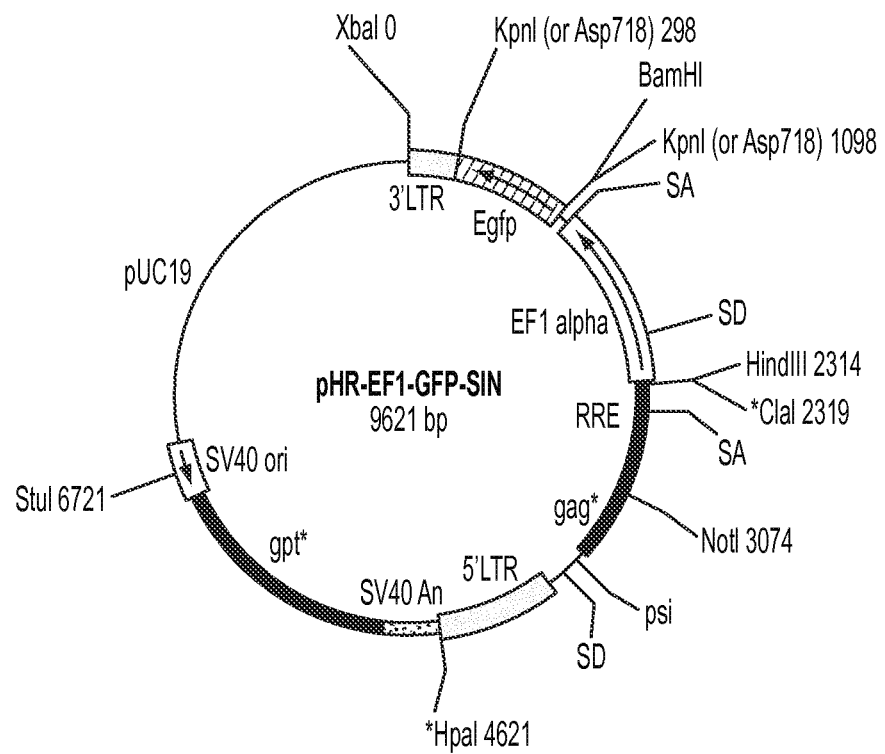

FIG. 8. Map depicting the construct pHR-EF1-GFP-SIN. Deletion of WPRE by insertion of Asp718/Asp718 fragment (~0.8 kb) from pHR'-EF1alpha-EGFP (Uni-Lund Lab, Sweden) into Asp718/Asp718 sites of pHR-E-GFP-W.

Figure 9:
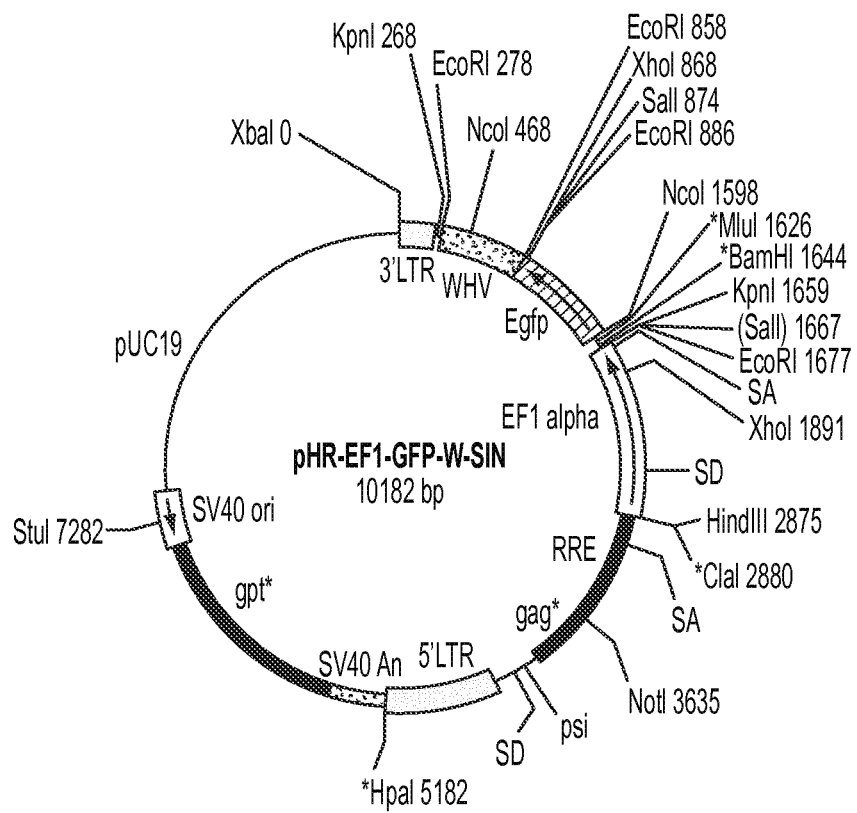

FIG. 9. Map depicting the construct pHR-EF1-GFP-W-SIN. Insertion of ClaI/BamHI fragment from pHR'-EF1-GFP (Uni-Lund, Sweden) containing the promoter of the human EF1alpha gene (Nagata, G181962) into ClaI/BamHI sites of pHRGFP/delta ClaI. SalI site at 1757 destroyed for subsequent clonings.

DESCRIPTION OF ILLUSTRATIVE EMBODIMENTS

While lentiviral vectors offer a great potential for gene-therapy and especially the transduction of human hematopoietic stem cells (hHSC), vectors developed so far have failed to meet biosaftey standards and are still inefficient in expression of transgenes. For example, while CMV promoter-containing HIV-derived vectors can induce high levels of transgene expression in the central nervous system (Naldini et al., 1996a; Naldini et al., 1996b; Blomer et al., 1997), and allowed the initial demonstration that pluripotent hematopoietic precursors can be efficiently transduced by this gene delivery tool, they are largely useless for transferring therapeutic genes into most lympho-hematopoietic cells, because in these targets their transcriptional activity is prohibitively low (Miyoshi et al., 1999; Case et al., 1999; An et al., 2000). Current lentiviral vectors have multiply attenuated HIV virulence genes which removes the potential for reconstitution of wild-type virus by recombination (Zufferey et al., 1997; Dull et al., 1998). A self-inactivating design rendered the vectors further biologically safe by eliminating the transcriptional elements of HIV (Zufferey et al., 1998). However, this can negatively affect transgene expression, apparently by decreasing the efficiency of polyadenylation (DeZazzo et al., 1991; Valsamakis et al., 1991; Brown et al., 1991; Chemington and Ganem, 1992; Valsamakis et al., 1992; Gilmartin et al., 1992).

The present invention overcomes such and other deficiencies in the art and describes the development of improved HIV-derived vectors that are optimized in terms of both biosaftey and increased gene expression. Thus, the transduction of human cells with HIV-derived lentivectors which comprise elements that prevent the formation of replication competent recombinants (RCR) and further comprise an internal promoter element which induces high levels of transgene expression in both hematopoietic precursors and in vitro differentiated blood lineages, as well as in primary T cells demonstrated herein that. For example, human CD34+ cells as well as other human hematopoietic lineages can be transduced using the vectors of this invention.

The promoter elements of the vectors described include the EF1α promoter or the PGK promoter, although, as will be recognized by one of skill in the art, almost any promoter element may be used. However, CMV promoters are not preferred. For example, the inventors demonstrate using the green fluorescent protein (GFP) expression that while the EF1α promoter element or the PGK promoter were highly active in CD34+ cells as well as several other differentiated hematopoietic derivatives, the CMV promoter driven GFP production was insufficient to determine either the percentage of transduced cells or the level of transgene expression in those cells. Also contemplated are engraftment and repopulation assays in NOD/SCID mice with both HIV-PGK and HIV-EF1α vectors, to confirm the stability of expression from these promoters in vivo.

The element that prevents RCR in the lentivectors of the present invention is the self inactivating (SIN) design. This is achieved by the deletion of a major part of U3 in the 3'LTR of the vector plasmid, leading to a self-inactivating (SIN) configuration (Zufferey et al., 1998). This deletion also prevents potential interference between LTR and the internal promoter elements. However, the SIN can induce decreases in transgene expression, especially in promoters that are not very strong such as the PGK promoter. The invention further describes methods that rescue transgene levels in lentivector constructs that do not have strong promoters by inserting other regulatory elements such as the woodchuck hepatitis virus post-transcriptional regulatory element (WPRE) or the hepatitis virus B regulatory element (HPRE) in the vector, immediately upstream of the deleted 3' LTR.

The lentivectors of this invention can efficiently transduce several human blood lineage cells including CD34+ cells using conditions under which MLV-based vectors are inefficient. Furthermore, it is also demonstrated that human CD34+ cells can be efficiently transduced at a relatively low MOI, although the efficacy of gene transfer saturates at about 20 to 30% of transduced cells. For example, an MOI of 10 was used to achieve optimal transduction which is significantly lower than that described in previous studies, where it ranged between 60-300 and 1000-3000 (Miyoshi et al., 1999; Case et al., 1999). This may in part be due to enhanced vector-target meeting probability as the methods of the present invention involve exposure of CD34+ cells to the vector particles in a small volume ($10^5$ cells in 200 µl) and for a duration of 24 hrs.

Thus, the present invention provides HIV-derived vectors which are safe, highly efficient, and very potent for expressing transgenes in human hematopoietic progenitor cells as well as in all other blood cell derivatives, even in a self-inactivating configuration. These vectors therefore provide useful tools for genetic treatments such as inherited and acquired lympho-hematological disorders, gene-therapies for cancers especially the hematological cancers, as well as for the study of hematopoiesis via lentivector-mediated modification of human HSCs.

A. Lentiviral Vectors and Gene Therapy

Lentiviruses are complex retroviruses, which, in addition to the common retroviral genes gag, pol, and env, contain other genes with regulatory or structural function. The higher complexity enables the virus to modulate its life cycle, as in the course of latent infection. Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Lentiviral vectors offer great advantages for gene therapy. They integrate stably into chromosomes of target cells which is required for long-term expression. Further, they do not transfer viral genes therefore avoiding the problem of generating transduced cells that can be destroyed by cytotoxic T-cells. Furthermore, they have a relatively large cloning capacity, sufficient for most envisioned clinical applications. In addition, lentiviruses, in contrast to other retroviruses, are capable of transducing non-dividing cells. This is very important in the context of gene-therapy for tissues such as the hematopoietic system, the brain, liver, lungs and muscle. For example, vectors derived from HIV-1 allow efficient in vivo and ex vivo delivery, integration and stable expression of transgenes into cells such a neurons, hepatocytes, and myocytes (Blomer et al., 1997; Kafri et al., 1997; Naldini et al., 1996; Naldini et al., 1998).

The lentiviral genome and the proviral DNA have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNA's. The LTR contains all other cis-acting sequences necessary for viral replication. Lentiviruses have additional genes including vif, vpr, tat, rev, vpu, nef and vpx.

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA. However, the resulting mutant remains capable of directing the synthesis of all virion proteins.

Lentiviral vectors are known in the art, see Naldini et al., (1996 and 1998); Zufferey et al., (1997); Dull et al., 1998, U.S. Pat. Nos. 6,013,516; and 5,994,136 all incorporated herein by reference. In general, these vectors are plasmid-based or virus-based, and are configured to carry the essential sequences for incorporating foreign nucleic acid, for selection and for transfer of the nucleic acid into a host cell.

Two components are involved in making a virus-based gene delivery system: first, the packaging elements, encompassing the structural proteins as well as the enzymes necessary to generate an infectious particle, and second, the vector itself, i.e., the genetic material to be transferred. Biosaftey safeguards can be introduced in the design of both of these components. Thus, the packaging unit of the first generation HIV-based vectors comprised all HIV-1 proteins except the envelope proteins (Naldini et al., 1998). Subsequently it was shown that the deletion of four additional viral genes that are responsible for virulence including, vpr, vif, vpu and nef did not alter the utility of the vector system (Zufferey et al., 1997). It was also shown that Tat, the main transactivator of HIV is also dispensable for the generation of a fully efficient vector (Dull et al., 1998). Thus, the third-generation packaging unit of the HIV-based lentiviral vectors comprise only three genes of the parental virus: gag, pol and rev, which eliminates the possibility of reconstitution of a wild-type virus through recombination.

This system was further improved by removing HIV transcriptional units from the vector (Zufferey et al., 1998). It was demonstrated therein that introducing a deletion in the U3 region of the 3' LTR of the DNA used to produce the vector RNA generated self-inactivating (SIN) vectors. During reverse transcription this deletion is transferred to the 5' LTR of the proviral DNA. Enough sequence was eliminated, including the removal of a TATA box, which abolished the transcriptional activity of the LTR, which prevents production of full-length vector RNA in transduced cells. This however did not affect vector titers or the in vitro or in vivo properties of the vector.

The present invention provides several improvements to the existing lentivectors as described above and in other parts of this specification. Introducing a lentivector providing a heterologous gene, such as genes to treat hematopoietic and lympho-hematopoietic disorders in this invention, into a packaging cell yields a producer cell which releases infectious viral particles carrying the foreign gene of interest.

The env gene can be derived from any virus, including retroviruses. The env preferably is an amphotropic envelope protein which allows transduction of cells of human and other species. Examples of retroviral-derived env genes include, but are not limited to: Moloney murine leukemia virus (Mo-MuLV or MMLV), Harvey murine sarcoma virus (HaMuSV or HSV), murine mammary tumor virus (MuMTV or MMTV), gibbon ape leukemia virus (GaLV or GALV), human immunodeficiency virus (HIV) and Rous sarcoma virus (RSV). Other env genes such as Vesicular stomatitis virus (VSV) protein G (VSV G), that of hepatitis viruses and of influenza also can be used.

While VSV G protein is a desirable env gene because VSV G confers broad host range on the recombinant virus, VSV G can be deleterious to the host cell. Thus, when a gene such as that for VSV G is used, it is preferred to employ an inducible promoter system so that VSV G expression can be regulated to minimize host toxicity when VSV G is expression is not required. For example, the tetracycline-regulatable gene expression system of Gossen & Bujard, (1992) can be employed to provide for inducible expression of VSV G when tetracycline is withdrawn from the transferred cell. Thus, the tet/VP16 transactivator is present on a first vector and the VSV G coding sequence is cloned downstream from a promoter controlled by tet operator sequences on another vector.

The vector providing the viral env nucleic acid sequence is associated operably with regulatory sequences, e.g., a promoter or enhancer. The regulatory sequence can be any eukaryotic promoter or enhancer, including for example, EF1α, PGK, the Moloney murine leukemia virus promoter-enhancer element, the human cytomegalovirus enhancer, the vaccinia P7.5 promoter or the like (also see examples listed in Tables 1 and 2 below). In some cases, such as the Moloney murine leukemia virus promoter-enhancer element, the promoter-enhancer elements are located within or adjacent to the LTR sequences. Preferably, the regulatory sequence is one which is not endogenous to the lentivirus from which the vector is being constructed. Thus, if the vector is being made from SIV, the SIV regulatory sequence found in the SIV LTR would be replaced by a regulatory element which does not originate from SIV.

One may further target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific. Retroviral vectors can be made target-specific by inserting, for example, a glycolipid or a protein. Targeting often is accomplished by using an antigen-binding portion of an antibody or a recombinant antibody-type molecule, such as a single chain antibody, to target the retroviral vector. Those of skill in the art will know of, or can readily ascertain without undue experimentation, specific methods to achieve delivery of a retroviral vector to a specific target.

The heterologous or foreign nucleic acid sequence, such as a polynucleotide sequence encoding a gene such as a therapeutic gene for inherited or acquired hematopoietic disorders herein, is linked operably to a regulatory nucleic acid sequence. Preferably, the heterologous sequence is linked to a promoter, resulting in a chimeric gene.

Marker genes may be utilized to assay for the presence of the vector, and thus, to confirm infection and integration. The presence of a marker gene ensures the selection and growth of only those host cells which express the inserts. Typical selection genes encode proteins that confer resistance to antibiotics and other toxic substances, e.g., histidinol, puromycin, hygromycin, neomycin, methotrexate, and cell surface markers.

The recombinant virus of the invention is capable of transferring a nucleic acid sequence into a mammalian cell. The term, "nucleic acid sequence", refers to any nucleic acid molecule, preferably DNA, as discussed in detail herein. The nucleic acid molecule may be derived from a variety of sources, including DNA, cDNA, synthetic DNA, RNA or combinations thereof. Such nucleic acid sequences may comprise genomic DNA which may or may not include naturally occurring introns. Moreover, such genomic DNA may be obtained in association with promoter regions, poly A sequences or other associated sequences. Genomic DNA may be extracted and purified from suitable cells by means well known in the art. Alternatively, messenger RNA (mRNA) can be isolated from cells and used to produce cDNA by reverse transcription or other means.

The vectors are introduced via transfection or infection into the packaging cell line. The packaging cell line produces viral particles that contain the vector genome. Methods for transfection or infection are well known by those of skill in the art. After cotransfection of the packaging vectors and the transfer vector to the packaging cell line, the recombinant virus is recovered from the culture media and tittered by standard methods used by those of skill in the art. Thus, the packaging constructs can be introduced into human cell lines by calcium phosphate transfection, lipofection or electroporation, generally together with a dominant selectable marker, such as neomycin, DHFR, Glutamine synthetase or ADA, followed by selection in the presence of the appropriate drug and isolation of clones. The selectable marker gene can be linked physically to the packaging genes in the construct.

Stable cell lines wherein the packaging functions are configured to be expressed by a suitable packaging cell are known. For example, see U.S. Pat. No. 5,686,279; and Ory et al., (1996), which describe packaging cells. The packaging cells with a lentiviral vector incorporated in them form producer cells. Producer cells are thus cells or cell-lines that can produce or release packaged infectious viral particles carrying the therapeutic gene of interest. These cells can further be anchorage dependent which means that these cells will grow, survive, or maintain function optimally when attached to a surface such as glass or plastic. The producer cells may also be neoplastically transformed cells. Some examples of anchorage dependent cell lines used as lentiviral vector packaging cell lines when the vector is replication competent are HeLa or 293 cells and PERC.6 cells.

In some applications, particularly when the virus is to be used for gene therapy applications, it is preferable that the vector be replication deficient (or replication defective) to avoid uncontrolled proliferation of the virus in the individual to be treated. In such instances mammalian cell lines are selected which have been engineered, either by modification of the producer cell's genome to encode essential viral functions or by the co-infection of the producer cell with a helper virus, to express proteins complementing the effect of the sequences deleted from the viral genome. For example, for HIV-1 derived vectors, the HIV-1 packaging cell line, PSI422, may be used as described in Corbeau, et al. (1996). Similarly, where the viral vector to be produced is a retrovirus, the human 293-derived retroviral packaging cell line (293GPG) capable of producing high titers of retroviral particles may be employed as described in Ory, et al. (1996). In the production of minimal vector systems, the producer cell is engineered (either by modification of the viral genome or by the use of helper virus or cosmid) to complement the functions of the parent virus enabling replication and packaging into virions in the producer cell line.

Lentiviral transfer vectors Naldini et al., (1996), have been used to infect human cells growth-arrested in vitro and to transduce neurons after direct injection into the brain of adult rats. The vector was efficient at transferring marker genes in vivo into the neurons and long term expression in the absence of detectable pathology was achieved. Animals analyzed ten months after a single injection of the vector showed no decrease in the average level of transgene expression and no sign of tissue pathology or immune reaction (Blomer et al., (1997).

B. The Sin Design

The SIN design increases the biosaftey of the lentiviral vectors. The majority of the HIV LTR is comprised of the U3 sequences. The U3 region contains the enhancer and promoter elements that modulate basal and induced expression of the HIV genome in infected cells and in response to cell activation. Several of these promoter elements are essential for viral replication. Some of the enhancer elements are highly conserved among viral isolates and have been implicated as critical virulence factors in viral pathogenesis. The enhancer elements may act to influence replication rates in the different cellular target of the virus (Marthas et al., 1993).

As viral transcription starts at the 3' end of the U3 region of the 5' LTR, those sequences are not part of the viral mRNA and a copy thereof from the 3' LTR acts as template for the generation of both LTR's in the integrated provirus. If the 3' copy of the U3 region is altered in a retroviral vector construct, the vector RNA is still produced from the intact 5' LTR in producer cells, but cannot be regenerated in target cells. Transduction of such a vector results in the inactivation of both LTR's in the progeny virus. Thus, the retrovirus is self-inactivating (SIN) and those vectors are known as SIN transfer vectors.

The SIN design is described in further detail in Zufferey et al., 1998 and U.S. Pat. No. 5,994,136 both incorporated herein by reference. As described therein, there are, however, limits to the extent of the deletion at the 3' LTR. First, the 5' end of the U3 region serves another essential function in vector transfer, being required for integration (terminal dinucleotide+att sequence). Thus, the terminal dinucleotide and the att sequence may represent the 5' boundary of the U3 sequences which can be deleted. In addition, some loosely defined regions may influence the activity of the downstream polyadenylation site in the R region. Excessive deletion of U3 sequence from the 3' LTR may decrease polyadenylation of vector transcripts with adverse consequences both on the titer of the vector in producer cells and the transgene expression in target cells. On the other hand, limited deletions may not abrogate the transcriptional activity of the LTR in transduced cells.

The lentiviral vectors described herein carry deletions of the U3 region of the 3' LTR spanning from nucleotide −418 to −18. This is the most extensive deletion and extends as far as to the TATA box, therefore abrogating any transcriptional activity of the LTR in transduced cells. The titer of vector in producer cells as well as transgene expression in target cells was unaffected in these vectors. This design therefore provides an enormous increase in vector safety.

SIN-type vectors with such extensive deletions of the U3 region cannot be generated for murine leukemia virus (MLV) or spleen necrosis virus (SNV) based retroviral vectors without compromising efficiency of transduction.

Elimination of the −418 to −18 nucleotide sequence abolishes transcriptional activity of the LTR, thereby abolishing the production of full length vector RNA in transduced cells. In the HIV-derived lentivectors none of the in vitro or in vivo properties were compromised by the SIN design.

C. Posttranscriptionally Regulating Elements (Pre)

Enhancing transgene expression may be required in certain embodiments, especially those that involve lentiviral constructs of the present invention with modest promoters.

One type of PRE is an intron positioned within the expression cassette, which can stimulate gene expression. However, introns can be spliced out during the life cycle events of a lentivirus. Hence, if introns are used as PRE's they have to be placed in an opposite orientation to the vector genomic transcript.

Posttranscriptional regulatory elements that do not rely on splicing events offer the advantage of not being removed during the viral life cycle. Some examples are the posttranscriptional processing element of herpes simplex virus, the posttranscriptional regulatory element of the hepatitis B virus (HPRE) and the woodchuck hepatitis virus (WPRE). Of these the WPRE is most preferred as it contains an additional cis-acting element not found in the HPRE (Donello et al., 1998). This regulatory element is positioned within the vector so as to be included in the RNA transcript of the transgene, but outside of stop codon of the transgene translational unit. As demonstrated in the present invention and in Zufferey et al., 1999, the WPRE element is a useful tool for stimulating and enhancing gene expression of desired transgenes in the context of the lentiviral vectors.

The WPRE is characterized and described in U.S. Pat. No. 6,136,597, incorporated herein by reference. As described therein, the WPRE is an RNA export element that mediates efficient transport of RNA from the nucleus to the cytoplasm. It enhances the expression of transgenes by insertion of a cis-acting nucleic acid sequence, such that the element and the transgene are contained within a single transcript. Presence of the WPRE in the sense orientation was shown to increase transgene expression by up to 7 to 10 fold. Retroviral vectors transfer sequences in the form of cDNAs instead of complete intron-containing genes as introns are generally spliced out during the sequence of events leading to the formation of the retroviral particle. Introns mediate the interaction of primary transcripts with the splicing machinery. Because the processing of RNAs by the splicing machinery facilitates their cytoplasmic export, due to a coupling between the splicing and transport machineries, cDNAs are often inefficiently expressed. Thus, the inclusion of the WPRE in a vector results in enhanced expression of transgenes.

D. Nucleic Acids

One embodiment of the present invention is to transfer nucleic acids encoding a therapeutic gene, especially a gene that provides therapy for hematopoietic and lympho-hematopoietic disorders, such as the inherited or acquired disorders described above. In one embodiment the nucleic acids encode a full-length, substantially full-length, or functional equivalent form of such a gene.

Thus, in some embodiments of the present invention, the treatment of a hematopoietic and lympho-hematopoietic disorder involves the administration of a lentiviral vector of the invention comprising a therapeutic nucleic acid expression construct to a cell of hematopoietic origin. It is contemplated that the hematopoietic cells take up the construct and express the therapeutic polypeptide encoded by nucleic acid, thereby restoring the cells normal phenotype.

A nucleic acid may be made by any technique known to one of ordinary skill in the art. Non-limiting examples of synthetic nucleic acid, particularly a synthetic oligonucleotide, include a nucleic acid made by in vitro chemical synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986, and U.S. patent Ser. No. 5,705,629, each incorporated herein by reference. A non-limiting example of enzymatically produced nucleic acid include one produced by enzymes in amplification reactions such as PCR™ (see for example, U.S. Pat. Nos. 4,683,202 and 4,682,195, each incorporated herein by reference), or the synthesis of oligonucleotides described in U.S. Pat. No. 5,645,897, incorporated herein by reference. A non-limiting example of a biologically produced nucleic acid includes recombinant nucleic acid production in living cells (see for example, Sambrook et al. 1989, incorporated herein by reference).

A nucleic acid may be purified on polyacrylamide gels, cesium chloride centrifugation gradients, or by any other means known to one of ordinary skill in the art (see for example, Sambrook et al. 1989, incorporated herein by reference).

The term "nucleic acid" will generally refer to at least one molecule or strand of DNA, RNA or a derivative or mimic thereof, comprising at least one nucleobase, such as, for example, a naturally occurring purine or pyrimidine base found in DNA (e.g., adenine "A," guanine "G," thymine "T," and cytosine "C") or RNA (e.g. A, G, uracil "U," and C). The term "nucleic acid" encompasses the terms "oligonucleotide" and "polynucleotide." The term "oligonucleotide" refers to at least one molecule of between about 3 and about 100 nucleobases in length. The term "polynucleotide" refers to at least one molecule of greater than about 100 nucleobases in length. These definitions generally refer to at least one single-stranded molecule, but in specific embodiments will also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule.

In certain embodiments, a "gene" refers to a nucleic acid that is transcribed. As used herein, a "gene segment" is a nucleic acid segment of a gene. In certain aspects, the gene includes regulatory sequences involved in transcription, or message production or composition. In particular embodiments, the gene comprises transcribed sequences that encode for a protein, polypeptide or peptide. In other particular aspects, the gene comprises a nucleic acid, and/or encodes a polypeptide or peptide-coding sequences of a gene that is defective or mutated in a hematopoietic and lympho-hematopoietic disorder. In keeping with the terminology described herein, an "isolated gene" may comprise transcribed nucleic acid(s), regulatory sequences, coding sequences, or the like, isolated substantially away from other such sequences, such as other naturally occurring genes, regulatory sequences, polypeptide or peptide encoding sequences, etc. In this respect, the term "gene" is used for simplicity to refer to a nucleic acid comprising a nucleotide sequence that is transcribed, and the complement thereof. In particular aspects, the transcribed nucleotide sequence comprises at least one functional protein, polypeptide and/or peptide encoding unit. As will be understood by those in the art, this functional term "gene" includes both genomic sequences, RNA or cDNA sequences, or smaller engineered nucleic acid segments, including nucleic acid segments of a non-transcribed part of a gene, including but not limited to the non-transcribed promoter or enhancer regions of a gene. Smaller engineered gene nucleic acid segments may express, or may be adapted to express using nucleic acid manipulation technology, proteins, polypeptides, domains, peptides, fusion proteins, mutants and/or such like. Thus, a "truncated gene" refers to a nucleic acid sequence that is missing a stretch of contiguous nucleic acid residues.

Various nucleic acid segments may be designed based on a particular nucleic acid sequence, and may be of any length. By assigning numeric values to a sequence, for example, the first residue is 1, the second residue is 2, etc., an algorithm defining all nucleic acid segments can be created:

n to n+y where n is an integer from 1 to the last number of the sequence and y is the length of the nucleic acid segment minus one, where n+y does not exceed the last number of the sequence. Thus, for a 10-mer, the nucleic acid segments correspond to bases 1 to 10, 2 to 11, 3 to 12 . . . and/or so on. For a 15-mer, the nucleic acid segments correspond to bases 1 to 15, 2 to 16, 3 to 17 . . . and/or so on. For a 20-mer, the nucleic segments correspond to bases 1 to 20, 2 to 21, 3 to 22 . . . and/or so on.

The nucleic acid(s) of the present invention, regardless of the length of the sequence itself, may be combined with other nucleic acid sequences, including but not limited to, promoters, enhancers, polyadenylation signals, restriction enzyme sites, multiple cloning sites, coding segments, and the like, to create one or more nucleic acid construct(s). The overall length may vary considerably between nucleic acid constructs. Thus, a nucleic acid segment of almost any length may be employed, with the total length preferably being limited by the ease of preparation or use in the intended recombinant nucleic acid protocol.

The term "vector" is used to refer to a carrier nucleic acid molecule into which a nucleic acid sequence can be inserted for introduction into a cell where it can be replicated. Vectors of the present invention are lentivirus based as described above and in other parts of the specification. The nucleic acid molecules carried by the vectors of the invention encode therapeutic genes and will be used for carrying out gene-therapies. One of skill in the art would be well equipped to construct such a therapeutic vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described below.

(a) Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well. Control sequences comprising promoters, enhancers and other locus or transcription controlling/modulating elements are also referred to as "transcriptional cassettes".

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al., 1989, incorporated herein by reference). The promoters employed may be constitutive, tissue-specific, inducible, and/or useful under the appropriate conditions to direct high level expression of the introduced DNA segment, such as is advantageous for gene therapy or for applications such as the large-scale production of recombinant proteins and/or peptides. The promoter may be heterologous or endogenous.

Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Tables 1 lists non-limiting examples of elements/promoters that may be employed, in the context of the present invention, to regulate the expression of a RNA. Table 2 provides non-limiting examples of inducible elements, which are regions of a nucleic acid sequence that can be activated in response to a specific stimulus.

TABLE 1

| Promoter and/or Enhancer | |
|---|---|
| Promoter/Enhancer | References |
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-Dra | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |

TABLE 1-continued

Promoter and/or Enhancer

| Promoter/Enhancer | References |
|---|---|
| α-Fetoprotein | Godbout et al., 1988; Campere et al., 1989 |
| γ-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $\alpha_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; deVilliers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Gibbon Ape Leukemia Virus | Holbrook et al., 1987; Quinn et al., 1989 |

TABLE 2

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | Poly(rI)x Poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Non-limiting examples of such regions include the human LIMK2 gene (Nomoto et al., 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), DIA dopamine receptor gene (Lee, et al., 1997), insulin-like growth factor II (Wu et al., 1997), and human platelet endothelial cell adhesion molecule-1 (Almendro et al., 1996).

The lentiviral vectors of the present invention are designed, primarily, to transform cells with a therapeutic gene under the control of regulated eukaryotic promoters. Although the EF1α-promoter and the PGK promoter are preferred other promoter and regulatory signal elements as described in the Tables 1 and 2 above may also be used. Additionally any promoter/enhancer combination (as per the Eukaryotic Promoter Data Base EPDB) could also be used to drive expression of structural genes encoding the therapeutic gene of interest that is used in context with the lentiviral vectors of the present invention. Alternatively, a tissue-specific promoter for cancer gene therapy or the targeting of tumors may be employed with the lentiviral vectors of the present invention for treatment of cancers, especially hematological cancers.

Typically promoters and enhancers that control the transcription of protein encoding genes in eukaryotic cells are composed of multiple genetic elements. The cellular machinery is able to gather and integrate the regulatory information conveyed by each element, allowing different genes to evolve distinct, often complex patterns of transcriptional regulation.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Aside from this operational distinction, enhancers and promoters are very similar entities.

Promoters and enhancers have the same general function of activating transcription in the cell. They are often overlapping and contiguous, often seeming to have a very similar modular organization. Taken together, these considerations suggest that enhancers and promoters are homologous entities and that the transcriptional activator proteins bound to these sequences may interact with the cellular transcriptional machinery in fundamentally the same way.

A signal that may prove useful is a polyadenylation signal (hGH, BGH, SV40). The use of internal ribosome binding sites (IRES) elements are used to create multigene, or polycistronic, messages. IRES elements are able to bypass the ribosome scanning model of 5'-methylated cap-dependent translation and begin translation at internal sites (Pelletier and Sonenberg, 1988). IRES elements from two members of the picornavirus family (polio and encephalomyocarditis) have been described (Pelletier and Sonenberg, 1988), as well as an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

In any event, it will be understood that promoters are DNA elements which when positioned functionally upstream of a gene leads to the expression of that gene. Most transgenes that will be transformed using the lentiviral vectors of the present invention are functionally positioned downstream of a promoter element.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

(b) Multiple Cloning Sites

Vectors of the present invention can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

(c) Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

(d) Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

(e) Polyadenylation Signals

In eukaryotic gene expression, one will typically include a polyadenylation signal to effect proper polyadenylation of the transcript. The nature of the polyadenylation signal is not believed to be crucial to the successful practice of the invention, and any such sequence may be employed. Some examples include the SV40 polyadenylation signal or the bovine growth hormone polyadenylation signal, convenient and known to function well in various target cells. Polyadenylation may increase the stability of the transcript or may facilitate cytoplasmic transport.

(f) Origins of Replication

In order to propagate a vector of the invention in a host cell, it may contain one or more origins of replication sites (often termed "ori"), which is a specific nucleic acid sequence at which replication is initiated. Alternatively an autonomously replicating sequence (ARS) can be employed if the host cell is yeast.

(g) Selectable and Screenable Markers

In certain embodiments of the invention, cells transduced with the lentivectors of the present invention may be identified in vitro or in vivo by including a marker in the expression vector. Such markers would confer an identifiable change to the transduced cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genetic constructs that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

E. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous nucleic acid encoded by the vectors of this invention. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a lentivector of the invention bearing a therapeutic gene construct, has been introduced. Therefore, recombinant cells are distinguishable from naturally occurring cells which do not contain a recombinantly introduced nucleic acid.

In certain embodiments, it is contemplated that RNAs or proteinaceous sequences may be co-expressed with other selected RNAs or proteinaceous sequences in the same host cell. Co-expression may be achieved by co-transfecting the host cell with two or more distinct recombinant vectors. Alternatively, a single recombinant vector may be constructed to include multiple distinct coding regions for RNAs, which could then be expressed in host cells transfected with the single vector.

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). Some examples of host cells used in this invention include but are not limited to virus packaging cells, virus producer cells, 293T cells, human hematopoietic progenitor cells, human hematopoietic stem cells, $CD34^+$ cells $CD4^+$ cells, and the like.

(a) Tissues and Cells

A tissue may comprise a host cell or cells to be transformed or contacted with a nucleic acid delivery composition and/or an additional agent. The tissue may be part or separated from an organism. In certain embodiments, a tissue and its constituent cells may comprise, but is not limited to, blood (e.g., hematopoietic cells (such as human hematopoietic progenitor cells, human hematopoietic stem cells, $CD34^+$ cells $CD4^+$ cells), lymphocytes and other blood lineage cells), bone marrow, brain, stem cells, blood vessel, liver, lung, bone, breast, cartilage, cervix, colon, cornea, embryonic, endometrium, endothelial, epithelial, esophagus, facia, fibroblast, follicular, ganglion cells, glial cells, goblet cells, kidney, lymph node, muscle, neuron, ovaries, pancreas, peripheral blood, prostate, skin, skin, small intestine, spleen, stomach, testes.

(b) Organisms

In certain embodiments, the host cell or tissue may be comprised in at least one organism. In certain embodiments, the organism may be, human, primate or murine. In other embodiments the organism may be any eukaryote or even a prokaryote (e.g., a eubacteria, an archaea), as would be understood by one of ordinary skill in the art (see, for example, webpage http://phylogeny.arizona.edu/tree/phylogeny.html). Some lentivectors of the invention may employ control sequences that allow them to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of the lentivectors of the invention, as well as production of the nucleic acids encoded by the lentivectors and their cognate polypeptides, proteins, or peptides some of which are therapeutic genes or proteins which will be used for gene therapies.

F. Injectable Compositions and Pharmaceutical Formulations

To achieve gene-therapy using the lentiviral vector compositions of the present invention, one would generally contact a cell in need thereof with a lentiviral vector comprising a therapeutic gene. The cell will further be in an organism such as a human in need of the gene therapy. The routes of administration will vary, naturally, with the location and nature of the disease, and include, e.g., intravenous, intrarterial, intradermal, transdermal, intramuscular, intranasal, subcutaneous, percutaneous, intratracheal, intraperitoneal, intratumoral, perfusion and lavage. The cells will also sometimes be isolated from the organisms, exposed to the lentivector ex vivo, and reimplanted afterwards.

Injection of lentiviral nucleic acid constructs of the invention may be delivered by syringe or any other method used for injection of a solution, as long as the expression construct can pass through the particular gauge of needle required for injection. A novel needleless injection system has recently been described (U.S. Pat. No. 5,846,233) having a nozzle defining an ampule chamber for holding the solution and an energy device for pushing the solution out of the nozzle to the site of delivery. A syringe system has also been described for use in gene therapy that permits multiple injections of predetermined quantities of a solution precisely at any depth (U.S. Pat. No. 5,846,225).

Solutions of the nucleic acids as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intraarterial, intramuscular, subcutaneous, intratumoral and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

The terms "contacted" and "exposed," when applied to a cell, are used herein to describe the process by which a therapeutic lentiviral vector is delivered to a target cell.

For gene-therapy to discrete, solid, accessible tumors, intratumoral injection, or injection into the tumor vasculature is specifically contemplated. Local, regional or systemic administration also may be appropriate. For tumors of >4 cm, the volume to be administered will be about 4-10 ml (preferably 10 ml), while for tumors of <4 cm, a volume of about 1-3 ml will be used (preferably 3 ml). Multiple injections delivered as single dose comprise about 0.1 to about 0.5 ml volumes. The viral particles may advantageously be contacted by administering multiple injections to the tumor, spaced at approximately 1 cm intervals. Systemic administration is preferred for conditions such as hematological malignancies.

Continuous administration also may be applied where appropriate. Delivery via syringe or catherization is preferred. Such continuous perfusion may take place for a period from about 1-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs.

Treatment regimens may vary as well, and often depend on type of disease and location of diseased tissue, and factors such as the health and the age of the patient. The clinician will be best suited to make such decisions based on the known efficacy and toxicity (if any) of the therapeutic formulations based on lentiviral vectors of the present invention.

The treatments may include various "unit doses." A unit dose is defined as containing a predetermined-quantity of the therapeutic composition comprising a lentiviral vector of the present invention. The quantity to be administered, and the particular route and formulation, are within the skill of those in the clinical arts. A unit dose need not be administered as a single injection but may comprise continuous infusion over a set period of time. Unit dose of the present invention may conveniently be described in terms of transducing units (T.U.) of lentivector, as defined by tittering the vector on a cell line such as HeLa or 293. Unit doses range from $10^3$, $10^4$, $10^5$, $10^6$, $10^7$, $10^8$, $10^9$, $10^{10}$, $10^{11}$, $10^{12}$, $10^{13}$ T.U. and higher.

G. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methodology Employed in Examples 1 through 5 Vector Preparation

Production of MLV- and HIV-derived vectors pseudotyped with the vesicular stomatitis virus (VSV) G envelope protein was achieved by transient co-transfection of three plasmids into 293T epithelial cell line as described in Naldini et al 1996a. MLV vector particles were produced using the CMV-GagPol plasmid as packaging construct (Scharfmann et al., 1991), and a vector derived from pSLX, which expressed GFP from the CMV promoter. The HIV-derived packaging construct used was pCMVΔR8.91, which encodes the HIV-1 Gag and Pol precursors, as well as the regulatory proteins Tat and Rev (Zufferey et al., 1997). VSV G was expressed from pMD.G.

The HIV vector plasmids were derivatives of the original pHR' backbone (Naldini et al., 1996a), with the following modifications. Self-inactivating vectors were produced from the previously described SIN-18 vector, which contains a deletion in the U3 region of the 3'LTR from nt. −418 to nt. −18, removing all the transcriptionally active sequences (Zufferey et al., 1998). Briefly, the pHR' SIN plasmids (also see maps in FIG. 6, FIG. 7, FIG. 9 and FIG. 9) were generated as follows; a KpnI-XbaI fragment containing the polypurine tract and the 3'LTR was excised from a pHR' plasmid and subcloned into the corresponding sites of pUC18. This plasmid was digested completely with EcoRV and partially with PvuII and self-ligated. A plasmid carrying a 400-nucleotide deletion of U3 was recovered. An XhoI linker was inserted into the EcoRI site of the deletion plasmid, and an XhoI-XbaI fragment was cloned back into the pHR' CMVlacZ plasmid digested with the corresponding enzymes. All other SIN-18 plasmids were obtained by substituting reporter genes (encoding luciferase, GFP and Neo) for lacZ. The pHR' vector plasmids used differed from the plasmids originally described (Naldini et al., 1996) by a XhoI-KpnI deletion removing 118 nucleotides from the Nef coding sequence upstream of the polypurine tract and a deletion of 1,456 nucleotides of human sequence downstream of the 3' LTR. This human sequence remained from the original cloning of a HXB2 proviral genome. The two deletions did not affect vector titers or transgene expression in dividing 293T cells.

Insertion of the EF1alpha was done by inserting a ClaI-BamHI cassette containing a EF1-GFP insert, into ClaI-BamHI site of pHR'-GFP-W-SIN (Zufferey et al. 1999)

The maps shown in FIG. 6, FIG. 7, FIG. 9 and FIG. 9 depict the plasmid constructs pHR-CMV-GFP, pHR-EF1-GFP, pHR-EF1-GFP-SIN and pHR-EF1-GFP-W-SIN.

The phosphoglycerate kinase (PGK) promoter corresponded to nucleotides 424 to 930 of the murine PGK gene (Genbank accession number M18735). The EF1α promoter was derived from the pEF-BOS plasmid (Mizushima and Nagata, 1990), and comprised nucleotides 373 to 1561 of the human elongation factor EF1α gene (Genbank accession number: J04617). After transient transfection of the three plasmids by calcium phosphate in 293T cells, the supernatant was harvested, concentrated by 2 rounds of ultracentrifugation, and resuspended in serum-free Cellgro® SCGM medium (BioWhittaker Europe, Verviers, Belgium). Viral stocks were stored at −70° C. and titers determined by transduction and flow cytometry analysis of GFP expression in HeLa cells as previously described (Zufferey et al., 1997). Titers were comprised between $5 \times 10^7$ and $10^8$ HeLa-transducing units (TU) per ml.

Purification and Transduction of CD34$^+$ Cells

Cord blood (CB) samples were obtained according to institutional guidelines and CD34$^+$ cells were purified as described (Arrighi et al., 1999). In brief, CB mononuclear cells recovered after Ficoll-Paque (Pharmacia, Uppsala, Sweden) gradient centrifugation were incubated on ice with anti-CD34 M450 Dynabeads as described by the manufacturer. After several washes to eliminate unbound cells, CD34+ cells were recovered from the beads by incubation for 15 minutes at 37° C. with the "Detach-a-bead" included in the kit. Cells were immediately washed, and analyzed by flow cytometry. The percentage of purified CD34+ cells was 89±7.0. For transduction, $10^5$ cells were seeded in 96-well plates in 100 μl of Cellgro® SCGM medium supplemented with antibiotics (Gibco BRL, Life Technologies LTD, Paisley, Scotland, U.K.), with $10^{-4}$ M dithiothreitol (Fluka Biochemika, Buchs, Switzerland) and TPO. After overnight incubation, $10^6$ (typically), or $10^5$ to $5 \times 10^6$ (for dose-response analysis) HeLa-transducing units (TU) of vector were added per well, and the volume was adjusted to 200 μl with Cellgro® SCGM medium containing TPO. After 24 hours, cells were washed, diluted to 400 μA in IMDM supplemented with 10% of FCS (both from Gibco BRL, Life Technologies LTD), antibiotics, and FLT3-L, TPO and SCF for 3 days. Cells were either directly analyzed for GFP and CD34 expression, or further cultured with the 3 growth factors. For experiments shown in FIG. 1, concentrated viral stocks were treated with DNAse I prior to incubation with cells in order to eliminate DNA contaminants that may interfere with further PCR analysis. Briefly, $10^6$ TU of vector was incubated for 30' at 37° C. in a final volume of 20 μl containing 20 μg/ml Dnase I (DNAse I, Roche Diagnostics, Rotkreuz, Switzerland) and 10 mM MgCl2. Then, 80 μl of Cellgro was added and the resulting 100 μl were added to 100 μl of Cellgro containing $10^5$ CD34+ cells. Cells were then cultured as described above.

PCR Analysis after Transduction of CD34+ Cells

Cells ($5 \times 10^5$) were lysed in 18 μl of 50 mM Tris.HCl, pH 8.0, 20 mM NaCl, 1 mM EDTA, 1% SDS. Proteinase K (2 μl at 10 mg/ml) was added and samples were incubated for 30' at 55° C. After digestion, 200 μl of water was added and samples were boiled for 10' to inactivate proteinase K. PCR amplification was performed using HotStarTaq (Qiagen, GmbH, Hilden, Germany) in a final volume of 50 μl and 2 μl or 0.7 μl of extract with the following cycles: 95° C. 15'; 40 cycles 94° C. 30'', 60° C. 1', 72° C. 1', plus 10' extension phase at 72° C. Sequences of the PCR primers were: 5' hIL2 gcaactcctgtct-tgcattg; 3' hIL2 aatgtgagcatcctggtgag; 5'GFP gtgagcaagggc-gaggagc; 3'GFP cttgatgccgttcttctgcttgt. Conditions were adjusted to observe decrease in final PCR product yield when diluting samples by a factor of 3 (see FIG. 1A).

Purification and Transduction of Primary Human T Cells

Peripheral blood mononuclear cells were purified from buffy coats of healthy donors over a Ficoll-Hypaque gradient. Macrophages were removed by plastic adherence for 2 hrs at 37° C., and the remaining cells were incubated with a cocktail of monoclonal antibodies against HLA-DR, CD25, CD69, CD19, CD16, CD11b and CD14 (Pharmingen). After a 30-min incubation on ice, cells were washed twice and incubated with magnetic beads (Dynabeads; Dynal, Oslo, Norway) conjugated with goat anti-mouse IgG, at a 1:4 target/bead ratio. Thirty minutes later, bead-bound cells were removed using a magnet. Remaining cells were further purified through two more rounds at an increased target/bead ratio (1:10). This purification protocol typically resulted in a 99.5% pure population of resting T cells, as determined by flow cytometry analysis with antibodies against the activation markers HLA-DR, CD25 and CD69. Cells maintained in RPMI 1640 supplemented with 10% FCS, 5 mM penicillin and streptomycin (GIBCO BRL) and 2 mM glutamine (GIBCO BRL) were activated with phytohemagglutinin (Sigma) at 3 μg/ml for 48 hrs and subsequently cultured in RPMI 1640 containing 10% fetal calf serum and recombinant interleukin-2 (Sigma) at 10 U/ml. $5 \times 10^5$ cells were transduced with various lentiviral vectors at a MOI of 5 HeLa-transducing unit per cell in 24-well plates in the presence of PHA, in a final volume of 500 μl. Flow cytometry analysis of GFP expression was performed five days after transduction.

Cytokines

All cytokines were recombinant human material. GM-CSF (Leucomax) from Essex Chimie & Sandoz (Basel, Switzerland) was used at 20 ng/ml, G-CSF (Neupogen) from Roche (Basel, Switzerland) at 10 ng/ml, and erythropoietin (Eprex) from Cilag (Schaffhausen, Switzerland), at 2 U/ml. Other cytokines were purchased from Peprotech EC (London, U.K.) and used at the following concentrations: FLT3-L 25 ng/ml, TPO 10 U/ml, SCF 20 ng/ml, interleukin-3 10 ng/ml, TNF 40 ng/ml and IL-4 20 ng/ml.

Antibodies and Immunoreactants

Phycoerythrin-conjugated monoclonal antibodies (MAb) were the following: anti-CD34 (mIgG1 clone 8G12) from Becton-Dickinson (Mountain View, Calif.), anti-glycoph-orin-A (mIgG1, clone JC 159), anti-CD42b (mIgG2a, clone AN51) an isotypic controls from Dako A/S (Glostrup, Denmark). Biotin-labeled MAbs: Anti-CD14 (mIgG2a, clone UCHM1) from Ancell Corp (Bayport, Minn.), and anti-CD15 (mIgM cloneDU-HL60-3) from Sigma (St Louis, Mo.), and isotypic controls from Ancell. Allophycocyanin (APC)-labeled streptavidin was from Pharmingen (San Diego, Calif.). Anti-CD34 mIgG coated M450 Dynabeads were from Dynal A/S (Oslo, Norway).

In vitro Differentiation

Megakaryocytic differentiation was evaluated after 10 days of expansion culture with FLT3-L, TPO, and SCF. For the other lineages, cells were washed after 9-11 days of expansion culture with FLT3-L, TPO, and SCF, and incubated with EPO, IL-3 and SCF for erythroid differentiation, GM-CSF and SCF for monocytic differentiation, and G-CSF and SCF for granulocytic differentiation. Differentiation into dendritic cells was performed as previously described (Arrighi et al., 1999). Briefly, transduced CD34+ cells were expanded for 14 to 28 days with FLT3-L, TPO, and SCF. Cells were then induced into mature DC by exposure to GM-CSF and IL-4 for 3 days, followed by GM-CSF, IL-4 and TNF for 3 more days. The amplification ratio was comprised between 100 and 1000 depending on the experiment and the cell lineage.

Flow Cytometry Analysis

Cells were analyzed as described (Arrighi et al., 1999), on a FACScalibur (Becton-Dickinson) with slight modifications. FL-1 was used for GFP, FL-2 for PE-labeled MAbs, FL-3 for identification of living cells with the non-permeant DNA dye 7-amino-actinomycin D (Sigma) (Schmid et al., 1994), and FL-4 for biotinylated MAbs indirectly labeled with strepta-vidin-APC. Cell suspensions were adjusted to 0.5% paraformaldehyde prior to analysis. Data were analyzed using WINMDI software written by J. Trotter at Scripps Institute (La Jolla, Calif.) and CellQuest software (Becton-Dickinson).

Example 1

Transduction of Human Hematopoietic Progenitors with MLV Vectors and HIV-Based Lentivectors Human cord blood CD34+ cells were purified by a single round of positive selection with magnetic beads, resulting in preparations approximately 90% pure. Cells were maintained overnight in serum-free medium supplemented with TPO, and were exposed for 24 hrs to MLV- or HIV-based GFP-expressing vectors pseudotyped with the G protein of vesicular stomatitis virus (VSV G), prepared by transient transfection of 293T cells as previously described (Naldini et al., 1996a; Zufferey et al., 1997). The lentiviral packaging system used in these experiments was of a so-called second generation (Zufferey et al., 1997), comprising the HIV-1 gag, pol, tat and rev genes. The multiplicity of infection (MOI) was 10 HeLa-transducing unit (TU) per CD34$^+$ cell. After transduction, cells were incubated for another three days in medium containing FCS, FLT3-L, TPO and SCF, and analyzed by flow cytometry for GFP (FIG. 1) and CD34 expression and lysed for PCR analysis. The relative potencies of three internal transcription units were compared within the context of lentivectors: the cytomegalovirus immediate early (CMV), the phosphoglycerate kinase (PGK) and the alpha chain of elongation factor 1α (EF1α) promoters.

Figure 1A:
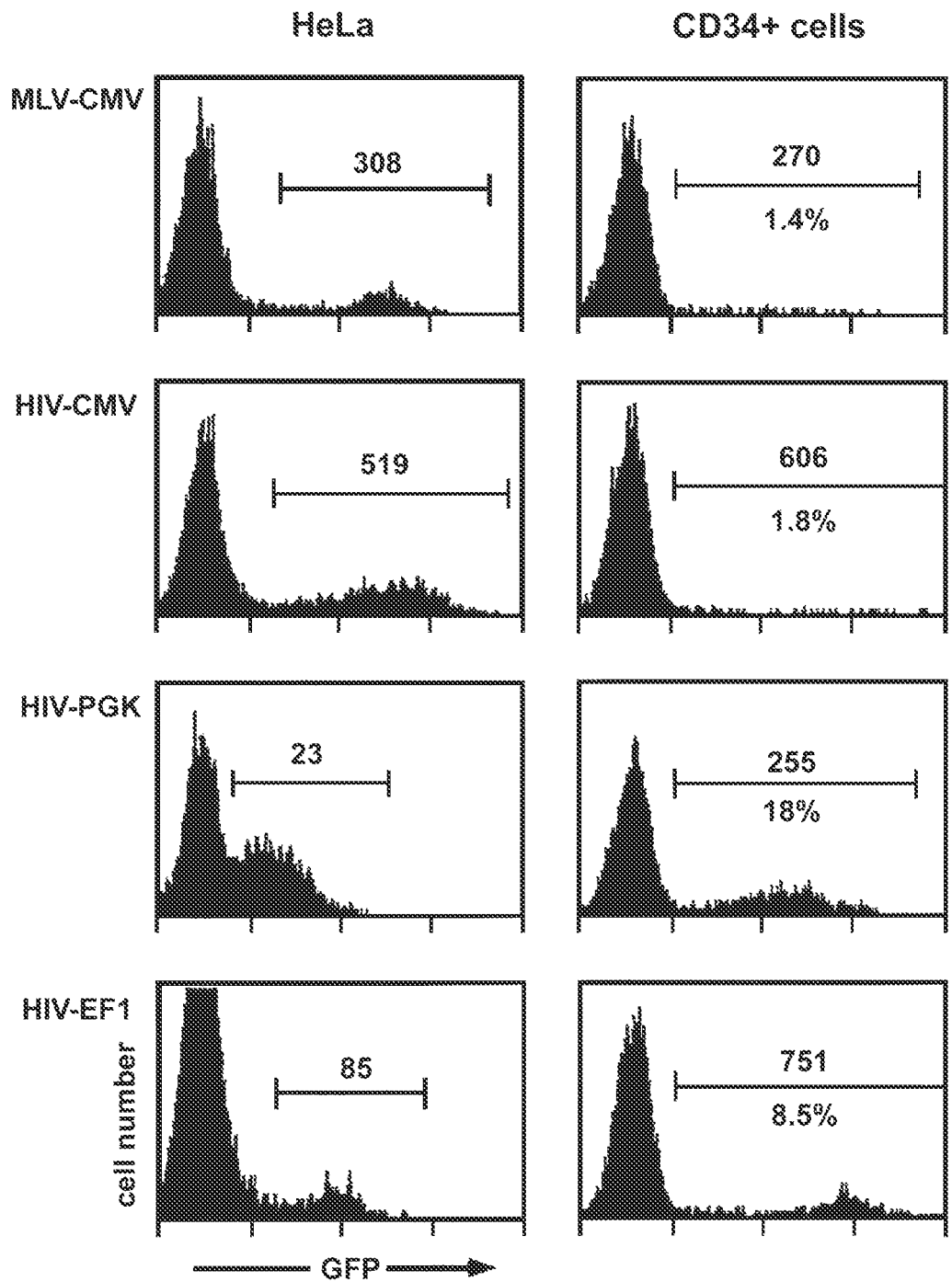
FIG. 1A and FIG. 1B. Transgene transfer and expression after transduction of human CD34$^+$ cells with MLV and HIV vectors. Human CD34$^+$ cells from umbilical cord blood ($10^5$ cells) were transduced with $10^6$ HeLa-transducing units (TU) of MLV- or the indicated HIV-derived GFP encoding vectors, previously treated with DNAse I, as described in materials and methods. After 4 days, cells were analyzed by flow cytometry for GFP expression (FIG. 1A) and lysed for PCR analysis of the presence of GFP transgene (FIG. 1B). Results from one experiment representative of two independent evaluations are shown. Expression of the GFP transgene after transduction of human CD34$^+$ cells or HeLa cells. Results are represented as histograms of GFP fluorescence intensity (x-axis, four-log scale) versus cell number (y-axis, linear). GFP$^+$ cells (within marker) were analyzed for percentage (lower number) and median of fluorescence intensity (upper number). Percentages were omitted in HeLa cells since the histograms were obtained from titration experiments of the corresponding vectors (FIG. 1A). Presence of the GFP transgene after transduction and expansion of human CD34$^+$ cells. Cellular extracts equivalent to 5000 cells (upper panel) were amplified as described in the section entitled Examples with GFP-specific primers, together with IL-2 specific primers as internal controls. Sizes of the corresponding PCR products are indicated. Lanes are: M, molecular weight marker; HeLa (negative control for GFP, positive control for IL-2); 4.5, a clone of HeLa containing one copy of HIV-CMV-GFP vector; 0, untransduced CD34$^+$ cells; MLV-CMV-PGK-EF1, CD34$^+$ cells transduced with the corresponding vectors (see FIG. 1A); CMV-EPO, CD34$^+$ cells transduced with HIV-CMV vector (lane CMV) and analyzed after expansion and differentiation into erythroid cells (see text); CMV-GM, same as CMV-EPO but analyzed after expansion and differentiation into monocytic cells (see text); PGK-EPO and PGK-GM, same as CMV-EPO and CMV-GM but from CD34+ cells transduced with HIV-CMV vector (lane PGK). To ensure for proportionality, cellular extracts equivalent to 1700 cells (lower panel) were amplified separately (FIG. 1B).
Figure 1B:
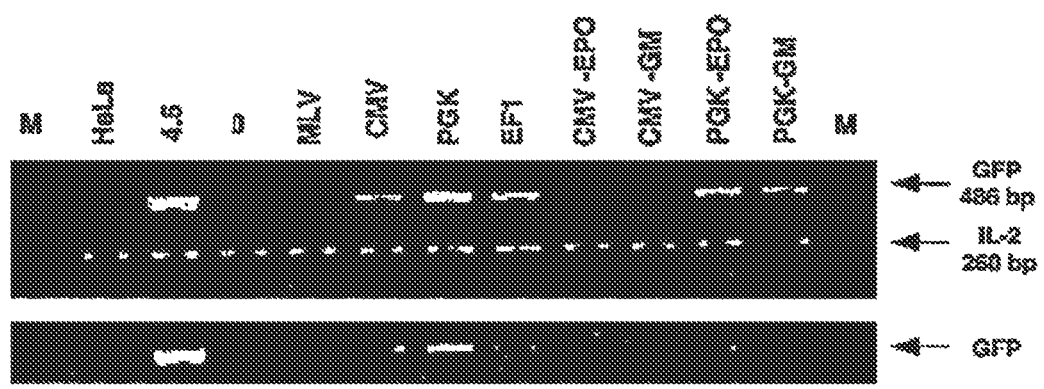

As shown in FIG. 1A, a sharp subpopulation of GFP-positive hematopoietic progenitors could only be seen when cells were transduced with HIV vectors containing the PGK or the EF1α promoters. Cells transduced with MLV vector or HIV vector containing the CMV promoter displayed only a small percentage of GFP-positive cells, together with a high heterogeneity in GFP expression. A side-by-side comparison of GFP expression after transduction of HeLa and CD34$^+$ cells revealed that the promoters examined behaved quite differently in these two cell types. The PGK promoter was weak in HeLa cells (overlap between GFP$^+$ and GFP$^-$ cells) and strong in HPCs. The EF1α promoter was intermediate in HeLa cells and very potent in HPCs, with a mean value typically 100 times higher in transduced than in control HPCs. The CMV promoter, whether in an MLV or an HIV vector, was equally strong in HeLa cells, contrasting with its low activity in transduced HPCs. A PCR-based quantification performed at the time of the flow cytometry analysis (FIG. 1B) indicated that the low expression from the MLV-CMV vector in HPCs was due at least in part to poor gene transfer in these cells, a consequence of the limited stimulation of CD34$^+$ cells during transduction. In contrast, the low expression in HPCs exposed to the HIV-CMV vector (FIG. 1A) could not be explained by a low frequency of transduction, since equivalent amounts of transgene DNA were present in cells transduced with all three HIV vectors (FIG. 1B). This indicates that the CMV promoter does not govern efficient expression in hematopoietic progenitors, a finding in accordance with previous reports (Miyoshi et al., 1999; Case et al., 1999; An et al., 2000).

The inventors also ascertained that GFP expression originated from integrated proviruses. For this, a PCR analysis was performed following 3 weeks of expansion of the transduced CD34$^+$ cells. During this time period, the cell numbers increased by a factor of 900 to 1800, depending on conditions and experiments. In the particular experiment illustrated here (FIG. 1B), the percentage of cells expressing GFP from the PGK promoter decreased by a factor of approximately 2 after expansion and differentiation into erythroid or monocytoid cells, which paralleled a slight decrease in GFP DNA copy number. This confirms that the bulk of transgene DNA remains in the cells after massive expansion, excluding its presence as unintegrated forms. This also correlates the previous demonstration that long term transgene expression cannot be detected after transduction with integrase-deficient HIV-vectors (Naldini et al., 1996b).

Thus, the EF1α promoter induces high transgene expression in lentivector-transduced CD34$^+$ cells Example 2

Figure 2:
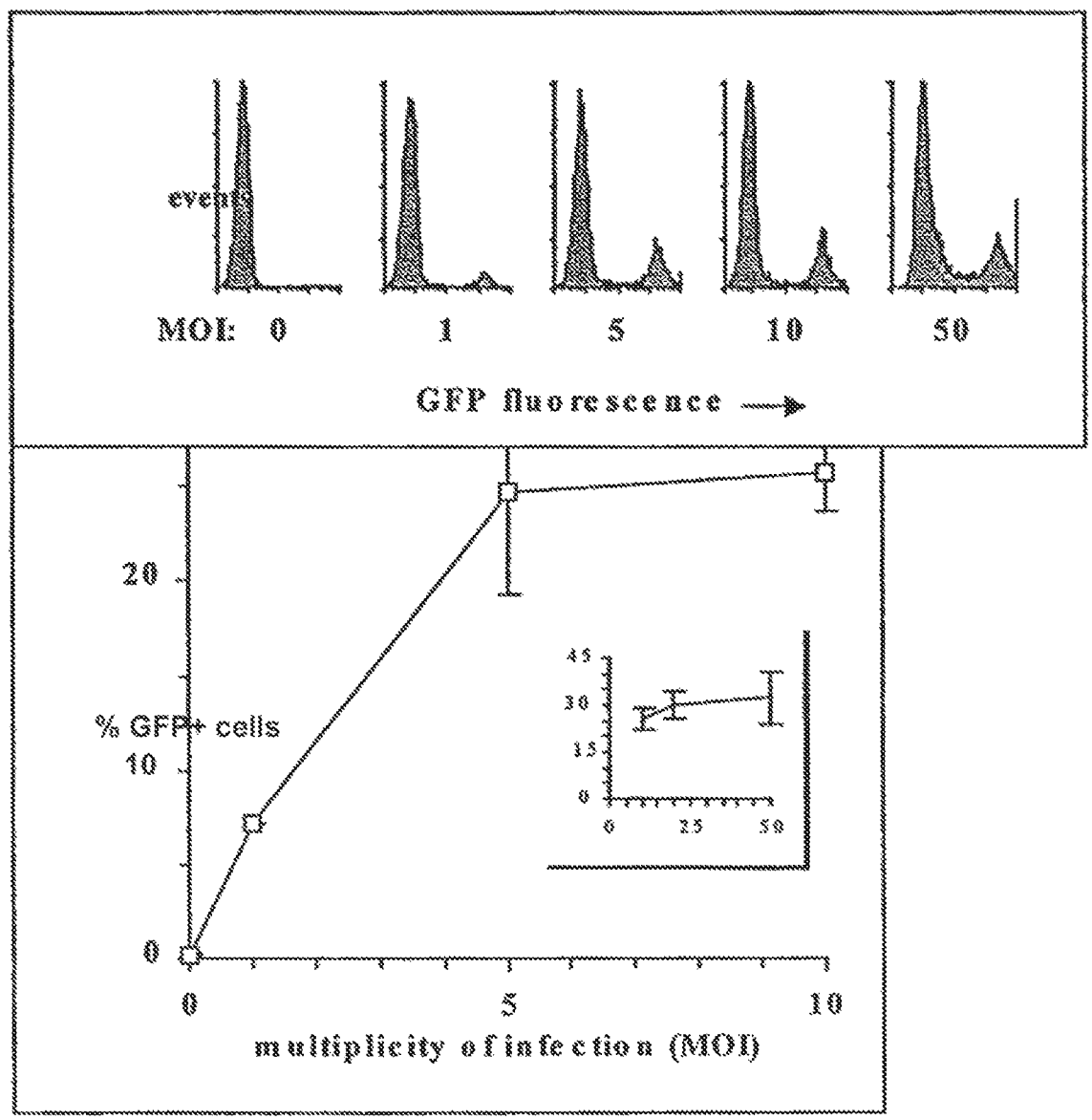
FIG. 2. Effect of MOI on transduction efficiency of lentivectors in human CD34$^+$ cells. $10^5$ CD34$^+$ cells were transduced with various doses (1, 2, 5, 10, 20 and $50\times10^5$ TU) of EF1α-GFP lentiviral vector allowing multiplicities of infection (MOI) ranging from 1 to 50. GFP expression was analyzed by flow cytometry after 4 days. Upper panel: Data from one representative experiment are shown as frequency histograms of GFP fluorescence intensity versus cell number (events). Gates for GFP$^+$ cells were setup according to untransfected cells (MOI 0). Lower panel: Mean percentages of GFP$^+$ cells obtained with MOIs of 0 to 10 and 10 to 50 are represented in the main panel and in the insert respectively.

Transduction of Human CD34$^+$ Cells as a Function of Increasing Vector Concentration The high levels of GFP expression induced by the EF1α-containing HIV-derived vector allowed for a reliable determination of gene transfer efficiency, because even low numbers of transduced cells were easily detected. This vector was thus used to evaluate the influence of the MOI on the transduction efficiency of CD34$^+$ cell (FIG. 2). Although the percentage of GFP$^+$ cells initially increased as a direct function of the MOI, the curve flattened starting at a MOI of 5, reaching a maximum of 25% GFP$^+$ cells (±5% according to experiments) at MOIs 20 and above. In the absence of optimal cytokine-induced proliferation, only a fraction of human CD34$^+$ cells is thus permissive to lentivector-mediated transduction, as previously suggested (Sutton et al., 1999).

Example 3

Transgene Expression in Hematopoietic Lineages after Transduction of CD34$^+$ Cells with HIV Vectors Containing PGK and EF1α Promoters An important issue for the genetic treatment of a variety of lympho-hematological disorders will be the levels of expression of the putatively therapeutic transgene in the appropriate subset of differentiated cells. In that respect, recent reports using HIV-based vectors with an internal expression cassette driven by the CMV promoter have documented the incapacity of this transcriptional element to induce strong transgene expression in precursors as well as mature blood cells (Miyoshi et al., 1999; Case et al., 1999). To identify more suitable alternatives, hematopoietic progenitors transduced with HIV-based vectors containing the PGK or the EF1α promoters were differentiated in vitro to compare the relative potency of these vectors in various hematopoietic lineages. For this, transduced CD34$^+$ cells were first expanded for 7-14 days in FLT3-L/TPO/SCF and then incubated in various differentiating media for an additional 5-to-10-day period, allowing the generation of erythroid cells, granulocytes and monocytes. Megakaryocytes were induced in FLT3-L/TPO/SCF exclusively. For dendritic cells (DC), transduced CD34$^+$ cells were expanded for 14 to 28 days with FLT3-L/TPO/SCF. Cells were then induced into mature DC by exposure to GM-CSF/IL-4 for 3 days, followed by exposure to GM-CSF/IL-4/TNF for 3 more days.

The differentiated cells were then analyzed by flow cytometry to determine the percentage of lineage-specific marker$^+$/GFP$^+$ cells, as well as the relative levels of GFP expression in the differentiated populations (FIG. 3). Transgene expression was high in all lineages examined after transduction of precursors with the EF1α-containing lentiviral vector, with a signal-to-noise ratio (mean of fluorescence intensity of GFP$^+$ cells divided by mean of fluorescence intensity of GFP$^-$ cells) comprised between 150 and 200 depending on the cell type. The PGK promoter induced lower and more variable levels of GFP expression in differentiated cells. Expression of GFP under the control of the PGK promoter was highest in DCs where it was only 3.5 less potent than that driven from the EF1α promoter, and worst in erythroid cells (glycophorin$^+$), where it was 11 fold weaker than its EF1α counterpart. However, even in this case, the signal-to-noise ratio was still high enough to permit a clear discrimination between GFP$^+$ and GFP$^-$ cells, allowing for the reliable analysis of transgene expression.

Taken together, these data indicate that the transduction of human CD34+ cells with HIV-based vectors containing internal promoters derived from the EF1α and to a lesser extent the PGK gene results in high levels of transgene expression in several hematopoietic lineages.

Example 4

EF1α Promoter-Based Lentiviral Vectors Induce High Levels of Transgene Expression in Primary T Lymphocytes The system used in these studies did not allow for the easy differentiation of CD34$^+$ precursors into cells of the lymphocytic lineage. Therefore, to compare the relative value of CMV-, PGK- and EF1α-containing HIV-derived vectors in these cells, mature T-lymphocytes purified from the peripheral blood were directly used as transduction targets (FIG. 4). The results revealed the same hierarchy as observed in HPCs and in the various other blood cell lineages, with the EF1α promoter inducing levels of GFP expression significantly higher than those yielded by the PGK promoter, whereas cells transduced with CMV-based vectors exhibited levels of GFP expression that were incompatible with proper detection by flow cytometry. Experiments using human primary B cells show that the CMV promoter is very active in these cells. This indicates that the poor activity of the CMV promoter is not universal in human hematopoietic cells.

Example 5

Influence of SIN Design and WPRE on Transgene Expression

Figure 5:
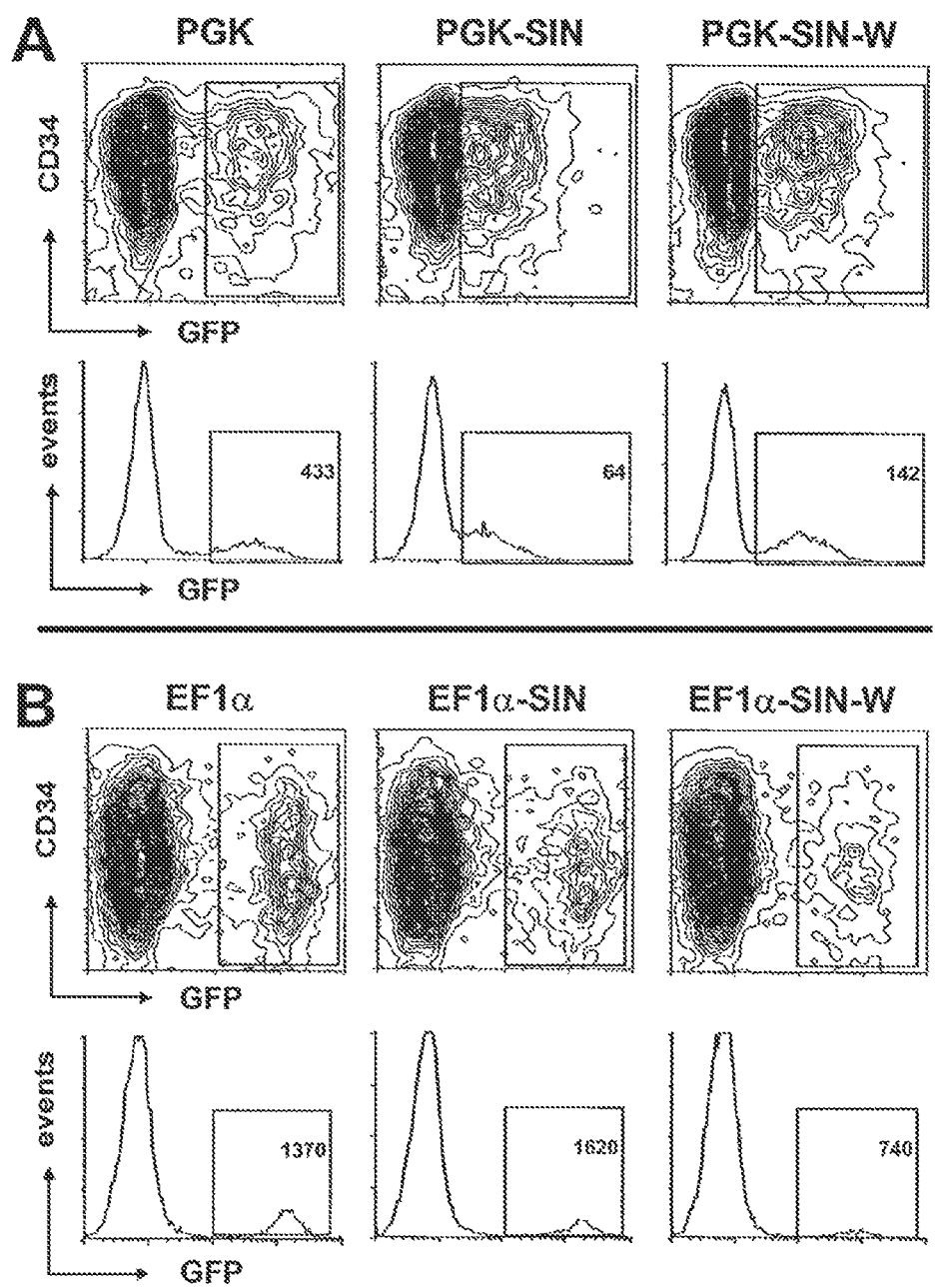

The use of self-inactivating (SIN) 3'LTR U3-deleted HIV vectors increases the biosafety of this system and avoids a possible interference between the viral LTR and the vector's internal promoter (Zufferey et al., 1998). EF1α- and PGK-containing HIV-derived SIN vectors were therefore tested for their ability to induce high levels of transgene expression in hematopoietic precursors (FIG. 5). The SIN design was accompanied by a dramatic decrease (6 fold) in GFP expression within the context of the PGK vector, whereas it instead had a slightly yet reproducibly positive effect when introduced in the EF1α vector. Inserting the sequence for the woodchuck hepatitis virus posttranscriptional regulatory element (WPRE) (Donello et al., 1998) upstream of the 3' LTR has been shown to promote transgene expression from HIV-derived vectors in some targets (Zufferey et al., 1999). It indeed stimulated GFP production from the PGK promoter by a factor of 2.15 in hematopoietic precursors. In contrast, it exerted a negative effect on expression from the highly active EF1α promoter, with a decrease by a factor of 1.85. Taken together, these indicate that the strong EF1α promoter is less sensitive than the PGK promoter to a self-inactivating configuration, making it a better candidate for gene expression in hematopoietic cells.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,682,195
U.S. Pat. No. 4,683,202
U.S. Pat. No. 5,466,468
U.S. Pat. No. 5,645,897
U.S. Pat. No. 5,686,279
U.S. Pat. No. 5,705,629
U.S. Pat. No. 5,846,225
U.S. Pat. No. 5,846,233
U.S. Pat. No. 5,925,565
U.S. Pat. No. 5,928,906
U.S. Pat. No. 5,935,819
U.S. Pat. No. 5,994,136
U.S. Pat. No. 6,013,516
U.S. Pat. No. 6,136,597
EP 266,032

Akkina, Walton, Chen, Li, Planelles, Chen, "High-efficiency gene transfer into CD34+ cells with a human immunodeficiency virus type 1-based retroviral vector pseudotyped with vesicular stomatitis virus envelope glycoprotein G," *J. Virol.,* 70:2581-2585, 1996.

Almendro et al., "Cloning of the human platelet endothelial cell adhesion molecule-1 promoter and its tissue-specific expression. Structural and functional characterization," *J. Immunol.,* 157(12):5411-5421, 1996.

An, Wersto, Agricola, Metzger, Lu, Amado, Chen, Donahue, "Marking and gene expression by a lentivirus vector in transplanted human and nonhuman primate CD34(+) cells," *J. Virol.,* 74:1286-1295, 2000.

Angel, Bauman, Stein, Dellus, Rahmsdorf, and Herrlich, "12-O-tetradecanoyl-phorbol-13-acetate Induction of the Human Collagenase Gene is Mediated by an Inducible Enhancer Element Located in the 5' Flanking Region," *Mol. Cell. Biol.,* 7:2256, 1987a.

Angel, Imagawa, Chiu, Stein, Imbra, Rahmsdorf, Jonat, Herrlich, and Karin, "Phorbol Ester-Inducible Genes Contain a Common cis Element Recognized by a TPA-Modulated Trans-acting Factor," *Cell,* 49:729, 1987b Arrighi, Hauser, Chapuis, Zubler, Kindler, "Long-term culture of human CD34(+) progenitors with FLT3-ligand, thrombopoietin, and stem cell factor induces extensive amplification of a CD34(-)CD14(-) and CD34(-)CD14 (+) dendritic cell precursor," *Blood,* 93:2244-2252, 1999.

Atchison and Perry, "Tandem Kappa Immunoglobulin Promoters are Equally Active in the Presence of the Kappa Enhancer: Implications for Model of Enhancer Function," *Cell,* 46:253, 1986.

Atchison and Perry, "The Role of the Kappa Enhancer and its Binding Factor NF-kappa B in the Developmental Regulation of Kappa Gene Transcription," *Cell,* 48:121, 1987.

Banerji et al., "Expression of a Beta-Globin Gene is Enhanced by Remote SV40 DNA Sequences," *Cell,* 27:299, 1981.

Banerji, Olson, and Schaffner, "A lymphocyte-specific cellular enhancer is located downstream of the joining region in immunoglobulin heavy-chain genes," *Cell*, 35:729, 1983.

Berkhout, Silverman, and Jeang, "Tat Trans-activates the Human Immunodeficiency Virus Through a Nascent RNA Target," *Cell*, 59:273, 1989.

Bhatia, Bonnet, Kapp, Wang, Murdoch, Dick, "Quantitative analysis reveals expansion of human hematopoietic repopulating cells after short-term ex vivo culture," *J. Exp. Med.*, 186:619-624, 1997.

Blanar, Baldwin, Flavell, and Sharp, "A gamma-interferon-induced factor that binds the interferon response sequence of the MHC class I gene, H-2 Kb," *EMBO J.*, 8:1139, 1989.

Blomer, Naldini, Kafri, Trono, Verma, Gage, "Highly efficient and sustained gene transfer in adult neurons with a lentivirus vector," *J. Virol.*, 71:6641-6649, 1997.

Bodine and Ley, "An enhancer element lies 3' to the human a gamma globin gene," *EMBO J.*, 6:2997, 1987.

Boshart, Weber, Jahn, Dorsch-Hasler, Fleckenstein, and Schaffner, "A very strong enhancer is located upstream of an immediate early gene of human cytomegalovirus," *Cell*, 41:521, 1985.

Bosze, Thiesen, and Charnay, "A transcriptional enhancer with specificity for erythroid cells is located in the long terminal repeat of the friend murine leukemia virus," *EMBO J.*, 5:1615, 1986.

Braddock, Chambers, Wilson, Esnouf, Adams, Kingsman, and Kingsman, "HIV-I Tat activates presynthesized RNA in the nucleus," *Cell*, 58:269, 1989.

Brown, Tiley, Cullen, "Efficient polyadenylation within the human immunodeficiency virus type 1 long terminal repeat requires flanking U3-specific sequences," *J. Virol.*, 65:3340-3343, 1991.

Bulla and Siddiqui, "The hepatitis B virus enhancer modulates transcription of the hepatitis B virus surface-antigen gene from an internal location," *J. Virol.*, 62:1437, 1986.

Campbell and Villarreal, "Functional analysis of the individual enhancer core sequences of polyoma virus: cell-specific uncoupling of DNA replication from transcription," *Mol. Cell. Biol.*, 8:1993, 1988.

Campere and Tilghman, "Postnatal repression of the alpha-fetoprotein gene is enhancer independent," *Genes and Dev.*, 3:537, 1989.

Campo, Spandidos, Lang, Wilkie, "Transcriptional control signals in the genome of bovine papilloma virus type 1," *Nature*, 303:77, 1983.

Carbonelli et al. "A plasmid vector for isolation of strong promoters in *E. coli*," *FEMS Microbiol Lett.* 177(1):75-82, 1999.

Case, Price, Jordan, Yu, Wang, Bauer, Haas, Xu, Stripecke, Naldini, Kohn, Crooks, "Stable transduction of quiescent CD34(+)CD38(-) human hematopoietic cells by HIV-1 based lentiviral vectors," *Proc. Natl. Acad. Sci. USA*, 96:2988-2993, 1999.

Celander and Haseltine, "Glucocorticoid Regulation of Murine Leukemia Virus Transcription Elements is Specified by Determinants Within the Viral Enhancer Region," *J. Virology*, 61:269, 1987.

Celander, Hsu, and Haseltine, "Regulatory Elements Within the Murine Leukemia Virus Enhancer Regions Mediate Glucocorticoid Responsiveness," *J. Virology*, 62:1314, 1988.

Chandler, Maler, and Yamamoto, "DNA Sequences Bound Specifically by Glucocorticoid Receptor in vitro Render a Heterlogous Promoter Hormone Responsive in vivo," *Cell*, 33:489, 1983.

Chandler et al., "RNA splicing specificity determined by the coordinated action of RNA recognition motifs in SR proteins," *Proc Natl Acad Sci USA*. 94(8):3596-3601, 1997.

Chang, Erwin, and Lee, "Glucose-regulated Protein (GRP94 and GRP78) Genes Share Common Regulatory Domains and are Coordinately Regulated by Common Trans-acting Factors," *Mol. Cell. Biol.*, 9:2153, 1989.

Chatterjee, Lee, Rentoumis, and Jameson, "Negative Regulation of the Thyroid-Stimulating Hormone Alpha Gene by Thyroid Hormone: Receptor Interaction Adjacent to the TATA Box," *Proc Natl. Acad. Sci. U.S.A.*, 86:9114, 1989.

Chen and Okayama, "High-efficiency transformation of mammalian cells by plasmid DNA," *Mol. Cell. Biol.* 7:2745-2752, 1987

Chemington and Ganem, "Regulation of polyadenylation in human immunodeficiency virus (HIV): contributions of promoter proximity and upstream sequences," *Embo. J.*, 11:1513-1524, 1992.

Choi, Chen, Kriegler, and Roninson, "An altered pattern of cross-resistance in multi-drug-resistant human cells results from spontaneous mutations in the mdr-1 (p-glycoprotein) gene," *Cell*, 53:519, 1988.

Cocea, "Duplication of a region in the multiple cloning site of a plasmid vector to enhance cloning-mediated addition of restriction sites to a DNA fragment," *Biotechniques*, 23:814-816, 1997.

Cohen, Walter, and Levinson, "A Repetitive Sequence Element 3' of the Human c-Ha-ras1 Gene Has Enhancer Activity," J. Cell. Physiol., 5:75, 1987.

Corbeau, et al., *PNAS (U.S.A.*,) 93(24):14070-14075, 1996.

Costa, Lai, Grayson, and Darnell, "The Cell-Specific Enhancer of the Mouse Transthyretin (Prealbumin) Gene Binds a Common Factor at One Site and a Liver-Specific Factor(s) at Two Other Sites," *Mol. Cell. Biol.*, 8:81, 1988.

Cripe, Haugen, Turk, Tabatabai, Schmid, Durst, Gissmann, Roman, and Turek, "Transcriptional Regulation of the Human Papilloma Virus-16 E6-E7 Promoter by a Keratinocyte-Dependent Enhancer, and by Viral E2 Trans-Activator and Repressor Gene Products: Implications for Cervical Carcinogenesis," *EMBO J.*, 6:3745, 1987.

Culotta and Hamer, "Fine Mapping of a Mouse Metallothionein Gene Metal-Response Element," *Mol. Cell. Biol.*, 9:1376, 1989.

Dandolo, Blangy, and Kamen, "Regulation of Polyma Virus Transcription in Murine Embryonal Carcinoma Cells," *J. Virology*, 47:55, 1983.

Dao, Hannum, Kohn, Nolta, "FLT3 ligand preserves the ability of human CD34+ progenitors to sustain long-term hematopoiesis in immune-deficient mice after ex vivo retroviral-mediated transduction," *Blood*, 89:446-456, 1997.

Dao, Hashino, Kato, Nolta, "Adhesion to fibronectin maintains regenerative capacity during ex vivo, culture and transduction of human hematopoietic stem and progenitor cells," *Blood*, 92:4612-4621, 1998.

Deschamps, Meijlink, and Verma, "Identification of a Transcriptional Enhancer Element Upstream From the Proto-Oncogene Fos," *Science*, 230:1174, 1985.

De Villiers, Schaffner, Tyndall, Lupton, and Kamen, "Polyoma Virus DNA Replication Requires an Enhancer," *Nature*, 312:242, 1984.

DeZazzo, Kilpatrick, Imperiale, "Involvement of long terminal repeat U3 sequences overlapping the transcription control region in human immunodeficiency virus type 1 mRNA 3' end formation," *Mol. Cell. Biol.*, 11:1624-1630, 1991.

Donello, Loeb, Hope, "Woodchuck hepatitis virus contains a tripartite posttranscriptional regulatory element," *J. Virol.*, 72:5085-5092, 1998.

Dorrell, Gan, Pereira, Hawley, Dick, "Expansion of human cord blood CD34(+)CD38(−) cells in ex vivo culture during retroviral transduction without a corresponding increase in SCID repopulating cell (SRC) frequency: dissociation of SRC phenotype and function," *Blood*, 95:102-110, 2000.

Edbrooke, Burt, Cheshire, and Woo, "Identification of cis-acting sequences responsible for phorbol ester induction of human serum amyloid a gene expression via a nuclear-factor-kappa 13-like transcription factor," *Mol. Cell. Biol.*, 9:1908, 1989.

Edlund, Walker, Barr, and Rutter, "Cell-specific expression of the rat insulin gene: evidence for role of two distinct 5' flanking elements," *Science*, 230:912, 1985.

Fechheimer, Boylan, Parker, Sisken, Patel and Zimmer, "Transfection of mammalian cells with plasmid DNA by scrape loading and sonication loading," *Proc Acad. Sci. USA* 84:8463-8467, 1987

Feng and Holland, "HIV-I Tat Trans-Activation Requires the Loop Sequence Within Tar," *Nature*, 334:6178, 1988.

Firak and Subramanian, "Minimal Transcription Enhancer of Simian Virus 40 is a 74-Base-Pair Sequence that Has Interacting Domains," *Mol. Cell. Biol.*, 6:3667, 1986.

Foecking and Hofstetter, "Powerful and Versatile Enhancer-Promoter Unit for Mammalian Expression Vectors," *Gene*, 45(1):101-105, 1986.

Fujita, Shibuya, Hotta, Yamanishi, and Taniguchi, "Interferon-Beta Gene Regulation: Tandemly Repeated Sequences of a Synthetic 6-bp Oligomer Function as a Virus-Inducible Enhancer," *Cell*, 49:357, 1987.

Gilles, Morris, Oi, and Tonegawa, "A tissue-specific transcription enhancer element is located in the major intron of a rearranged immunoglobulin heavy-chain gene," *Cell*, 33:717, 1983.

Gilmartin, Fleming, Oetjen, "Activation of HIV-1 pre-mRNA 3' processing in vitro requires both an upstream element and TAR," *Embo. J.*, 11:4419-4428, 1992.

Gloss, Bernard, Seedorf, and Klock, "The Upstream Regulatory Region of the Human Papilloma Virus-16 Contains an E2 Protein-Independent Enhancer Which is Specific for Cervical Carcinoma Cells and Regulated by Glucocorticoid Hormones," *EMBO J.*, 6:3735, 1987.

Godbout, Ingram, and Tilghman, "Fine-Structure Mapping of the Three Mouse Alpha-Fetoprotein Gene Enhancers," *Mol. Cell. Biol.*, 8:1169, 1988.

Goodbourn, Burstein, and Maniatis, "The Human Beta-Interferon Gene Enhancer is Under Negative Control," *Cell*, 45:601, 1986.

Goodbourn and Maniatis, "Overlapping Positive and Negative Regulatory Domains of the Human β-Interferon Gene," *Proc. Natl. Acad. Sci. USA*, 85:1447, 1988.

Gopal, "Gene transfer method for transient gene expression, stable transformation, and cotransformation of suspension cell cultures," *Mol. Cell. Biol.* 5:1188-1190, 1985.

Gossen and Bujard, *Proc. Natl. Acad. Sci.*, 89:5547-5551, 1992.

Graham and Van Der Eb, "A new technique for the assay of infectivity of human adenovirus 5 DNA," *Virology* 52:456-467, 1973

Greene, Bohnlein, and Ballard, "HIV-1, and Normal T-Cell Growth: Transcriptional Strategies and Surprises," *Immunology Today*, 10:272, 1989

Grosschedl and Baltimore, "Cell-Type Specificity of Immunoglobulin Gene Expression is Regulated by at Least Three DNA Sequence Elements," *Cell*, 41:885, 1985.

Haslinger and Karin, "Upstream Promoter Element of the Human Metallothionein-II Gene Can Act Like an Enhancer Element," *Proc Natl. Acad. Sci. U.S.A.*, 82:8572, 1985.

Hauber and Cullen, "Mutational Analysis of the Trans-Activation-Responsive Region of the Human Immunodeficiency Virus Type I Long Terminal Repeat," *J. Virology*, 62:673, 1988.

Hen, Borrelli, Fromental, Sassone-Corsi, and Chambon, "A Mutated Polyoma Virus Enhancer Which is Active in Undifferentiated Embryonal Carcinoma Cells is not Repressed by Adenovirus-2 E1A Products," *Nature*, 321:249, 1986.

Hensel, Meichle, Pfizenmaier, and Kronke, "PMA-Responsive 5' Flanking Sequences of the Human TNF Gene," *Lymphokine Res.*, 8:347, 1989.

Herr and Clarke, "The SV40 Enhancer is Composed of Multiple Functional Elements That Can Compensate for One Another," *Cell*, 45:461, 1986.

Hirochika, Browker, and Chow, "Enhancers and Trans-Acting E2 Transcriptional Factors of Papilloma Viruses," *J. Virol.*, 61:2599, 1987.

Hirsch, Gaugler, Deagostini-Bauzin, Bally-Cuif, and Gordis, "Identification of Positive and Negative Regulatory Elements Governing Cell-Type-Specific Expression of the Neural-Cell-Adhesion-Molecule Gene," *Mol. Cell. Biol.*, 10:1959, 1990.

Holbrook, Gulino, and Ruscetti, "cis-Acting Transcriptional Regulatory Sequences in the Gibbon Ape Leukemia Virus (GALV) Long Terminal Repeat," *Virology*, 157:211, 1987.

Horlick and Benfield, "The upstream muscle-specific enhancer of the rat muscle creatine kinase gene is composed of multiple elements," *Mol. Cell. Biol.*, 9:2396, 1989.

Huang, Ostrowski, Berard, and Hagar, "Glucocorticoid regulation of the ha-musv p21 gene conferred by sequences from mouse mammary tumor virus," *Cell*, 27:245, 1981.

Hug, Costas, Staeheli, Aebi, and Weissmann, "Organization of the Murine Mx Gene and Characterization of its Interferon- and Virus-Inducible Promoter," *Mol. Cell. Biol.*, 8:3065, 1988.

Hwang, Lim, and Chae, "Characterization of the S-Phase-Specific Transcription Regulatory Elements in a DNA-Replication-Independent Testis-Specific H2B (TH2B) Histone Gene," *Mol. Cell. Biol.*, 10:585, 1990.

Imagawa, Chiu, and Karin, "Transcription Factor AP-2 Mediates Induction by Two Different Signal-Transduction Pathways: Protein Kinase C and cAMP," *Cell*, 51:251, 1987.

Imbra and Karin, "Phorbol Ester Induces the Transcriptional Stimulatory Activity of the SV40 Enhancer," *Nature*, 323:555, 1986.

Imler, Lemaire, Wasvlyk, and Waslyk, "Negative Regulation Contributes to Tissue Specificity of the Immunoglobulin Heavy-Chain Enhancer," *Mol. Cell. Biol*, 7:2558, 1987.

Imperiale and Nevins, "Adenovirus 5 E2 Transcription Unit: an E1A-Inducible Promoter with an Essential Element that Functions Independently of Position or Orientation," *Mol. Cell. Biol.*, 4:875, 1984.

Jakobovits, Smith, Jakobovits, and Capon, "A Discrete Element 3' of Human Immunodeficiency Virus 1 (HIV-1) and HIV-2 mRNA Initiation Sites Mediates Transcriptional Activation by an HIV Trans-Activator," *Mol. Cell. Biol.*, 8:2555, 1988.

Jameel and Siddiqui, "The Human Hepatitis B Virus Enhancer Requires Transacting Cellular Factor(s) for Activity," *Mol. Cell. Biol.,* 6:710, 1986.

Jaynes, Johnson, Buskin, Gartside, and Hauschka, "The Muscle Creatine Kinase Gene is Regulated by Multiple Upstream Elements, Including a Muscle-Specific Enhancer," *Mol. Cell. Biol.,* 8:62, 1988.

Johnson, Wold, and Hauschka, "Muscle creatine kinase sequence elements regulating skeletal and cardiac muscle expression in transgenic mice," *Mol. Cell. Biol.,* 9:3393, 1989.

Kadesch and Berg, "Effects of the Position of the Simian Virus 40 Enhancer on Expression of Multiple Transcription Units in a Single Plasmid," *Mol. Cell. Biol.,* 6:2593, 1986.

Karin, Haslinger, Heguy, Dietlin, and Cooke, "Metal-Responsive Elements Act as Positive Modulators of Human Metallothionein-IIA Enhancer Activity," *Mol. Cell. Biol.,* 7:606, 1987.

Katinka, Yaniv, Vasseur, and Blangy, "Expression of Polyoma Early Functions in Mouse Embryonal Carcinoma Cells Depends on Sequence Rearrangements in the Beginning of the Late Region," *Cell,* 20:393, 1980.

Kawamoto, Makino, Niw, Sugiyama, Kimura, Anemura, Nakata, and Kakunaga, "Identification of the Human Beta-Actin Enhancer and its Binding Factor," *Mol. Cell. Biol.,* 8:267, 1988.

Kiledjian, Su, Kadesch, "Identification and characterization of two functional domains within the murine heavy-chain enhancer," Mol. Cell. Biol., 8:145, 1988.

Klamut, Gangopadyhay, Worton, and Ray, "Molecular and Functional Analysis of the Muscle-Specific Promoter Region of the Duchenne Muscular Dystrophy Gene," *Mol. Cell. Biol.,* 10:193, 1990.

Klein et al., "High-velocity microprojectiles for delivering nucleic acids into living cells," *Nature,* 327:70-73, 1987.

Koch, Benoist, and Mathis, "Anatomy of a new 13-cell-specific enhancer," *Mol. Cell. Biol.,* 9:303, 1989.

Kraus et al., "Alternative promoter usage and tissue specific expression of the mouse somatostatin receptor 2 gene," *FEBS Lett.,* 428(3):165-170, 1998.

Kohn, Nolta, Weinthal, Bahner, Yu, Lilley, Crooks, "Toward gene therapy for Gaucher disease," *Hum. Gene Ther.,* 2:101-105, 1991.

Kriegler and Botchan, "A retrovirus LTR contains a new type of eukaryotic regulatory element," *In: Eukaryotic Viral Vectors,* Gluzman (ed.), Cold Spring Harbor, Cold Spring Harbor Laboratory, NY, 1982.

Kriegler et al., "Promoter substitution and enhancer augmentation increases the penetrance of the sv40 a gene to levels comparable to that of the harvey murine sarcoma virus ras gene in morphologic transformation," *In: Gene Expression,* Alan Liss (Ed.), Hamer and Rosenberg, N.Y., 1983.

Kriegler et al., "Viral Integration and Early Gene Expression Both Affect the Efficiency of SV40 Transformation of Murine Cells: Biochemical and Biological Characterization of an SV40 Retrovirus," *In: Cancer Cells 2/Oncogenes and Viral Genes,* Van de Woude et al. (eds), Cold Spring Harbor, Cold Spring Harbor Laboratory, 1984.

Kriegler, Perez, Defay, Albert and Liu, "A Novel Form of TNF/Cachectin Is a Cell-Surface Cytotoxix Transmembrane Protein: Ramifications for the Complex Physiology of TNF," *Cell,* 53:45, 1988.

Kuhl, De La Fuenta, Chaturvedi, Parinool, Ryals, Meyer, and Weissman, "Reversible Silencing of Enhancers by Sequences Derived From the Human IFN-alpha Promoter," *Cell,* 50:1057, 1987.

Kunz, Zimmerman, Heisig, and Heinrich, "Identification of the Promoter Sequences Involved in the Interleukin-6-Dependent Expression of the Rat Alpha-2-Macroglobulin Gene," *Nucl. Acids Res.,* 17:1121, 1989.

Lareyre et al., "A 5-kilobase pair promoter fragment of the murine epididymal retinoic acid-binding protein gene drives the tissue-specific, cell-specific, and androgen-regulated expression of a foreign gene in the epididymis of transgenic mice," *J Biol. Chem.,* 274(12):8282-8290, 1999.

Larsen, Harney, and Moore, "Repression medaites cell-type-specific expression of the rat growth hormone gene," *Proc Natl. Acad. Sci. USA.,* 83:8283, 1986.

Laspia, Rice, and Mathews, "HIV-1 Tat protein increases transcriptional initiation and stabilizes elongation," *Cell,* 59:283, 1989.

Latimer, Berger, and Baumann, "Highly conserved upstream regions of the alpha.sub.1-antitrypsin gene in two mouse species govern liver-specific expression by different mechanisms," *Mol. Cell. Biol.,* 10:760, 1990.

Lee, Mulligan, Berg, and Ringold, "Glucocorticoids Regulate Expression of Dihydrofolate Reductase cDNA in Mouse Mammary Tumor Virus Chimaeric Plasmids," *Nature,* 294:228, 1981.

Lee et al., "Activation of beta3-adrenoceptors by exogenous dopamine to lower glucose uptake into rat adipocytes," *J Auton Nery Syst.* 74(2-3):86-90, 1997.

Levenson et al., "Internal ribosomal entry site-containing retroviral vectors with green fluorescent protein and drug resistance markers," *Human Gene Therapy,* 9:1233-1236, 1998.

Levinson, Khoury, VanDeWoude, and Gruss, "Activation of SV40 Genome by 72-Base-Pair Tandem Repeats of Moloney Sarcoma Virus," *Nature,* 295:79, 1982. Lewis and Emerman, "Passage through mitosis is required for oncoretroviruses but not for the human immunodeficiency virus," *J. Virol.,* 68:510-516, 1994.

Lin, Cross, Halden, Dragos, Toledano, and Leonard, "Delineation of an enhancerlike positive regulatory element in the interleukin-2 receptor .alpha.-chain gene," *Mol. Cell. Biol.,* 10:850, 1990.

Luria, Gross, Horowitz, and Givol, "Promoter Enhancer Elements in the Rearranged Alpha-Chain Gene of the Human T-Cell Receptor," EMBO J., 6:3307, 1987.

Lusky, Berg, Weiher, and Botchan, "Bovine Papilloma Virus Contains an Activator of Gene Expression at the Distal End of the Early Transcription Unit," *Mol. Cell. Biol.* 3:1108, 1983.

Lusky and Botchan, "Transient Replication of Bovine Papilloma Virus Type 1 Plasmids: cis and trans Requirements," *Proc Natl. Acad. Sci. U.S.A.,* 83:3609, 1986.

Majors and Varmus, "A Small Region of the Mouse Mammary Tumor Virus Long Terminal Repeat Confers Glucocorticoid Hormone Regulation on a Linked Heterologous Gene," *Proc. Natl. Acad. Sci. U.S.A.,* 80:5866, 1983.

Marthas et al. *J. Virol.,* 67:6047-6055, 1993.

Mazurier, Moreau-Gaudry, Maguer-Satta, Salesse, Pigeonnier-Lagarde, Ged, Belloc, Lacombe, Mahon, Reiffers, de Verneuil, "Rapid analysis and efficient selection of human transduced primitive hematopoietic cells using the humanized S65T green fluorescent protein," *Gene Ther.,* 5:556-562, 1998.

McNeall, Sanchez, Gray, Chesterman, and Sleigh, "Hyperinducible Gene Expression From a Metallotionein Promoter Containing Additional Metal-Responsive Elements," *Gene,* 76:81, 1989.

Miksicek, Heber, Schmid, Danesch, Posseckert, Beato, and Schutz, "Glucocorticoid Responsiveness of the Transcriptional Enhancer of Moloney Murine Sarcoma Virus," *Cell*, 46:203, 1986.

Miyoshi, Smith, Mosier, Verma, Torbett, "Transduction of human CD34+ cells that mediate long-term engraftment of NOD/SCID mice by HIV vectors," *Science*, 283:682-686, 1999.

Mizushima and Nagata, "pEF-BOS, a powerful mammalian expression vector," *Nucleic Acids Res.*, 18:5322, 1990.

Mordacq and Linzer, "Co-localization of Elements Required for Phorbol Ester Stimulation and Glucocorticoid Repression of Proliferin Gene Expression," *Genes and Dev.*, 3:760, 1989.

Moreau, Hen, Wasylyk, Everett, Gaub, and Chambon, "The SV40 base-repair repeat has a striking effect on gene expression both in sv40 and other chimeric recombinants," *Nucl. Acids Res.*, 9:6047, 1981.

Muesing et al., *Cell*, 48:691, 1987.

Naldini, Blomer, gallay, Ory, Mulligan, Gage, Verma, Trono, "In vivo gene delivery and stable transduction of nondividing cells by a lentiviral vector," *Science*, 272:263-267, 1996a.

Naldini, Blomer, Gage, Trono, Verma, "Efficient transfer, integration, and sustained long-term expression of the transgene in adult rat brains injected with a lentiviral vector," *Proc. Natl. Acad. Sci. USA*, 93:11382-11388, 1996b.

Ng, Gunning, Liu, Leavitt, and Kedes, "Regulation of the Human Beta-Actin Promoter by Upstream and Intron Domains," *Nuc. Acids Res.*, 17:601, 1989.

Nomoto et al., "Cloning and characterization of the alternative promoter regions of the human LIMK2 gene responsible for alternative transcripts with tissue-specific expression," *Gene*, 236(2):259-271, 1999.

Omitz, Hammer, Davison, Brinster, and Palmiter, "Promoter and enhancer elements from the rat elastase i gene function independently of each other and of heterologous enhancers," Mol. Cell. Biol. 7:3466, 1987.

Ondek, Sheppard, and Herr, "Discrete Elements Within the SV40 Enhancer Region Display Different Cell-Specific Enhancer Activities," *EMBO J.*, 6:1017, 1987.

Ory et al., *Proc. Natl. Acad. Sci.*, 93:11400-11406, 1996.

Palmiter, Chen, and Brinster, "Differential regulation of metallothionein-thymidine kinase fusion genes in transgenic mice and their offspring," *Cell*, 29:701, 1982.

Pech, Rao, Robbins, and Aaronson, "Functional identification of regulatory elements within the promoter region of platelet-derived growth factor 2," *Mol. Cell. Biol.*, 9:396, 1989.

Perez-Stable and Constantini, "Roles of fetal γ-globin promoter elements and the adult β-globin 3' enhancer in the stage-specific expression of globin genes," *Mol. Cell. Biol.*, 10:1116, 1990.

Piacibello, Sanavio, Severino, Dane, Gammaitoni, Fagioli, Perissinotto, Cavalloni, Kollet Lapidot, Aglietta, "Engraftment in nonobese diabetic severe combined immunodeficient mice of human CD34(+) cord blood cells after ex vivo expansion: evidence for the amplification and self-renewal of repopulating stem cells," *Blood*, 93:3736-3749, 1999.

Picard and Schaffner, "A Lymphocyte-Specific Enhancer in the Mouse Immunoglobulin Kappa Gene," *Nature*, 307:83, 1984.

Pinkert, Omitz, Brinster, and Palmiter, "An albumin enhancer located 10 kb upstream functions along with its promoter to direct efficient, liver-specific expression in transgenic mice," *Genes and Dev.*, 1:268, 1987.

Ponta, Kennedy, Skroch, Hynes, and Groner, "Hormonal Response Region in the Mouse Mammary Tumor Virus Long Terminal Repeat Can Be Dissociated From the Proviral Promoter and Has Enhancer Properties," *Proc. Natl. Acad. Sci. U.S.A.*, 82:1020, 1985.

Porton, Zaller, Lieberson, and Eckhardt, "Immunoglobulin heavy-chain enhancer is required to maintain transfected .gamma.2a gene expression in a pre-b-cell line," *Mol. Cell. Biol.*, 10:1076, 1990.

Potter et al., "Enhancer-dependent expression of human k immunoglobulin genes introduced into mouse pre-B lymphocytes by electroporation," *Proc Nat'l Acad. Sci. USA*, 81:7161-7165, 1984.

Queen and Baltimore, "Immunoglobulin Gene Transcription is Activated by Downstream Sequence Elements," *Cell*, 35:741, 1983.

Quinn, Farina, Gardner, Krutzsch, and Levens, "Multiple components are required for sequence recognition of the ap1 site in the gibbon ape leukemia virus enhancer," *Mol. Cell. Biol.*, 9:4713, 1989.

Redondo, Hata, Brocklehurst, and Krangel, "A T-Cell-Specific Transcriptional Enhancer Within the Human T-Cell Receptor .delta. Locus," *Science*, 247:1225, 1990.

Resendez Jr., Wooden, and Lee, "Identification of highly conserved regulatory domains and protein-binding sites in the promoters of the rat and human genes encoding the stress-inducible 78-kilodalton glucose-regulated protein," *Mol. Cell. Biol.*, 8:4579, 1988.

Reisman and Rotter, "Induced Expression From the Moloney Murine Leukemia Virus Long Terminal Repeat During Differentiation of Human Myeloid Cells is Mediated Through its Transcriptional Enhancer," *Mol. Cell. Biol.*, 9:3571, 1989.

Remington's Pharmaceutical Sciences, 15th Ed., pages 1035-1038 and 1570-1580.

Ripe, Lorenzen, Brenner, and Breindl, "Regulatory elements in the 5' flanking region and the first intron contribute to transcriptional control of the mouse alpha-1-type collagen gene," *Mol. Cell. Biol.*, 9:2224, 1989.

Rippe, Brenner and Leffert, "DNA-mediated gene transfer into adult rat hepatocytes in primary culture," *Mol. Cell. Biol.*, 10:689-695, 1990.

Rittling, Coutinho, Amarm, and Kolbe, "AP-1/jun-binding Sites Mediate Serum Inducibility of the Human Vimentin Promoter," *Nuc. Acids Res.*, 17:1619, 1989.

Roe, Reynolds, Yu, Brown, "Integration of murine leukemia virus DNA depends on mitosis," *Embo. J.*, 12:2099-2108, 1993.

Rosen, Sodroski, and Haseltine, "The location of cis-acting regulatory sequences in the human t-cell lymphotropic virus type III (HTLV-111/LAV) long terminal repeat," *Cell*, 41:813, 1988.

Sakai, Helms, Carlstedt-Duke, Gustafsson, Rottman, and Yamamoto, "Hormone-Mediated Repression: A Negative Glucocorticoid-Response Element From the Bovine Prolactin Gene," *Genes and Dev.*, 2:1144, 1988.

Sambrook, Fritsch, Maniatis, In: *Molecular Cloning: A Laboratory Manual* 2 rev.ed., Cold Spring Harbor, Cold Spring Harbor Laboratory Press, 1(77):19-17.29, 1989.

Satake, Furukawa, and Ito, "Biological activities of oligonucleotides spanning the f9 point mutation within the enhancer region of polyoma virus DNA," *J. Virology*, 62:970, 1988.

Scharfmann, Axelrod, Verma, "Long-term in vivo expression of retrovirus-mediated gene transfer in mouse fibroblast implants," *Proc. Natl. Acad. Sci. USA*, 88:4626-4630, 1991.

Schaffner, Schirm, Muller-Baden, Wever, and Schaffner, "Redundancy of Information in Enhancers as a Principle of Mammalian Transcription Control," *J. Mol. Biol.,* 201:81, 1988.

Schmid, Uittenbogaart, Keld, Giorgi, "A rapid method for measuring apoptosis and dual-color immunofluorescence by single laser flow cytometry," *J. Immunol. Methods,* 170: 145-157, 1994.

Searle, Stuart, and Palmiter, "Building a metal-responsive promoter with synthetic regulatory elements," *Mol. Cell. Biol.,* 5:1480, 1985.

Sharp and Marciniak, "HIV Tar: an RNA Enhancer?," *Cell,* 59:229, 1989.

Shaul and Ben-Levy, "Multiple Nuclear Proteins in Liver Cells are Bound to Hepatitis B Virus Enhancer Element and its Upstream Sequences," *EMBO J.,* 6:1913, 1987.

Sherman, Basta, Moore, Brown, and Ting, "Class II Box Consensus Sequences in the HLA-DR.alpha. Gene: Transcriptional Function and Interaction with Nuclear Proteins," *Mol. Cell. Biol.,* 9:50, 1989.

Sleigh and Lockett, "SV40 Enhancer Activation During Retinoic-Acid-Induced Differentiation of F9 Embryonal Carcinoma Cells," *J. EMBO,* 4:3831, 1985.

Spalholz, Yang, and Howley, "Transactivation of a Bovine Papilloma Virus Transcriptional Regulatory Element by the E2 Gene Product," *Cell,* 42:183, 1985.

Spandau and Lee, "Trans-Activation of Viral Enhancers by the Hepatitis B Virus X Protein," *J. Virology,* 62:427, 1988.

Spandidos and Wilkie, "Host-Specificities of Papilloma Virus, Moloney Murine Sarcoma Virus and Simian Virus 40 Enhancer Sequences," *EMBO J.,* 2:1193, 1983.

Stephens and Hentschel, "The Bovine Papilloma Virus Genome and its Uses as a Eukaryotic Vector," *Biochem. J.,* 248:1, 1987.

Stuart, Searle, and Palmiter, "Identification of Multiple Metal Regulatory Elements in Mouse Metallothionein-I Promoter by Assaying Synthetic Sequences," *Nature,* 317: 828, 1985.

Sullivan and Peterlin, "Transcriptional Enhancers in the HLA-DQ Subregion," *Mol. Cell. Biol.,* 7:3315, 1987.

Sutton, Reitsma, Uchida, Brown, "Transduction of human progenitor hematopoietic stem cells by human immunodeficiency virus type 1-based vectors is cell cycle dependent," *J. Virol.,* 73:3649-3660, 1999.

Sutton, Wu, Rigg, Bohnlein, Brown, "Human immunodeficiency virus type 1 vectors efficiently transduce human hematopoietic stem cells," *J. Virol.,* 72:5781-5788, 1998.

Swartzendruber and Lehman, "Neoplastic Differentiation: Interaction of Simian Virus 40 and Polyoma Virus with Murine Teratocarcinoma Cells," *J. Cell. Physiology,* 85:179, 1975.

Takebe, Seiki, Fujisawa, Hoy, Yokota, Arai, Yoshida, and Arai, "SR.alpha. Promoter: An Efficient and Versatile Mammalian cDNA Expression System Composed of the Simian Virus 40 Early Promoter and the R-U5 Segment of Human T-Cell Leukemia Virus Type 1 Long Terminal Repeat," *Mol. Cell. Biol.,* 8:466, 1988.

Taylor and Kingston, "E1A Trans-Activation of Human HSP70 Gene Promoter Substitution Mutants is Independent of the Composition of Upstream and TATA Elements," *Mol. Cell. Biol.,* 10:176, 1990.

Taylor and Kingston, "Factor Substitution in a Human HSP70 Gene Promoter: TATA-Dependent and TATA-Independent Interactions," *Mol. Cell. Biol.,* 10:165, 1990.

Taylor, Solomon, Weiner, Paucha, Bradley, and Kingston, "Stimulation of the Human Heat-Shock Protein 70 Promoter in vitro by Simian Virus 40 Large T Antigen," *J. Biol. Chem.,* 264:15160, 1989.

Tavernier, Gheysen, Duerinck, Can Der Heyden, and Fiers, "Deletion Mapping of the Inducible Promoter of Human IFN-beta Gene," *Nature,* 301:634, 1983.

Thiesen, Bosze, Henry, and Charnay, "A DNA Element Responsible for the Different Tissue Specificities of Friend and Moloney Retroviral Enhancers," *J. Virology,* 62:614, 1988.

Tronche, Rollier, Bach, Weiss, and Yaniv, "The Rat Albumin Promoter: Cooperation with Upstream Elements is Required When Binding of APF/HNF 1 to the Proximal Element is Partially Impaired by Mutation or Bacterial Methylation," *Mol. Cell. Biol.,* 9:4759, 1989.

Tronche, Rollier, Herbomel, Bach, Cereghini, Weiss, and Yaniv, "Anatomy of the Rat Albumin Promoter," *Mol. Biol. Med.,* 7:173, 1990.

Trudel and Constantini, "A 3' Enhancer Contributes to the Stage-Specific Expression of the human Beta-Globin Gene," *Genes and Dev.,* 6:954, 1987.

Tsumaki et al., "Modular arrangement of cartilage- and neural tissue-specific cis-elements in the mouse alpha2(XI) collagen promoter," J Biol. Chem. 273(36):22861-22864, 1998.

Tur-Kaspa, Teicher, Levine, Skoultchi and Shafritz, "Use of electroporation to introduce biologically active foreign genes into primary rat hepatocytes," *Mol. Cell. Biol.,* 6:716-718, 1986.

Tyndall, La Mantia, Thacker, Favaloro, and Kamen, "A Region of the Polyoma Virus Genome Between the Replication Origin and Late Protein-Coding Sequences is Required in cis for Both Early Gene Expression and Viral DNA Replication," *Nuc. Acids. Res.,* 9:6231, 1981.

Uchida, Sutton, Friera, He, Reitsma, Chang, Veres, Scollay, Weissman, "HIV, but not murine leukemia virus, vectors mediate high efficiency gene transfer into freshly isolated G0/G1 human hematopoietic stem cells," *Proc. Natl. Acad. Sci. USA,* 95:11939-11944, 1998.

Ueda, Tsuji, Yoshino, Ebihara, Yagasaki, Hisakawa, Mitsui, Manabe, Tanaka, Kobayashi, Ito, Yasukawa, Nakahata, "Expansion of human NOD/SCID-repopulating cells by stem cell factor, Flk2/Flt3 ligand, thrombopoietin, IL-6, and soluble IL-6 receptor," *J. Clin. Invest.,* 105:1013-1021, 2000.

Unutmaz, Kewal, Ramani, Marmon, Littman, "Cytokine signals are sufficient for HIV-1 infection of resting human T lymphocytes," *J. Exp. Med.,* 189:1735-1746, 1999.

Valsamakis, Schek, Alwine, "Elements upstream of the AAUAAA within the human immunodeficiency virus polyadenylation signal are required for efficient polyadenylation in vitro," *Mol. Cell. Biol.,* 12:3699-3705, 1992.

Valsamakis, Zeichner, Carswell, Alwine, "The human immunodeficiency virus type 1 polyadenylylation signal: a 3' long terminal repeat element upstream of the AAUAAA necessary for efficient polyadenylylation," *Proc. Natl. Acad. Sci. USA,* 88:2108-2112, 1991.

Vannice and Levinson, "Properties of the Human Hepatitis B Virus Enhancer: Position Effects and Cell-Type Nonspecificity," *J. Virology,* 62:1305, 1988.

Vasseur, Kress, Montreau, and Blangy, "Isolation and Characterization of Polyoma Virus Mutants Able to Develop in Multipotential Murine Embryonal Carcinoma Cells," *Proc Natl. Acad. Sci. U.S.A.,* 77:1068, 1980.

Wang and Calame, "SV40 enhancer-binding factors are required at the establishment but not the maintenance step of enhancer-dependent transcriptional activation," *Cell,* 47:241, 1986.

Watanabe et al., "Gene transfection of mouse primordial germ cells in vitro and analysis of their survival and growth control, *Experimental Cell Research,* 230:76-83, 1997.

Weber, DeVilliers, and Schaffner, "An SV40 'Enhancer Trap' Incorporates Exogenous Enhancers or Generates Enhancers From its Own Sequences," *Cell,* 36:983, 1984.

Weinberger, Jat, and Sharp, "Localization of a Repressive Sequence Contributing to B-cell Specificity in the Immunoglobulin Heavy-Chain Enhancer," *Mol. Cell. Biol.,* 8:988, 1984.

Winoto and Baltimore, "αβ-lineage-specific Expression of the α T-Cell Receptor Gene by Nearby Silencers," *Cell,* 59:649, 1989.

Wu et al., "Promoter-dependent tissue-specific expressive nature of imprinting gene, insulin-like growth factor II, in human tissues," Biochem Biophys Res Commun. 233(1): 221-226, 1997.

Yang, Burkholder, Roberts, Martinell and McCabe, "In vivo and in vitro gene transfer to mammalian somatic cells by particle bombardment," *Proc Nat'l Acad. Sci. USA,* 87:9568-9572, 1990.

Yutzey, Kline, and Konieczny, "An Internal Regulatory Element Controls Troponin I Gene Expression," *Mol. Cell. Biol.,* 9:1397, 1989.

Zhao-Emonet et al., "The equine herpes virus 4 thymidine kinase is a better suicide gene than the human herpes virus 1 thymidine kinase," *Gene Ther.* 6(9):1638-1642, 1999.

Zufferey, Nagy, Mandel, Naldini, Trono, "Multiply attenuated lentiviral vector achieves efficient gene delivery in vivo," *Nat. Biotechnol.,* 15:871-875, 1997.

Zufferey, Dull, Mandel, Bukovsky, Quiroz, Naldini, Trono, "Self-inactivating lentivirus vector for safe and efficient in vivo gene delivery," *J. Virol.,* 72:9873-9880, 1998.

Zufferey, Donello, Trono, Hope, "Woodchuck hepatitis virus posttranscriptional regulatory element enhances expression of transgenes delivered by retroviral vectors," *J. Virol.,* 73:2886-2892, 1999.

What is claimed is:

1. An isolated T cell comprising a recombinant lentiviral vector comprising: (a) an expression cassette comprising a transgene positioned under the control of a promoter, other than a CMV promoter, that is active to promote detectable transcription of the transgene at a signal-to-noise ratio of between about 10 and about 200 in both a human hematopoietic progenitor cell and a T cell; and (b) an LTR region that has reduced promoter activity relative to wild-type LTR, wherein the LTR region has been rendered substantially transcriptionally inactive by virtue of deletions in the U3 region of the 3' LTR.

2. The T cell of claim 1, wherein the promoter is capable of promoting expression of the transgene at a signal-to-noise ratio of between about 40 and about 200.

3. The T cell of claim 2, wherein the promoter is capable of promoting expression of the transgene at a signal-to-noise ratio of between about 150 and about 200.

4. The T cell of claim 1, wherein the promoter is an EF1-α promoter, a PGK promoter, a gp91hox promoter, a MHC classII promoter, a CD11 promoter, a CD4 promoter, a CD2 promoter or a gp47 promoter.

5. The T cell of claim 4, wherein the transgene is positioned under the control of the EF1-α promoter.

6. The T cell of claim 4, wherein the transgene is positioned under the control of the PGK promoter.

7. The T cell of claim 1, wherein the transgene comprises erythropoietin, an interleukin, a colony-stimulating factor, integrin αIIbβ, a multidrug resistance gene, gp91hox, gp 47, an antiviral gene, a gene coding for blood coagulation factor VIII, a gene coding for blood coagulation factor IX, a T cell antigen receptor, a B cell antigen receptor, a T cell antigen receptor in combination with a single chain antibodies (scFv), a B cell antigen receptor in combination with an ScFv, an ScFv, TNF, gamma interferon, CTLA4, B7, Melana, or MAGE.

8. The T cell of claim 7, wherein the transgene comprises an interleukin.

9. The T cell of claim 7, wherein the transgene comprises interleukin-2.

10. The T cell of claim 7, wherein the transgene comprises a T cell antigen receptor.

11. The T cell of claim 7, wherein the transgene comprises a T cell antigen receptor in combination with an scFv.

12. The T cell of claim 7, wherein the transgene comprises an scFv.

13. The T cell of claim 1, further comprising a posttranscriptional regulatory sequence positioned to promote the expression of the transgene.

14. The T cell of claim 13, wherein the posttranscriptional regulatory sequence is an intron positioned within the expression cassette.

15. The T cell of claim 14, wherein the intron is positioned in an orientation opposite the vector genomic transcript.

16. The T cell of claim 13, wherein the posttranscriptional regulatory sequence is a posttranscriptional regulatory element.

17. The T cell of claim 16, wherein the posttranscriptional regulatory element is woodchuck hepatitis virus posttranscriptional regulatory element (WPRE).

18. The T cell of claim 16, wherein the posttranscriptional regulatory element is hepatitis B virus posttranscriptional regulatory element (HPRE).

* * * * *

```
SEQUENCE LISTING

<160> NUMBER OF SEQ ID NOS: 4

<210> SEQ ID NO 1
<211> LENGTH: 20
<212> TYPE: DNA
<213> ORGANISM: Homo sapiens

<400> SEQUENCE: 1
gcaactcctg tctttgcattg                                              20

<210> SEQ ID NO 2
<211> LENGTH: 20
<212> TYPE: DNA
<213> ORGANISM: Homo sapiens

<400> SEQUENCE: 2
aatgtgagca tcctggtgag                                               20

<210> SEQ ID NO 3
<211> LENGTH: 19
<212> TYPE: DNA
<213> ORGANISM: Homo sapiens

<400> SEQUENCE: 3
gtgagcaagg gcgaggagc                                                19

<210> SEQ ID NO 4
<211> LENGTH: 23
<212> TYPE: DNA
<213> ORGANISM: Homo sapiens

<400> SEQUENCE: 4
cttgatgccg ttcttctgct tgt                                           23
```